(12) United States Patent
Suzuki et al.

(10) Patent No.: US 9,478,749 B2
(45) Date of Patent: Oct. 25, 2016

(54) ANTHRACENE COMPOUND, LIGHT-EMITTING ELEMENT, LIGHT-EMITTING DEVICE, ELECTRONIC APPLIANCE, AND LIGHTING DEVICE

(71) Applicant: SEMICONDUCTOR ENERGY LABORATORY CO., LTD., Atsugi-shi, Kanagawa-ken (JP)

(72) Inventors: Masato Suzuki, Kanagawa (JP); Nobuharu Ohsawa, Kanagawa (JP); Satoko Shitagaki, Kanagawa (JP); Harue Osaka, Kanagawa (JP)

(73) Assignee: Semiconductor Energy Laboratory Co., LTD., Kanagawa-ken (JP)

( * ) Notice: Subject to any disclaimer, the term of this patent is extended or adjusted under 35 U.S.C. 154(b) by 390 days.

(21) Appl. No.: 14/222,786

(22) Filed: Mar. 24, 2014

(65) Prior Publication Data
US 2016/0163991 A1   Jun. 9, 2016

(30) Foreign Application Priority Data
Mar. 28, 2013   (JP) .................... 2013-069849

(51) Int. Cl.
*H01L 51/00* (2006.01)
*C09K 11/02* (2006.01)
(Continued)

(52) U.S. Cl.
CPC .......... *H01L 51/0056* (2013.01); *C07C 13/72* (2013.01); *C07D 209/86* (2013.01);
(Continued)

(58) Field of Classification Search
CPC .................. H01L 51/0068; H01L 51/0058
See application file for complete search history.

(56) References Cited

U.S. PATENT DOCUMENTS

| | | | |
|---|---|---|---|
| 6,984,462 B2 * | 1/2006 | Kim .................. | C07C 13/72 257/102 |
| 7,326,474 B2 * | 2/2008 | Kim .................. | C07C 13/72 252/301.16 |

(Continued)

FOREIGN PATENT DOCUMENTS

CN            001338499              3/2002

*Primary Examiner* — Mohammad Islam
*Assistant Examiner* — Ankush Singal
(74) *Attorney, Agent, or Firm* — Nixon Peabody LLP; Jeffrey L. Costellia

(57) ABSTRACT

An organic compound having a high $T_1$ level is provided. An element emitting phosphorescence in the blue and green regions is provided. An organic compound having a high glass-transition temperature is provided. A light-emitting element, a light-emitting device, an electronic appliance, or a lighting device having high heat resistance is provided. A light-emitting element includes at least a hole-transport layer, a light-emitting layer, and an electron-transport layer between an anode and a cathode. An anthracene compound represented by General Formula (G1) is contained in at least one of the hole-transport layer, the light-emitting layer, and the electron-transport layer.

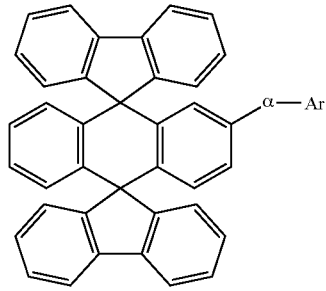

(G1)

11 Claims, 28 Drawing Sheets

(51) Int. Cl.
*C09K 11/06* (2006.01)
*C07C 13/72* (2006.01)
*C07D 209/86* (2006.01)
*C07D 241/38* (2006.01)
*H01L 51/50* (2006.01)

(52) U.S. Cl.
CPC ........... *C07D241/38* (2013.01); *C09K 11/025* (2013.01); *C09K 11/06* (2013.01); *H01L 51/0072* (2013.01); *H01L 51/0085* (2013.01); *C09K 2211/1007* (2013.01); *C09K 2211/1059* (2013.01); *C09K 2211/185* (2013.01); *H01L 51/5016* (2013.01); *H01L 51/5056* (2013.01); *H01L 51/5072* (2013.01)

(56) References Cited

U.S. PATENT DOCUMENTS

| | | | |
|---|---|---|---|
| 2004/0023060 A1* | 2/2004 | Kim | C07C 13/72 428/690 |
| 2007/0215867 A1* | 9/2007 | Kawakami | C07C 211/61 257/40 |
| 2007/0252517 A1* | 11/2007 | Owczarczyk | C09K 11/06 313/504 |
| 2012/0012826 A1* | 1/2012 | Kim | C07D 209/56 257/40 |
| 2012/0061617 A1* | 3/2012 | Heun | C08G 61/02 252/301.35 |
| 2012/0326138 A1* | 12/2012 | Yi | C07D 487/04 257/40 |

* cited by examiner

FIG. 5A
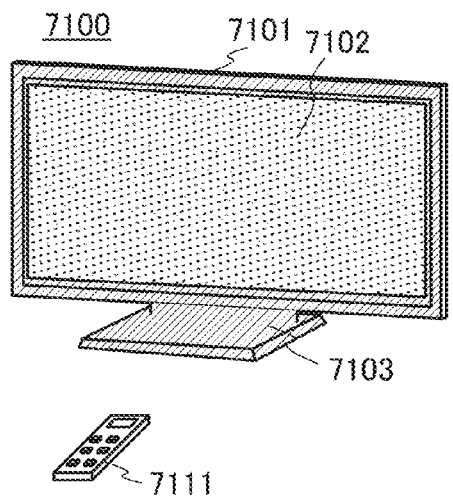
FIG. 5B
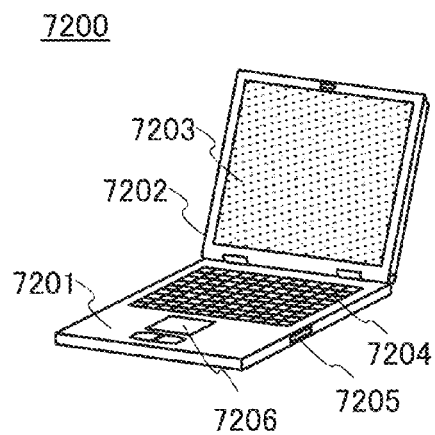
FIG. 5C
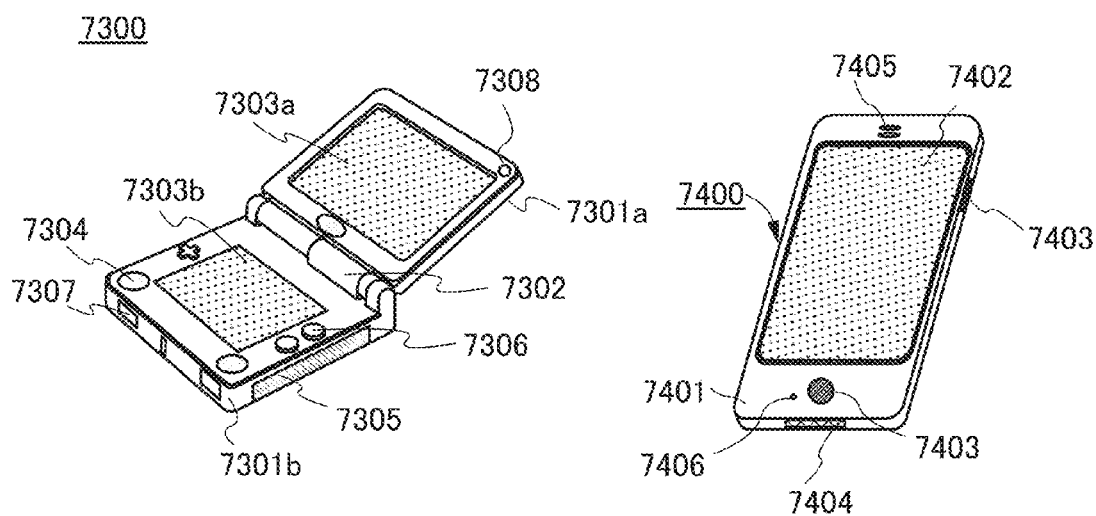
FIG. 5D
FIG. 5E
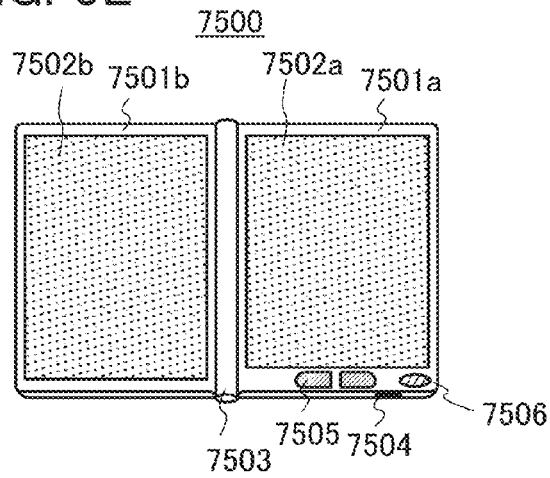

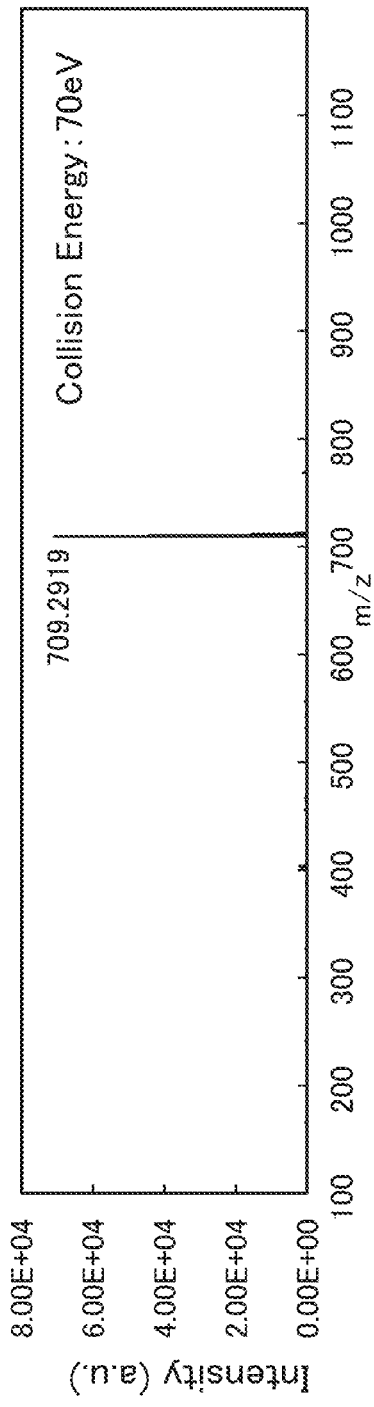
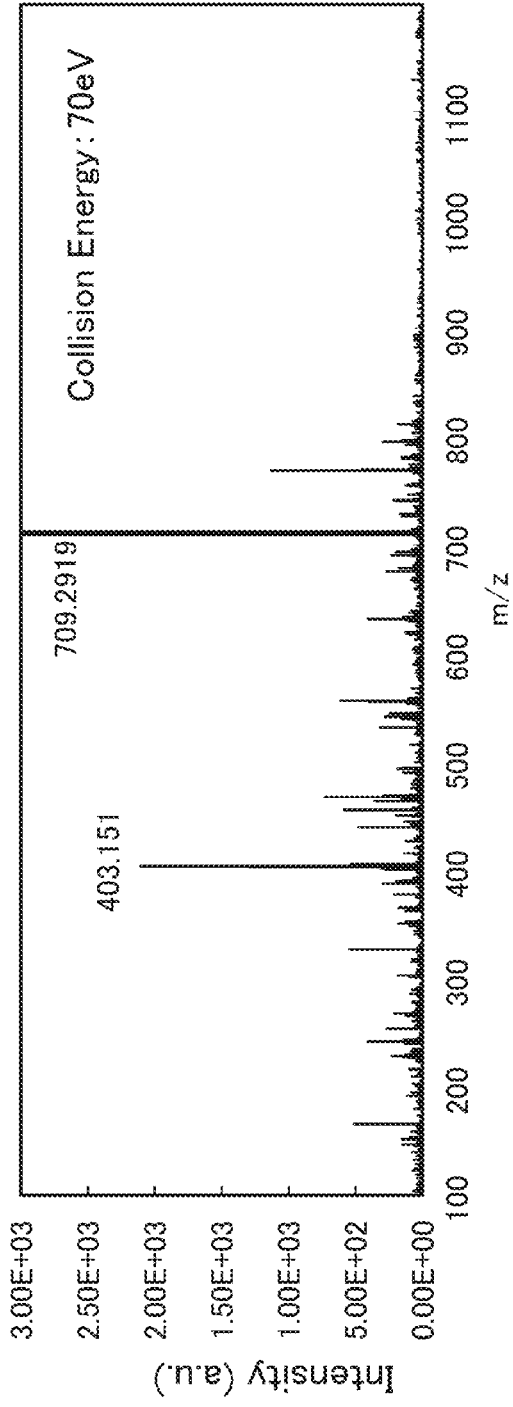
FIG. 9A
FIG. 9B

Spin density is distributed to nitrogen atom of carbazole

Spin density is distributed to entire part of carbazole

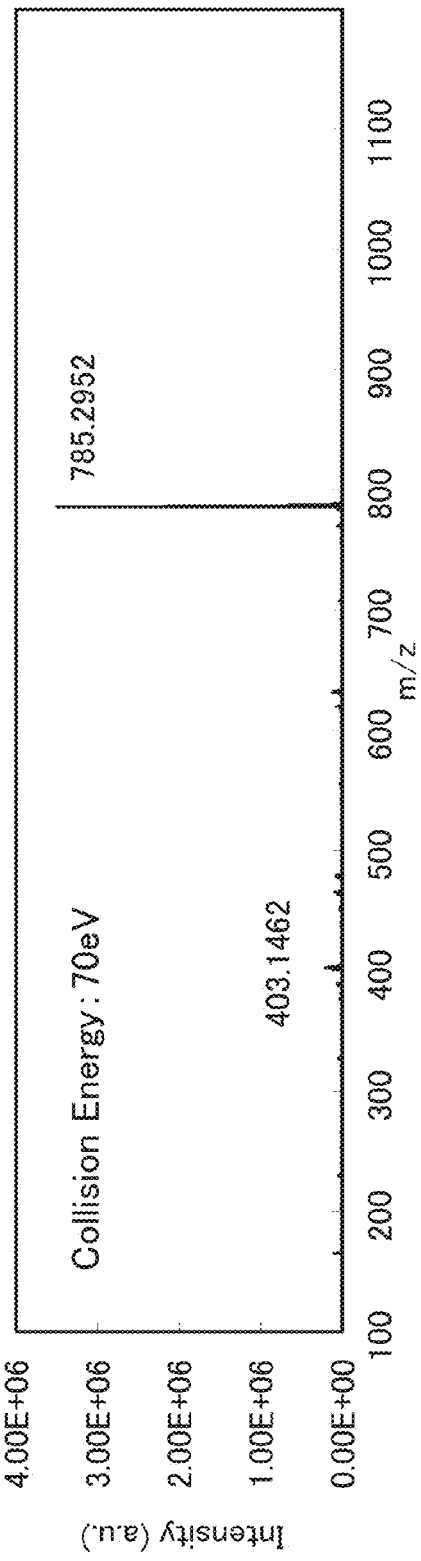
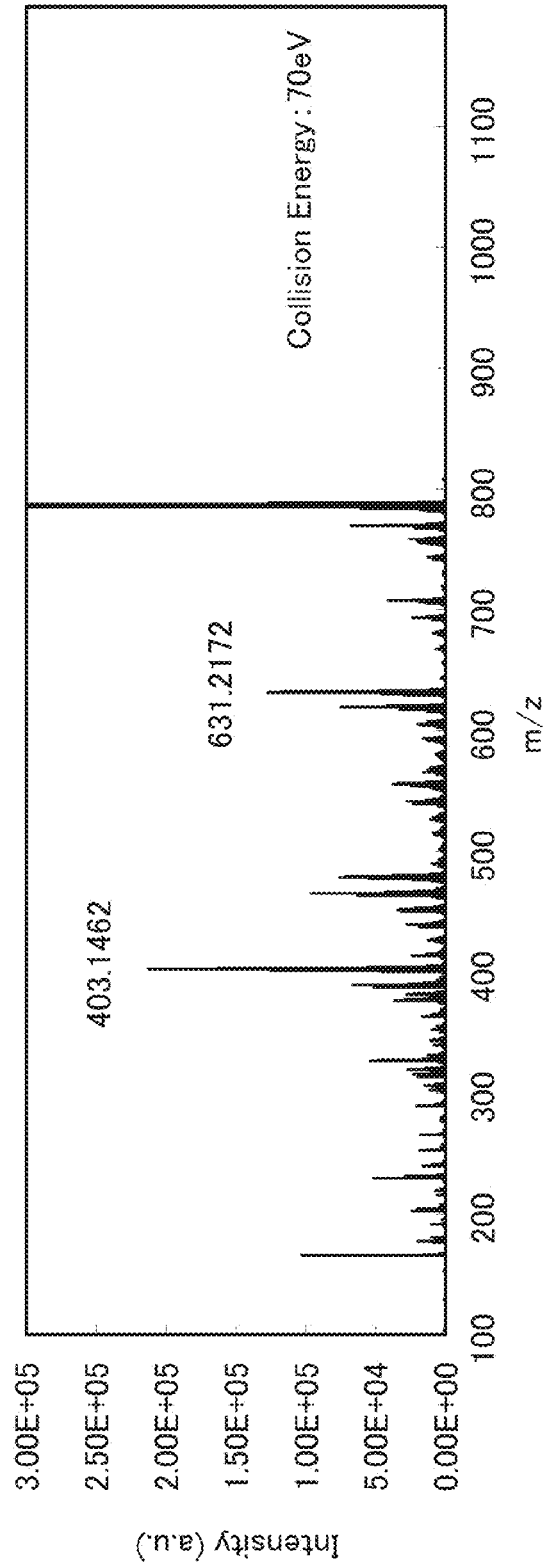

ANTHRACENE COMPOUND, LIGHT-EMITTING ELEMENT, LIGHT-EMITTING DEVICE, ELECTRONIC APPLIANCE, AND LIGHTING DEVICE

BACKGROUND OF THE INVENTION

1. Field of the Invention

The present invention relates to an anthracene compound and a light-emitting element containing the anthracene compound as a light-emitting substance. The present invention also relates to a light-emitting device, an electronic appliance, and a lighting device each of which includes the light-emitting element.

2. Description of the Related Art

In recent years, research and development have been extensively conducted on light-emitting elements utilizing electroluminescence (EL) (Patent Document 1 and Patent Document 2). In a basic structure of such a light-emitting element, a layer containing a light-emitting substance (a light-emitting layer) is provided between a pair of electrodes. By applying voltage to the element, light emission from the light-emitting substance can be obtained.

Such a light-emitting element is a self-luminous element; thus, a display (a display device) including the light-emitting element has advantages over a liquid crystal display in point of high visibility, no backlight required, and the like. Besides, such a light-emitting element has advantages in that it can be manufactured to be thin and lightweight and has very fast response speed.

Since a light-emitting layer of such a light-emitting element can be formed in the form of a film, planar light emission can be achieved. This feature is difficult to obtain with point light sources typified by incandescent lamps and LEDs or linear light sources typified by fluorescent lamps. Thus, the light-emitting element also has great potential as a planar light source applicable to a lighting device and the like.

In the case of an organic EL element in which a light-emitting layer containing an organic compound as a light-emitting substance is provided between a pair of electrodes, application of voltage between the pair of electrodes causes injection of electrons from a cathode and holes from an anode into the light-emitting layer, so that a current flows. By recombination of the injected electrons and holes, the light-emitting organic compound is brought into an excited state to provide light emission.

An organic EL element is known in which an electron-injection layer, a hole-injection layer, an electron-transport layer, and a hole-transport layer are provided between a cathode and an anode for efficient injection of electrons and holes to a light-emitting layer. In such an organic EL element, an anode, a hole-injection layer, a hole-transport layer, a light-emitting layer, an electron-transport layer, an electron-injection layer, and a cathode are generally stacked in this order.

It is known that a small amount of dopant material with high emission efficiency is dispersed in a host material in a light-emitting layer, so that the emission efficiency can be improved. In the light-emitting layer having such a structure, electrons and holes are recombined first in the host material, so that the host material is brought into an excited state. Then the excited energy is transferred to the dopant materials to excite the dopant materials, so that light emission from the dopant materials can be obtained. Such an energy transfer mechanism can improve the emission efficiency of a light-emitting element.

The excited state of an organic compound can be a singlet excited state or a triplet excited state, and light emission from the singlet excited state ($S_1$) is referred to as fluorescence, and light emission from the triplet excited state ($T_1$) is referred to as phosphorescence. The statistical generation ratio of the excited states in the light-emitting element is considered to be $S_1:T_1=1:3$. Therefore, a light-emitting element including a phosphorescent compound capable of converting the triplet excited state into light emission has been actively developed in recent years.

An element that emits light in the blue and green regions is most demanded of light-emitting elements containing phosphorescent compounds.

REFERENCES

Patent Documents

Patent Document 1: U.S. Pat. No. 6,984,462
Patent Document 2: Chinese Patent Application Publication No. 1338499

SUMMARY OF THE INVENTION

In a phosphorescent element, a compound having a triplet excited state ($T_1$) energy level higher than that of a phosphorescent dopant material needs to be used as a host material for a light-emitting layer. Therefore, a host material used in a light-emitting element emitting light in the blue and green regions needs to have a higher $T_1$ level than a host material used in a light-emitting element emitting light having a longer wavelength than light in the blue and green regions.

It is preferable that a light-emitting element have high heat resistance for a longer lifetime. A compound with a high glass-transition temperature (Tg) may be used in order to improve the heat resistance of a light-emitting element.

An object of one embodiment of the present invention is to provide an anthracene compound with a high $T_1$ level. Another object is to provide a light-emitting element that emits phosphorescence in the blue and green regions. Another object is to provide an anthracene compound with a high glass-transition temperature. Another object is to provide a light-emitting element, a light-emitting device, an electronic appliance, or a lighting device with high heat resistance.

One embodiment of the present invention is a light-emitting element that includes at least a hole-transport layer, a light-emitting layer, and an electron-transport layer between an anode and a cathode. The light-emitting layer contains an anthracene compound represented by General Formula (G1) and a phosphorescent compound. At least one of the hole-transport layer and the electron-transport layer contains the anthracene compound represented by General Formula (G1).

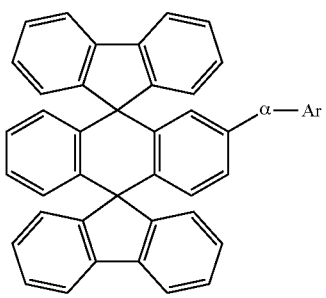

(G1)

In the formula, α represents a substituted or unsubstituted m-phenylene group or a substituted or unsubstituted 3,3'-biphenyldiyl group; and Ar represents any of a substituted or unsubstituted phenyl group, a substituted or unsubstituted biphenyl group, a substituted or unsubstituted carbazolyl group, a substituted or unsubstituted dibenzothiophenyl group, a substituted or unsubstituted dibenzofuranyl group, a substituted or unsubstituted triphenylenyl group, a substituted or unsubstituted naphthyl group, a substituted or unsubstituted phenanthrenyl group, a substituted or unsubstituted fluorenyl group, a substituted or unsubstituted pyridyl group, a substituted or unsubstituted pyrimidyl group, a substituted or unsubstituted dibenzoquinoxalinyl group, a substituted or unsubstituted benzimidazolyl group, and a substituted or unsubstituted benzoxazolyl group. In the case where a substituent is bonded to Ar, the substituent is any of a phenyl group, a biphenyl group, and an alkyl group having 1 to 6 carbon atoms.

Another embodiment of the present invention is a light-emitting element that includes at least a hole-transport layer, a light-emitting layer, and an electron-transport layer between an anode and a cathode. The electron-transport layer contains the anthracene compound represented by General Formula (G1) and an electron-transport organic compound.

Another embodiment of the present invention is a light-emitting element that includes at least a hole-transport layer, a light-emitting layer, and an electron-transport layer between an anode and a cathode. The hole-transport layer contains the anthracene compound represented by General Formula (G1) and a hole-transport organic compound.

Another embodiment of the present invention is a light-emitting element that includes at least a hole-transport layer, a light-emitting layer, and an electron-transport layer between an anode and a cathode. The light-emitting layer contains the anthracene compound represented by General Formula (G1) and a phosphorescent compound. The hole-transport layer contains the anthracene compound represented by General Formula (G1) and a hole-transport organic compound. The electron-transport layer contains the anthracene compound represented by General Formula (G1) and an electron-transport organic compound.

Another embodiment of the present invention is a light-emitting element that includes at least a hole-transport layer, a light-emitting layer, and an electron-transport layer between an anode and a cathode. The light-emitting layer contains an electron-transport compound or a hole-transport compound, the anthracene compound represented by General Formula (G1), and a phosphorescent compound. The hole-transport layer contains the anthracene compound represented by General Formula (G1) and a hole-transport organic compound. The electron-transport layer contains the anthracene compound represented by General Formula (G1) and an electron-transport organic compound.

In the above-described structure, a peak on the shortest wavelength side of phosphorescence can be 570 nm or less.

Another embodiment of the present invention is a compound represented by Structural Formula (100).

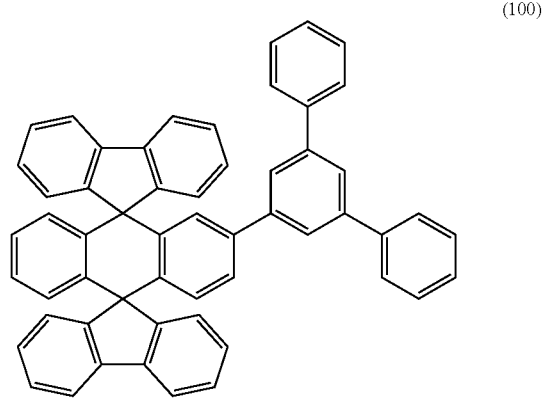 [SMILES: c1ccc(-c2cc(-c3ccccc3)cc(-c3ccc4c(c3)C3(c5ccccc5-c5ccccc53)c3ccccc3C43c4ccccc4-c4ccccc43)c2)cc1]

Another embodiment of the present invention is a compound represented by Structural Formula (103).

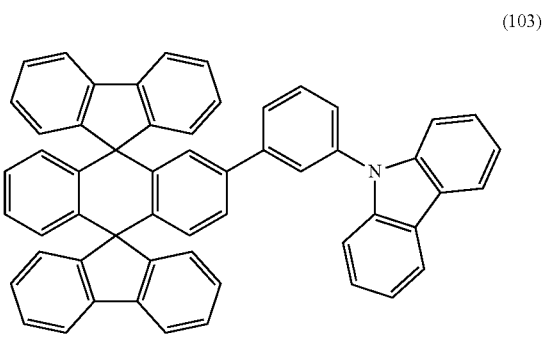 [SMILES: c1cc(-c2ccc3c(c2)C2(c4ccccc4-c4ccccc42)c2ccccc2C32c3ccccc3-c3ccccc32)cc(-n2c3ccccc3c3ccccc32)c1]

Another embodiment of the present invention is a compound represented by Structural Formula (112).

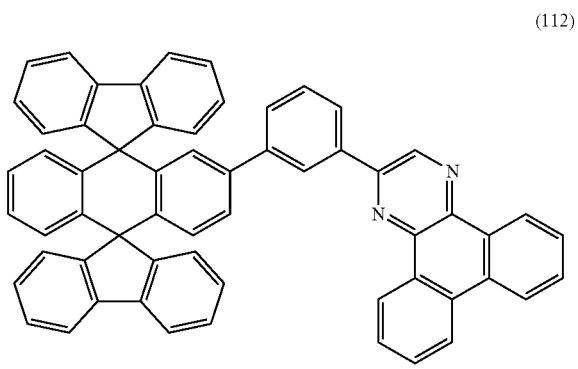 [SMILES: c1cc(-c2ccc3c(c2)C2(c4ccccc4-c4ccccc42)c2ccccc2C32c3ccccc3-c3ccccc32)cc(-c2cnc3c4ccccc4c4ccccc4c3n2)c1]

According to one embodiment of the present invention, a compound with a high $T_1$ level can be provided. In addition, a light-emitting element that emits phosphorescence in the blue and green regions can be provided. In addition, a compound with a high glass-transition temperature (Tg) can be provided. In addition, a light-emitting element, a light-emitting device, an electronic appliance, or a lighting device with high heat resistance can be provided.

BRIEF DESCRIPTION OF THE DRAWINGS

FIGS. 5A to 5E illustrate examples of electronic appliances.

FIGS. 9A and 9B show results of LC/MS analysis of the anthracene compound (2mTPDfha) represented by Structural Formula (100).

FIGS. 37A and 37B show results of LC/MS analysis of an anthracene compound (2mDBqPDfha) represented by Structural Formula (112).

DETAILED DESCRIPTION OF THE INVENTION

Hereinafter, embodiments and examples of the present invention will be described in detail with reference to the accompanying drawings. Note that the present invention is not limited to the following description, and various changes and modifications can be made without departing from the spirit and scope of the present invention. Therefore, the present invention should not be construed as being limited to the description in the following embodiments and examples.

Embodiment 1

In this embodiment, light-emitting elements each of which is one embodiment of the present invention are described with reference to FIG. 1, FIGS. 2A to 2D, and FIG. 3.

Figure 1:
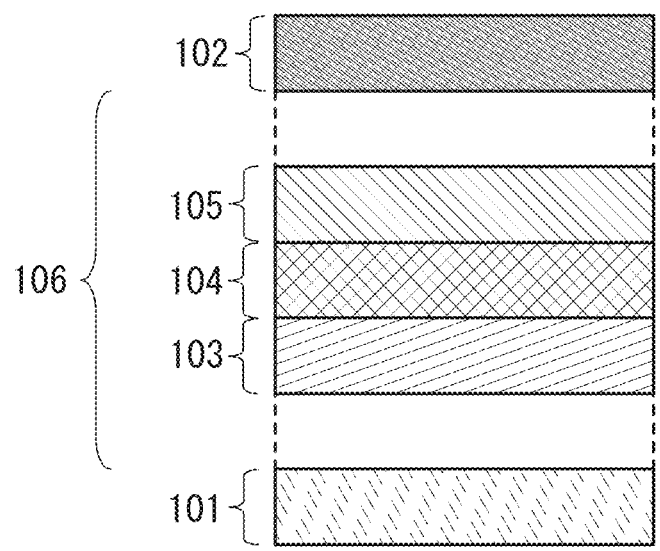
FIG. 1 illustrates an example of a light-emitting element of one embodiment of the present invention.

As illustrated in FIG. 1, the light-emitting element of one embodiment of the present invention includes an anode 101, a hole-transport layer 103 over the anode 101, a light-emitting layer 104 on and in contact with the hole-transport layer 103, an electron-transport layer 105 on and in contact with the light-emitting layer 104, and a cathode 102 over the electron-transport layer 105. When voltage higher than the threshold voltage of the light-emitting element is applied between the anode 101 and the cathode 102, holes are injected from the anode 101 side and electrons are injected from the cathode 102 side to an EL layer 106 including at least the hole-transport layer 103, the light-emitting layer 104, and the electron-transport layer 105. The injected electrons and holes are recombined in the EL layer 106 and a light-emitting substance contained in the EL layer 106 emits light.

The light-emitting element of one embodiment of the present invention is a light-emitting element that includes at least the hole-transport layer 103, the light-emitting layer 104, and the electron-transport layer 105 between the anode 101 and the cathode 102. In the light-emitting element, an anthracene compound represented by General Formula (G1) is contained in at least one of the light-emitting layer 104, the hole-transport layer 103, and the electron-transport layer 105.

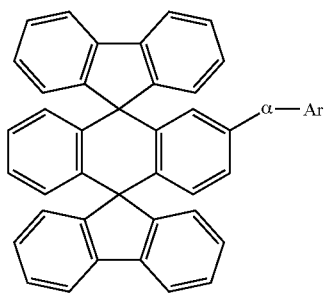

(G1)

In the formula, α represents a m-phenylene group or a 3,3'-biphenyldiyl group; and Ar represents any of a substituted or unsubstituted phenyl group, a substituted or unsubstituted biphenyl group, a substituted or unsubstituted carbazolyl group, a substituted or unsubstituted dibenzothiophenyl group, a substituted or unsubstituted dibenzofuranyl group, a substituted or unsubstituted triphenylenyl group, a substituted or unsubstituted naphthyl group, a substituted or unsubstituted phenanthrenyl group, a substituted or unsubstituted fluorenyl group, a substituted or unsubstituted pyridyl group, a substituted or unsubstituted pyrimidyl group, a substituted or unsubstituted dibenzoquinoxalinyl group, a substituted or unsubstituted benzimidazolyl group, and a substituted or unsubstituted benzoxazolyl group.

In the case where a substituent is bonded to Ar, the substituent is a phenyl group, a biphenyl group, or an alkyl group having 1 to 6 carbon atoms. Such a substituent is preferably used, in which case the structure becomes sterical; thus, a film including such a substituent is not easily crystallized and uniform film quality is easily obtained. An aryl group is preferably used as the substituent, in which case heat resistance is improved. The biphenyl group is more preferably a meta-biphenyl group or an ortho-biphenyl group than a para-biphenyl group, in which case the $T_1$ level is not easily reduced. The alkyl group is preferably used as the substituent, in which case solubility in an organic solvent is increased. The alkyl group is preferably used as the substituent, in which case the $T_1$ level is not easily reduced. It is preferable that such a substituent be not used, in which case the $T_1$ level is not easily reduced and can be kept high.

In the case where the anthracene compound represented by General Formula (G1) is used as a host material for a blue phosphorescent dopant material, a substituted or unsubstituted phenyl group, a substituted or unsubstituted biphenyl group, a substituted or unsubstituted carbazolyl group, a substituted or unsubstituted dibenzothiophenyl group, a substituted or unsubstituted dibenzofuranyl group, a substituted or unsubstituted fluorenyl group, a substituted or unsubstituted pyridyl group, a substituted or unsubstituted pyrimidyl group, a substituted or unsubstituted benzimidazolyl group, and a substituted or unsubstituted benzoxazolyl group are particularly preferable because of their higher $T_1$ levels. Furthermore, a substituted or unsubstituted phenyl group, a substituted or unsubstituted biphenyl group, and a substituted or unsubstituted carbazol-9-yl group are more preferable because of their high $T_1$ levels.

A compound with a high molecular weight generally has a high glass-transition temperature (Tg). However, such a compound with a high molecular weight has conjugation that extends easily and an $S_1$ and $T_1$ levels that are reduced easily. Meanwhile, the anthracene compound represented by General Formula (G1) has a high molecular weight and high Tg but has a high $S_1$ and $T_1$ levels. The reason for the high Tg is probably as follows: planes of two fluorene skeletons are orthogonally bonded to the 9-position and the 9'-position of an anthracene skeleton at approximately 90°, which provides high three dimensionality. For this reason, the anthracene compound is preferably mixed with a material that is crystallized easily, in which case film quality is improved. The reason for the high $S_1$ and $T_1$ levels is thought to be as follows: the 9-position and the 9'-position of the anthracene skeleton each have a carbon-carbon sigma bond, which suppresses extension of the conjugation between the anthracene skeleton and the fluorene skeleton bonded thereto. In addition, another reason is thought to be as follows: this sigma bond prevents conjugation from a substituent (α-Ar) bonded to the 2-position of the anthracene skeleton from extending beyond a benzene skeleton including the 2-position of the anthracene skeleton. The $S_1$ and $T_1$ levels are high for the above-described reason, and a gap between the highest occupied molecular orbital (HOMO) level and the lowest unoccupied molecular orbital (LUMO) level is large. Thus, the anthracene compound is preferably contained in a carrier-transport layer, in which case a carrier-blocking property and an exciton-blocking property are improved. Owing to the high $S_1$ and $T_1$ levels, the anthracene compound can be suitably used for a light-emitting layer in a light-emitting element emitting light with a short wavelength such as light in the blue or green region.

Since Ar is bonded to the anthracene skeleton via m-phenylene represented by α in the anthracene compound represented by General Formula (G1), extension of the conjugation can be suppressed more than in the case where Ar is bonded to the anthracene skeleton via p-phenylene. Thus, the anthracene compound has a high $T_1$ level.

For this reason, the anthracene compound represented by General Formula (G1) can be suitably used as a host material for the light-emitting layer 104 in a light-emitting element emitting light with short wavelengths in the visible range such as phosphorescence in the blue and green regions. In addition, the anthracene compound represented by General Formula (G1) is contained in at least one of the light-emitting layer 104, the hole-transport layer 103, and the electron-transport layer 105, so that a light-emitting element with high heat resistance can be obtained.

The anthracene compound represented by General Formula (G1) can also be suitably mixed with other compounds contained in the light-emitting layer 104, the hole-transport layer 103, and the electron-transport layer 105.

Figure 2A:
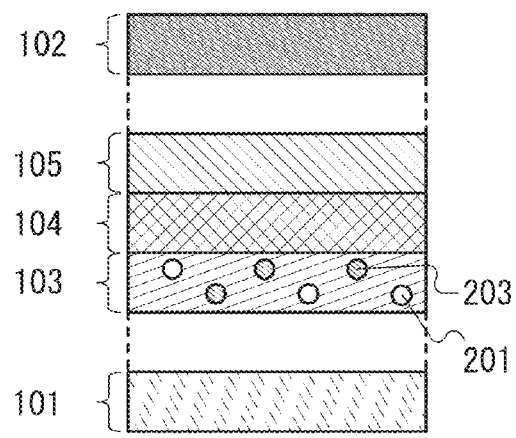
FIGS. 2A to 2D each illustrate an example of a light-emitting element of one embodiment of the present invention.

For example, as illustrated in FIG. 2A, the hole-transport layer 103 may contain an anthracene compound 201 represented by General Formula (G1) and a hole-transport compound 203. In this case, Ar in General Formula (G1) representing the anthracene compound is preferably any of a substituted or unsubstituted biphenyl group, a substituted or unsubstituted carbazolyl group, a substituted or unsubstituted dibenzothiophenyl group, a substituted or unsubstituted dibenzofuranyl group, a substituted or unsubstituted triphenylenyl group, a substituted or unsubstituted naphthyl group, a substituted or unsubstituted phenanthrenyl group, and a substituted or unsubstituted fluorenyl group, in which case the hole-transport property is high.

Figure 2B:
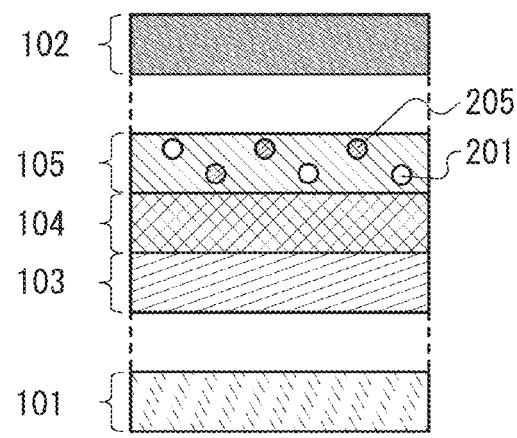

As illustrated in FIG. 2B, the electron-transport layer 105 may contain the anthracene compound 201 represented by General Formula (G1) and an electron-transport compound 205. In this case, Ar in General Formula (G1) representing the anthracene compound is preferably any of a substituted or unsubstituted pyridyl group, a substituted or unsubstituted pyrimidyl group, a substituted or unsubstituted dibenzoquinoxalinyl group, a substituted or unsubstituted benzimidazolyl group, and a substituted or unsubstituted benzoxazolyl group.

Figure 2C:
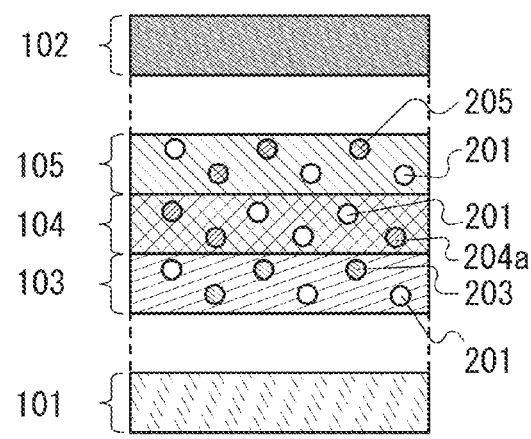

As illustrated in FIG. 2C, the light-emitting layer 104 may contain the anthracene compound 201 represented by General Formula (G1) and a phosphorescent compound 204a, the hole-transport layer 103 may contain the anthracene compound 201 represented by General Formula (G1) and the hole-transport compound 203, and the electron-transport layer 105 may contain the anthracene compound 201 represented by General Formula (G1) and the electron-transport compound 205.

Figure 2D:
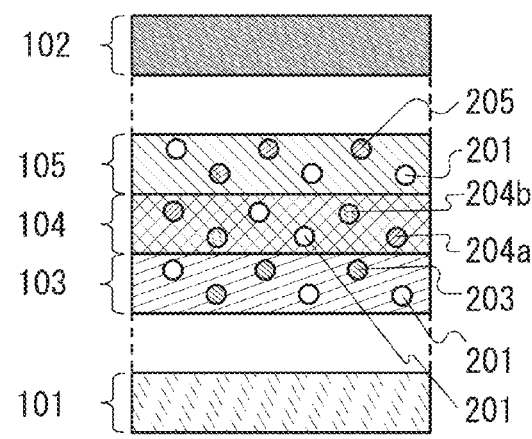

As illustrated in FIG. 2D, the light-emitting layer 104 may contain the anthracene compound 201 represented by General Formula (G1), the phosphorescent compound 204a, and an electron-transport or hole-transport compound 204b, the hole-transport layer 103 may contain the anthracene compound 201 represented by General Formula (G1) and the hole-transport compound 203, and the electron-transport layer 105 may contain the anthracene compound 201 represented by General Formula (G1) and the electron-transport compound 205.

Figure 3:
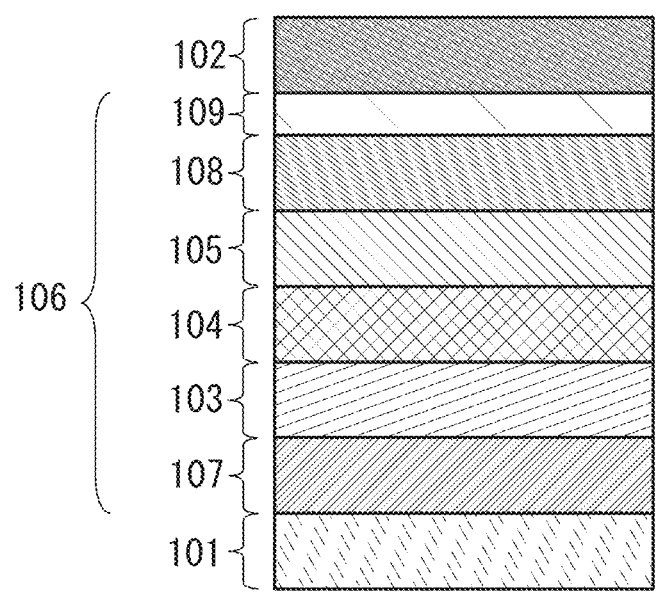
FIG. 3 illustrates an example of a light-emitting element of one embodiment of the present invention.

As illustrated in FIG. 3, a hole-injection layer 107 may be provided between the anode 101 and the hole-transport layer 103. In addition, an electron-injection layer 108 may be provided between the cathode 102 and the electron-transport layer 105. In addition, a charge-generation layer 109 may be provided between the cathode 102 and the electron-injection layer 108.

The hole-injection layer 107 contains a substance having a high hole-transport property and an acceptor substance. When electrons are extracted from the substance having a high hole-transport property owing to the acceptor substance, holes are generated. Thus, holes are injected from the hole-injection layer 107 into the light-emitting layer 104 through the hole-transport layer 103. The anthracene compound represented by General Formula (G1) may be used as the substance having a high hole-transport property. In this case, Ar in General Formula (G1) representing the anthracene compound is preferably any of a substituted or unsubstituted biphenyl group, a substituted or unsubstituted carbazolyl group, a substituted or unsubstituted dibenzothiophenyl group, a substituted or unsubstituted dibenzofuranyl group, a substituted or unsubstituted triphenylenyl group, a substituted or unsubstituted naphthyl group, a substituted or unsubstituted phenanthrenyl group, and a substituted or unsubstituted fluorenyl group, in which case the hole-transport property is high.

The charge-generation layer 109 contains a substance having a high hole-transport property and an acceptor substance. Electrons are extracted from the substance having a high hole-transport property owing to the acceptor substance, and the extracted electrons are injected from the electron-injection layer 108 having an electron-injection property into the light-emitting layer 104 through the electron-transport layer 105.

Specific examples of the anthracene compound represented by General Formula (G1) include anthracene compounds represented by Structural Formulae 100 to 112. However, the present invention is not limited thereto.

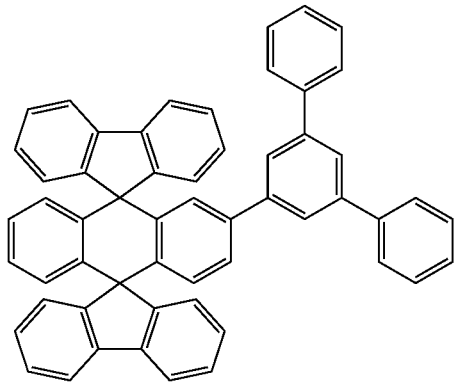

(100)

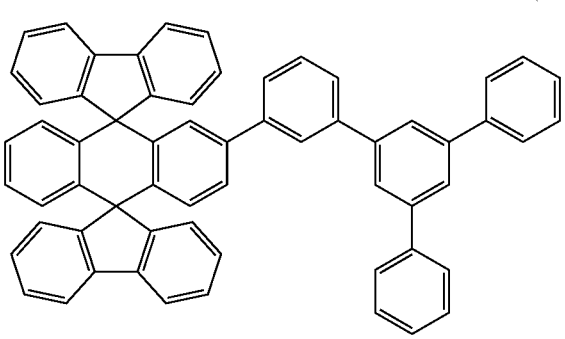

(101)

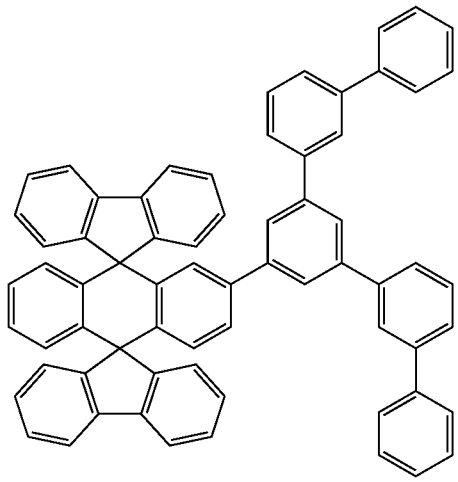

(102)

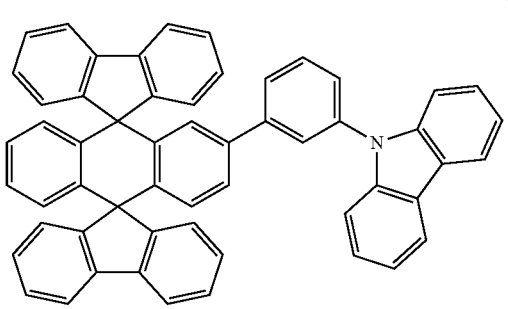

(103)

(104)
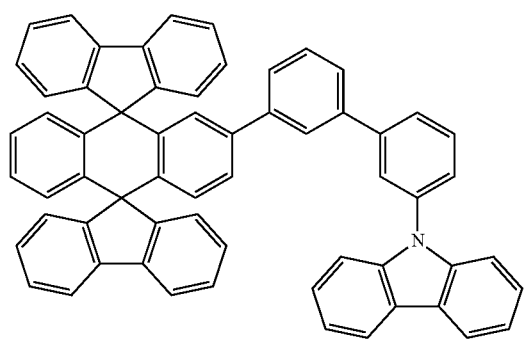
(105)
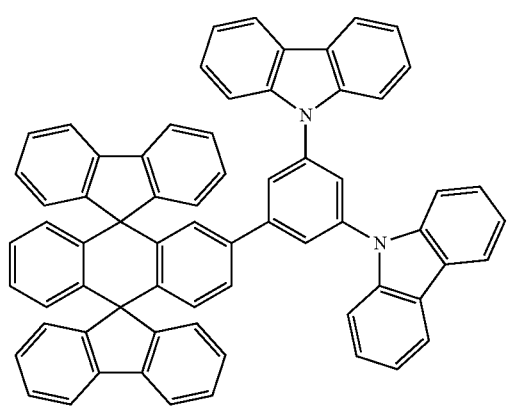
(106)
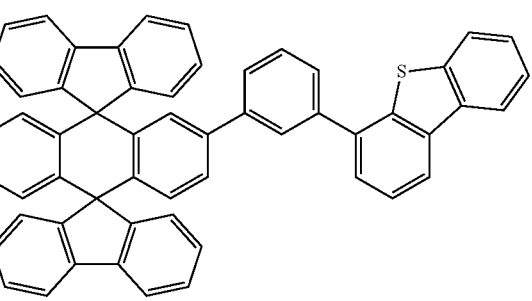
(107)
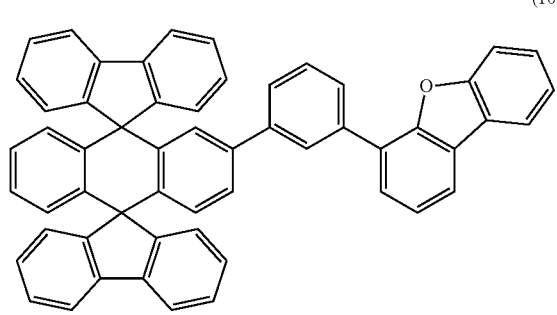
(108)
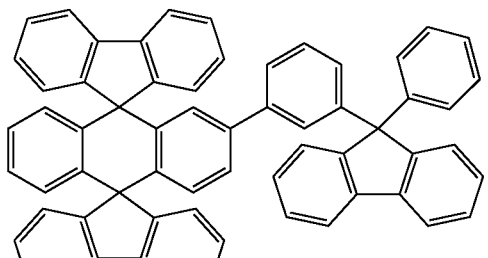
(109)
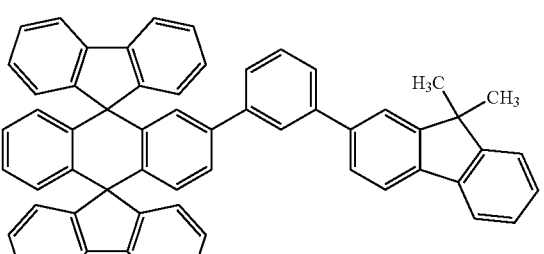
(110)
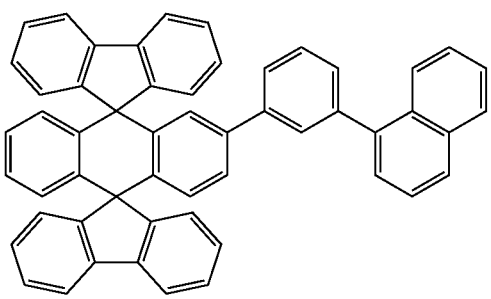
(111)
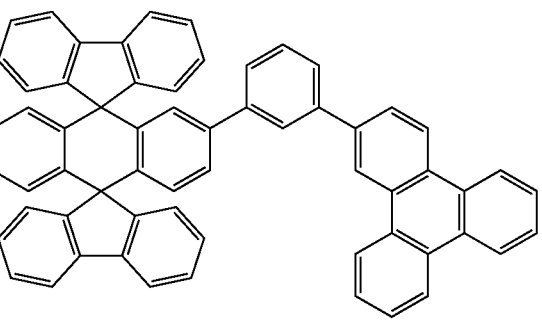
(112)
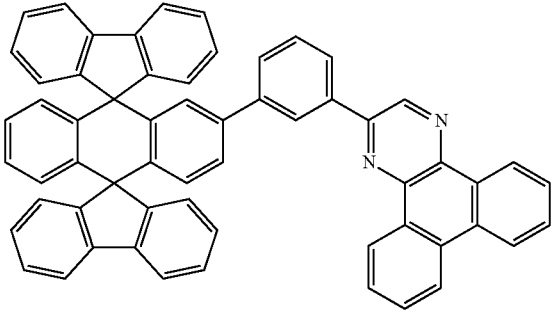

An example of a method for synthesizing the anthracene compound represented by General Formula (G1) is described below. Note that the method for synthesizing the anthracene compound represented by General Formula (G1) is not limited to the method described below.

<<Method for synthesizing Anthracene Compound Represented by General Formula (G1)>>

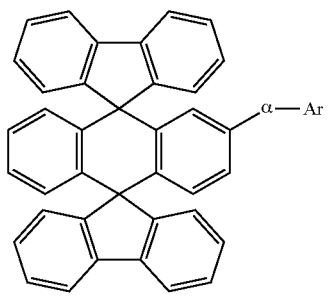

(G1)

In the formula, α represents a m-phenylene group or a 3,3'-biphenyldiyl group; and Ar represents any of a substituted or unsubstituted phenyl group, a substituted or unsubstituted biphenyl group, a substituted or unsubstituted carbazolyl group, a substituted or unsubstituted dibenzothiophenyl group, a substituted or unsubstituted dibenzofuranyl group, a substituted or unsubstituted triphenylenyl group, a substituted or unsubstituted naphthyl group, a substituted or unsubstituted phenanthrenyl group, a substituted or unsubstituted fluorenyl group, a substituted or unsubstituted pyridyl group, a substituted or unsubstituted pyrimidyl group, a substituted or unsubstituted dibenzoquinoxalinyl group, a substituted or unsubstituted benzimidazolyl group, and a substituted or unsubstituted benzoxazolyl group. In the case where a substituent is bonded to Ar, the substituent is a phenyl group, a biphenyl group, or an alkyl group having 1 to 6 carbon atoms.

Synthesis Scheme (g) of the anthracene compound represented by General Formula (G1) is shown below.

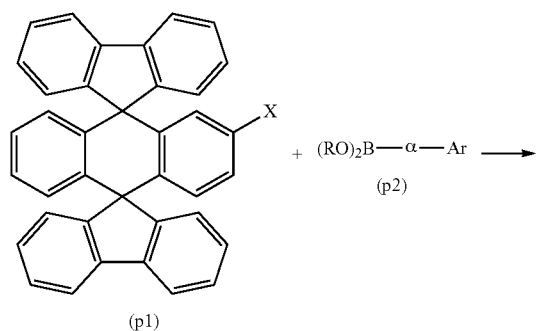

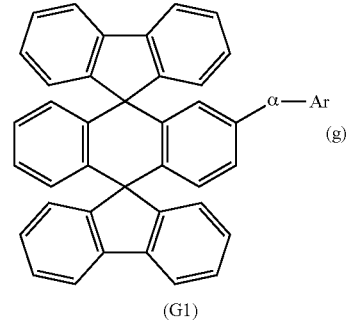

(G1)

In Synthesis Scheme (g), α represents a m-phenylene group or a 3,3'-biphenyldiyl group; and Ar represents any of a substituted or unsubstituted phenyl group, a substituted or unsubstituted biphenyl group, a substituted or unsubstituted carbazolyl group, a substituted or unsubstituted dibenzothiophenyl group, a substituted or unsubstituted dibenzofuranyl group, a substituted or unsubstituted triphenylenyl group, a substituted or unsubstituted naphthyl group, a substituted or unsubstituted phenanthrenyl group, a substituted or unsubstituted fluorenyl group, a substituted or unsubstituted pyridyl group, a substituted or unsubstituted pyrimidyl group, a substituted or unsubstituted dibenzoquinoxalinyl group, a substituted or unsubstituted benzimidazolyl group, and a substituted or unsubstituted benzoxazolyl group. In the case where a substituent is bonded to Ar, the substituent is a phenyl group, a biphenyl group, or an alkyl group having 1 to 6 carbon atoms. In addition, X represents halogen; bromine or iodine is preferable because of its high reactivity. In addition, R represents an alkyl group or hydrogen.

As shown in Synthesis Scheme (g), an anthracene halide (Compound (p1)) is coupled with an aryl boron compound or aryl boronic acid (Compound (p2)) by the Suzuki-Miyaura coupling, so that the anthracene compound represented by General Formula (G1) can be obtained.

Examples of palladium catalysts that can be used in Synthesis Scheme (g) include, but are not limited to, palladium(II) acetate, tetrakis(triphenylphosphine)palladium(0), and bis(triphenylphosphine)palladium(II) dichloride.

Examples of ligands of the palladium catalyst that can be used in Synthesis Scheme (g) include, but are not limited to, tri(ortho-tolyl)phosphine, triphenylphosphine, and tricyclohexylphosphine.

Examples of bases that can be used in Synthesis Scheme (g) include, but are not limited to, an organic base such as sodium tert-butoxide and an inorganic base such as potassium carbonate or sodium carbonate.

Examples of a solvent that can be used in the synthesis scheme (g) include, but not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; and a mixed solvent of water and an ether such as ethylene glycol dimethyl ether. Note that a mixed solvent of toluene and water; a mixed solvent of toluene, ethanol, and water; or a mixed solvent of water and ether such as ethylene glycol dimethyl ether is more preferable.

As the coupling reaction in Synthesis Scheme (g), the Suzuki-Miyaura coupling using the organoboron compound or the boronic acid represented by Compound (p2) may be replaced with a cross coupling reaction using an organoaluminum compound, an organozirconium compound, an organozinc compound, an organotin compound, or the like. However, the present invention is not limited thereto.

In Synthesis Scheme (g), a boron compound of anthracene or a boronic acid compound of anthracene may be coupled with a halogenated aryl compound or aryl triflate by the Suzuki-Miyaura coupling.

In the above-described manner, the anthracene compound represented by General Formula (G1) can be synthesized.

A specific example in which the light-emitting element described in this embodiment is manufactured is described below.

For the anode 101 and the cathode 102, any of metals, alloys, electrically conductive compounds, and mixtures thereof, and the like can be used. Specifically, indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), an alkaline earth metal such as calcium (Ca) or strontium (Sr), or magnesium (Mg), an alloy containing such an element (MgAg, AlLi), a rare earth metal such as europium (Eu) or ytterbium (Yb), an alloy containing such an element, graphene, and the like can be used. Note that the anode 101 and the cathode 102 can be formed by, for example, a sputtering method or an evaporation method (including a vacuum evaporation method).

Examples of the substance having a high hole-transport property that is used for the hole-injection layer 107, the hole-transport layer 103, and the charge-generation layer 109 include aromatic amine compounds such as 4,4'-bis[N-(1-naphthyl)-N-phenylamino]biphenyl (abbreviation: NPB or α-NPD), N,N-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); and 3-[N-(1-naphthyl)-N-(9-phenylcarbazol-3-yl)amino]-9-phenylcarbazole (abbreviation: PCzPCN1). A carbazole compound, such as 4,4'-di(N-carbazolyl)biphenyl (abbreviation: CBP), 1,3,5-tris[4-(N-carbazolyl)phenyl]benzene (abbreviation: TCPB), or 9-[4-(10-phenyl-9-anthracenyl)phenyl]-9H-carbazole (abbreviation: CzPA), or the like can also be used. These materials given here are mainly substances having a hole mobility of $10^{-6}$ cm$^2$/Vs or higher. Note that any other substances may also be used as long as the substances have hole-transport properties higher than electron-transport properties.

Further, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can be used.

Note that the anthracene compound represented by General Formula (G1) can also be used as the substance having a high hole-transport property.

Examples of the acceptor substance that is used for the hole-injection layer 107 and the charge-generation layer 109 include a transition metal oxide and an oxide of a metal belonging to any of Groups 4 to 8 of the periodic table. Specifically, molybdenum oxide is particularly preferable.

The light-emitting layer 104 contains a light-emitting substance. The light-emitting layer 104 may contain only a light-emitting substance; alternatively, an emission center substance may be dispersed in a host material in the light-emitting layer 104. Alternatively, a mixture of two or more kinds of host materials may be used.

There is no particular limitation on the material that can be used as the light-emitting substance and the emission center substance in the light-emitting layer 104, and light emitted from the substance may be either fluorescence or phosphorescence. Given below are examples of the light-emitting substance and the emission center substance.

As the substance emitting fluorescence, known materials can be used. The anthracene compound represented by General Formula (G1) may also be used.

Examples of the substance that emits phosphorescence include bis[2-(3',5'-bistrifluoromethylphenyl)pyridinato-N,C$^{2'}$]iridium(III)picolinate (abbreviation: [Ir(CF$_3$ppy)$_2$(pic)]), bis[2-(4',6'-difluorophenyl)pyridinato-N,C$^{2'}$]iridium (III)acetylacetonate (abbreviation: FIracac), tris(2-phenylpyridinato)iridium(III) (abbreviation: [Ir(ppy)$_3$]), bis(2-phenylpyridinato)iridium(III)acetylacetonate (abbreviation: [Ir(ppy)$_2$(acac)]), tris(acetylacetonato)(monophenanthroline)terbium(III) (abbreviation: Tb(acac)$_3$(Phen)), bis(benzo[h]quinolinato)iridium(III)acetylacetonate (abbreviation: [Ir(bzq)$_2$(acac)]), bis(2,4-diphenyl-1,3-oxazolato-N,C$^{2'}$)iridium(III)acetylacetonate (abbreviation: [Ir(dpo)$_2$(acac)]), bis[2-(4'-perfluorophenylphenyl)pyridinato]iridium(III) acetylacetonate (abbreviation: [Ir(p-PF-ph)$_2$(acac)]), bis(2-phenylbenzothiazolato-N,C$^{2'}$)iridium(III)acetylacetonate (abbreviation: [Ir(bt)$_2$(acac)]), bis[2-(T-benzo[4,5-α]thienyl)pyridinato-N, C$^{3'}$]iridium(III)acetylacetonate (abbreviation: [Ir(btp)$_2$(acac)]), bis(1-phenylisoquinolinato-N,C$^{2'}$)iridium(III)acetylacetonate (abbreviation: [Ir(piq)$_2$(acac)]), (acetylacetonato)bis[2,3-bis(4-fluorophenyl)quinoxalinato]iridium(III) (abbreviation: [Ir(Fdpq)$_2$(acac)]), (acetylacetonato)bis(2,3,5-triphenylpyrazinato)iridium(III) (abbreviation: [Ir(tppr)$_2$(acac)]), 2,3,7,8,12,13,17,18-octaethyl-21H,23H-porphyrin platinum(II) (abbreviation: PtOEP), tris(1,3-diphenyl-1,3-propanedionato)(monophenanthroline)europium(III) (abbreviation: [Eu(DBM)$_3$(Phen)]), and tris[1-(2-thenoyl)-3,3,3-trifluoroacetonato](monophenanthroline)europium(III) (abbreviation: [Eu(TTA)$_3$(Phen)]).

There is no particular limitation on the material that can be used as the above-described host material. Examples of the material include example: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl- 5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spiro-9,9'-bifluoren-2-yl)-N-phenylamino] biphenyl (abbreviation: BSPB). In addition, condensed polycyclic aromatic compounds such as anthracene derivatives, phenanthrene derivatives, pyrene derivatives, chrysene derivatives, and dibenzo[g,p]chrysene derivatives can be given, and specific examples are 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N'',N'',N''',N'''-octaphenyldibenzo[gp]chrysene-2,7,10,15-tetramine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl) anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), and 3,3',3''-(benzene-1,3,5-triyl)tripyrene (abbreviation: TPB3). One or more substances having a wider energy gap than the above-described emission center substance described above is preferably selected from these substances and known substances. Moreover, in the case where the emission center substance emits phosphorescence, a substance having higher triplet excitation energy (an energy difference between a ground state and a triplet excited state) than the emission center substance may be selected as the host material.

As the material that can be used as the host material, the anthracene compound represented by General Formula (G1) can also be used. The anthracene compound represented by General Formula (G1) has a high $T_1$ level. Thus, by using the anthracene compound as the host material for a phosphorescent substance, a light-emitting element emitting light in the blue and green regions can be achieved.

Note that the light-emitting layer 104 may have a structure in which two or more layers are stacked. For example, in the case where the light-emitting layer 104 is formed by stacking a first light-emitting layer and a second light-emitting layer in that order over the hole-transport layer, a substance having a hole-transport property is used as the host material for the first light-emitting layer and a substance having an electron-transport property is used as the host material for the second light-emitting layer.

The electron-transport layer 105 contains a substance having a high electron-transport property. For the electron-transport layer 105, a metal complex such as Alq$_a$, tris(4-methyl-8-quinolinolato)aluminum(III) (abbreviation: Almq$_3$), bis(10-hydroxybenzo[h]quinolinato)beryllium(II) (abbreviation: BeBq$_2$), BAlq, Zn(BOX)$_2$, or bis[2-(2-hydroxyphenyl)benzothiazolato]zinc(II) (abbreviation: Zn(BTZ)$_2$) can be used. A heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl) stilbene (abbreviation: BzOs) can also be used. A high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can also be used. The substances given here are mainly substances having an electron mobility of $10^{-6}$ cm$^2$/Vs or higher. Note that any other substances may also be used as long as the substances have electron-transport properties higher than hole-transport properties.

Note that the anthracene compound represented by General Formula (G1) can also be used as the substance having a high electron-transport property.

The electron-transport layer is not limited to a single layer, and may be a stack of two or more layers containing any of the above substances.

The electron-injection layer 108 contains a substance having a high electron-injection property. For the electron-injection layer 108, an alkali metal, an alkaline earth metal, or a compound thereof such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. Any of the above substances for forming the electron-transport layer 105 can also be used.

A composite material in which an organic compound and an electron donor are mixed may also be used for the electron-injection layer 108. Such a composite material has an excellent electron-injection and electron-transport properties because electrons are generated in the organic compound by the electron donor. In this case, the organic compound is preferably a material that is excellent in transporting the generated electrons. Specifically, for example, any of the above substances for forming the electron-transport layer 105 (e.g., a metal complex or a heteroaromatic compound) can be used. As the electron donor, a substance exhibiting an electron-donating property with respect to the organic compound may be used. Specifically, an alkali metal, an alkaline earth metal, and a rare earth metal are preferable, and examples thereof as lithium, cesium, magnesium, calcium, erbium, and ytterbium. In addition, an alkali metal oxide or an alkaline earth metal oxide is preferable, and examples thereof are lithium oxide, calcium oxide, and barium oxide. A Lewis base such as magnesium oxide can also be used. An organic compound such as tetrathiafulvalene (abbreviation: TTF) can also be used.

Note that each of the above-described hole-injection layer 107, hole-transport layer 103, light-emitting layer 104, electron-transport layer 105, electron-injection layer 108, and charge-generation layer 109 can be formed by a method such as an evaporation method (e.g., a vacuum evaporation method), an ink-jet method, or a coating method.

In the above-described light-emitting element, current flows because of a potential difference generated between the anode 101 and the cathode 102 and holes and electrons are recombined in the EL layer 106, so that light can be emitted. Then, the emitted light is extracted outside through one or both of the anode 101 and the cathode 102. Therefore, one or both of the anode 101 and the cathode 102 are electrodes having light-transmitting properties.

In the above-described light-emitting element, the anthracene compound represented by General Formula (G1) is contained in at least one of the hole-transport layer 103, the light-emitting layer 104, and the electron-transport layer 105; thus, the above-described light-emitting element can have high heat resistance.

Note that the light-emitting element described in this embodiment is an example of a light-emitting element manufactured using the anthracene compound that is one embodiment of the present invention. Further, as a light-emitting device including the above-described light-emitting element, a passive matrix light-emitting device and an active matrix light-emitting device can be manufactured. It is also possible to manufacture a light-emitting device with a microcavity structure including a light-emitting element described in another embodiment, which is different from the above-described light-emitting elements. Each of the above-described light-emitting devices is included in the present invention. Note that the above-described light-emitting devices can have improved heat resistance.

Note that there is no particular limitation on the structure of a TFT in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type TFT. Furthermore, a semiconductor film used for the TFT is not particularly limited. For example, a silicon film and an oxide semiconductor film can be used. In addition, the crystallinity of the semiconductor film is not particularly limited. For example, an amorphous semiconductor film and a semiconductor film with crystallinity can be used.

Note that the anthracene compound that is one embodiment of the present invention can be used for an organic thin-film solar cell. Specifically, the anthracene compound can be used in a carrier-transport layer or a carrier-injection layer because the anthracene compound has a carrier-transport property. In addition, a film of a mixture of the anthracene compound and an acceptor substance can be used as a charge-generation layer. In addition, the anthracene compound can be used for a power-generation layer because the anthracene compound is photoexcited.

Note that the structure described in this embodiment can be used as appropriate in combination with any of the structures described in the other embodiments.

Embodiment 2

In this embodiment, as one embodiment of the present invention, a light-emitting element (hereinafter referred to as tandem light-emitting element) in which a charge-generation layer is provided between a plurality of EL layers is described with reference to FIGS. 4A and 4B.

Figure 4A:
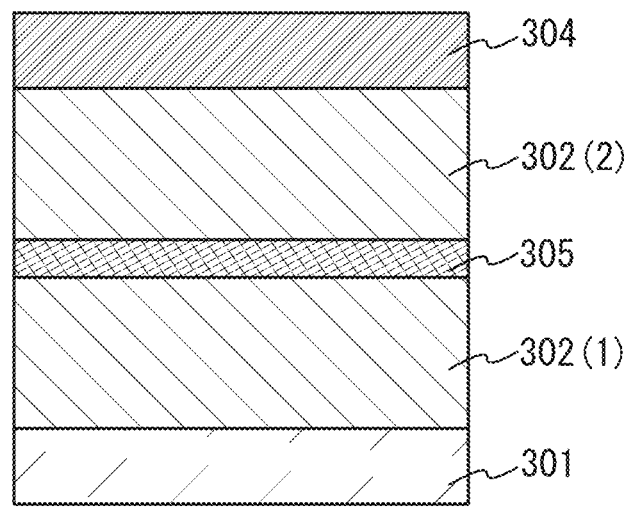
FIGS. 4A and 4B each illustrate an example of a light-emitting element of one embodiment of the present invention.

As illustrated in FIG. 4A, the light-emitting element described in this embodiment is a tandem light-emitting element including a plurality of EL layers (a first EL layer 302(1) and a second EL layer 302(2)) between a pair of electrodes (a first electrode 301 and a second electrode 304).

In this embodiment, the first electrode 301 functions as an anode, and the second electrode 304 functions as a cathode. Note that the first electrode 301 and the second electrode 304 can have structures similar to those described in Embodiment 1. In addition, all or any of the plurality of EL layers (the first EL layer 302(1) and the second EL layer 302(2)) may have structures similar to those described in Embodiment 1. In other words, the structures of the first EL layer 302(1) and the second EL layer 302(2) may be the same or different from each other and can be similar to those described in Embodiment 1.

Further, a charge-generation layer 305 is provided between the plurality of EL layers (the first EL layer 302(1) and the second EL layer 302(2)). The charge-generation layer 305 has a function of injecting electrons into one of the EL layers and injecting holes into the other of the EL layers when a voltage is applied between the first electrode 301 and the second electrode 304. In this embodiment, when a voltage is applied such that the potential of the first electrode 301 is higher than that of the second electrode 304, the charge-generation layer 305 injects electrons into the first EL layer 302(1) and injects holes into the second EL layer 302(2).

Note that in terms of outcoupling efficiency, the charge-generation layer 305 preferably has a property of transmitting visible light (specifically, the charge-generation layer 305 has a visible light transmittance of 40% or more). Further, the charge-generation layer 305 functions even if it has lower conductivity than the first electrode 301 or the second electrode 304.

The charge-generation layer 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, examples of the organic compound having a high hole-transport property are aromatic amine compounds such as NPB, TPD, TDATA, MTDATA, and 4,4'-bis[N-(spiro-9,9'-bifluoren-2-yl)-N-phenylamino]biphenyl (abbreviation: BSPB). The substances given here are mainly substances having a hole mobility of $10^{-6}$ cm$^2$/Vs or higher. Note that any other substances may also be used as long as the substances have hole-transport properties higher than electron-transport properties. Note that the anthracene compound described in Embodiment 1 can also be used as the organic compound having a high hole-transport property in the charge-generation layer 305.

Further, examples of the electron acceptor include 7,7,8,8-tetracyano-2,3,5,6-tetrafluoroquinodimethane (abbreviation: F$_4$-TCNQ) and chloranil. Other examples include transition metal oxides. Other examples include oxides of metals belonging to Group 4 to Group 8 of the periodic table. Specifically, vanadium oxide, niobium oxide, tantalum oxide, chromium oxide, molybdenum oxide, tungsten oxide, manganese oxide, and rhenium oxide are preferable because of their high electron accepting properties. Among these, molybdenum oxide is especially preferable because it is stable in the air, has a low hygroscopic property, and is easily handled.

On the other hand, in the case of the structure in which an electron donor is added to an organic compound having a high electron-transport property, for example, a metal complex having a quinoline skeleton or a benzoquinoline skeleton, such as Alq, Almq$_3$, BeBq$_2$, or BAlq, or the like can be used as the organic compound having a high electron-transport property. Alternatively, a metal complex having an oxazole-based ligand or a thiazole-based ligand, such as Zn(BOX)$_2$ or Zn(BTZ)$_2$ can be used. Other than metal complexes, PBD, OXD-7, TAZ, BPhen, BCP, or the like can be used. The substances given here are mainly substances having an electron mobility of 10$^{-6}$ cm$^2$/Vs or higher. Note that any other substances may also be used as long as the substances have electron-transport properties higher than hole-transport properties. The anthracene compound described in Embodiment 1 can also be used as the organic compound having a high electron-transport property.

As the electron donor, an alkali metal, an alkaline earth metal, a rare earth metal, a metal belonging to Group 2 or Group 13 of the periodic table, or an oxide or a carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer 305 by using any of the above materials can suppress an increase in drive voltage caused by the stack of the EL layers.

Figure 4B:
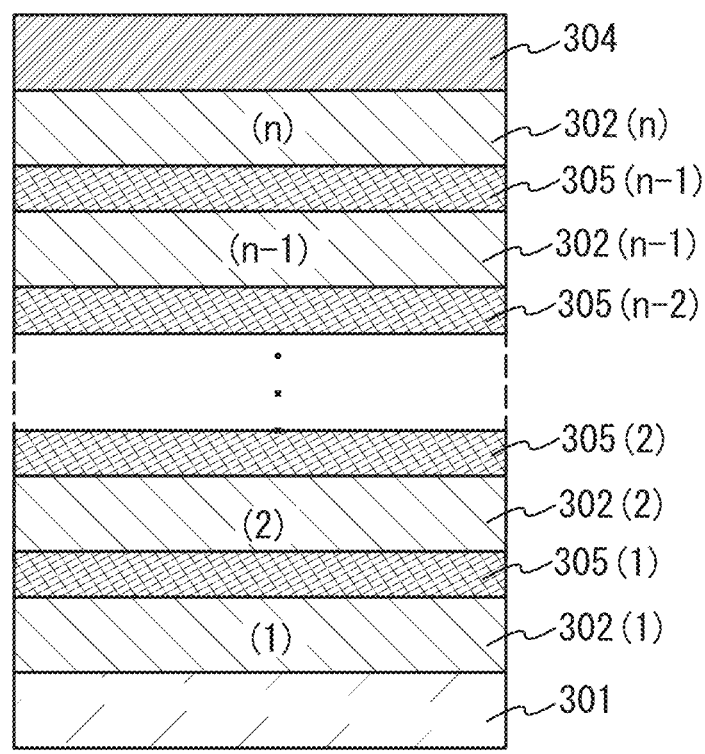

Although the light-emitting element including two EL layers is described in this embodiment, the present invention can be similarly applied to a light-emitting element in which n EL layers (n is three or more) are stacked as illustrated in FIG. 4B. In the case where a plurality of EL layers are included between a pair of electrodes as in the light-emitting element according to this embodiment, by providing the charge-generation layer between the EL layers, the light-emitting element can emit light in a high luminance region while the current density is kept low. Since the current density can be kept low, the light-emitting element can have a long lifetime. When the light-emitting element is applied to illumination, voltage drop due to resistance of an electrode material can be reduced, thereby achieving homogeneous light emission in a large area. In addition, a low power consumption light-emitting device, which can be driven at low voltage, can be achieved.

By making the EL layers emit light of different colors from each other, the light-emitting element can provide light emission of a desired color as a whole. For example, by forming a light-emitting element having two EL layers such that the emission color of the first EL layer and the emission color of the second EL layer are complementary colors, the light-emitting element can provide white light emission as a whole. Note that "complementary colors" refer to colors that can produce an achromatic color when mixed. In other words, when lights obtained from substances which emit light of complementary colors are mixed, white emission can be obtained.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be used as appropriate in combination with any of the structures described in the other embodiments.

Embodiment 3

In this embodiment, examples of electronic devices and lighting devices including a light-emitting device of one embodiment of the present invention are described with reference to FIGS. 5A to 5E and FIGS. 6A and 6B.

The electronic devices in this embodiment each include the light-emitting device of one embodiment of the present invention in a display portion. The lighting devices in this embodiment each include the light-emitting device of one embodiment of the present invention in a light-emitting portion (lighting portion). An electronic device and a lighting device with low power consumption can be obtained by using the light-emitting device of one embodiment of the present invention.

Examples of the electronic devices to which the light-emitting device is applied include television devices (also referred to as TV or television receivers), monitors for computers and the like, digital cameras, digital video cameras, digital photo frames, mobile phones (also referred to as cellular phones or mobile phone devices), portable game machines, portable information terminals, audio playback devices, and large-sized game machines such as pachinko machines. Specific examples of these electronic devices and lighting devices are illustrated in FIGS. 5A to 5E and FIGS. 6A and 6B.

FIG. 5A illustrates an example of a television device. In a television device 7100, a display portion 7102 is incorporated in a housing 7101. Images can be displayed on the display portion 7102. The light-emitting device of one embodiment of the present invention can be used for the display portion 7102. In addition, here, the housing 7101 is supported by a stand 7103.

The television device 7100 can be operated with an operation switch of the housing 7101 or a separate remote controller 7111. With operation keys of the remote controller 7111, channels and volume can be controlled and images displayed on the display portion 7102 can be controlled. The remote controller 7111 may be provided with a display portion for displaying data output from the remote controller 7111.

Note that the television device 7100 is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

FIG. 5B illustrates an example of a computer. A computer 7200 includes a main body 7201, a housing 7202, a display portion 7203, a keyboard 7204, an external connection port 7205, a pointing device 7206, and the like. Note that the computer 7200 is manufactured by using the light-emitting device of one embodiment of the present invention for the display portion 7203.

FIG. 5C illustrates an example of a portable game machine. A portable game machine 7300 has two housings, a housing 7301*a* and a housing 7301*b*, which are connected with a joint portion 7302 so that the portable game machine can be opened and closed. The housing 7301*a* incorporates a display portion 7303*a*, and the housing 7301*b* incorporates a display portion 7303*b*. In addition, the portable game machine illustrated in FIG. 5C includes a speaker portion 7304, a recording medium insertion portion 7305, operation keys 7306, a connection terminal 7307, a sensor 7308 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, vibration, smell, or infrared ray), an LED lamp, a microphone, and the like. Needless to say, the structure of the portable game machine is not limited to the above as long as the light-emitting device of one embodiment of the present invention is used for at least either the display portion 7303*a* or the display portion 7303*b*, or both of them. The portable game machine may be provided with other accessories as appropriate. The portable game machine illustrated in FIG. 5C has a function of reading a program or data stored in a recording medium to display it on the display portion, and a function of sharing data with another portable game machine by wireless communication. Note that functions of the portable game machine illustrated in FIG. 5C are not limited to the above, and the portable game machine can have a variety of functions.

FIG. 5D illustrates an example of a mobile phone. A mobile phone 7400 includes a display portion 7402 incorporated in a housing 7401, operation buttons 7403, an external connection port 7404, a speaker 7405, a microphone 7406, and the like. Note that the mobile phone 7400 is manufactured by using the light-emitting device of one embodiment of the present invention for the display portion 7402.

When the display portion 7402 of the mobile phone 7400 illustrated in FIG. 5D is touched with a finger or the like, data can be input into the mobile phone 7400. Further, operations such as making a call and creating an e-mail can be performed by touch on the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or composing an e-mail, a text input mode mainly for inputting text is selected for the display portion 7402 so that text displayed on the screen can be input.

When a sensing device including a sensor such as a gyroscope sensor or an acceleration sensor for detecting inclination is provided inside the mobile phone 7400, display on the screen of the display portion 7402 can be automatically changed in direction by determining the orientation of the mobile phone 7400 (whether the mobile phone 7400 is placed horizontally or vertically for a landscape mode or a portrait mode).

The screen modes are switched by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touch on the display portion 7402 is not performed within a specified period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, when a backlight or a sensing light source which emits near-infrared light is provided in the display portion, an image of a finger vein, a palm vein, or the like can be taken.

FIG. 5E illustrates an example of a foldable tablet terminal (which is unfolded). A tablet terminal 7500 includes a housing 7501*a*, a housing 7501*b*, a display portion 7502*a*, and a display portion 7502*b*. The housing 7501*a* and the housing 7501*b* are connected by a hinge 7503 and can be opened and closed using the hinge 7503 as an axis. The housing 7501*a* includes a power switch 7504, operation keys 7505, a speaker 7506, and the like. Note that the tablet terminal 7500 is manufactured by using the light-emitting device of one embodiment of the present invention for either the display portion 7502*a* or the display portion 7502*b*, or both of them.

At least part of the display portion 7502*a* or the display portion 7502*b* can be used as a touch panel region, where data can be input by touching displayed operation keys. For example, the entire area of the display portion 7502*a* can display keyboard buttons and serve as a touch panel while the display portion 7502*b* is used as a display screen.

Figure 6A:
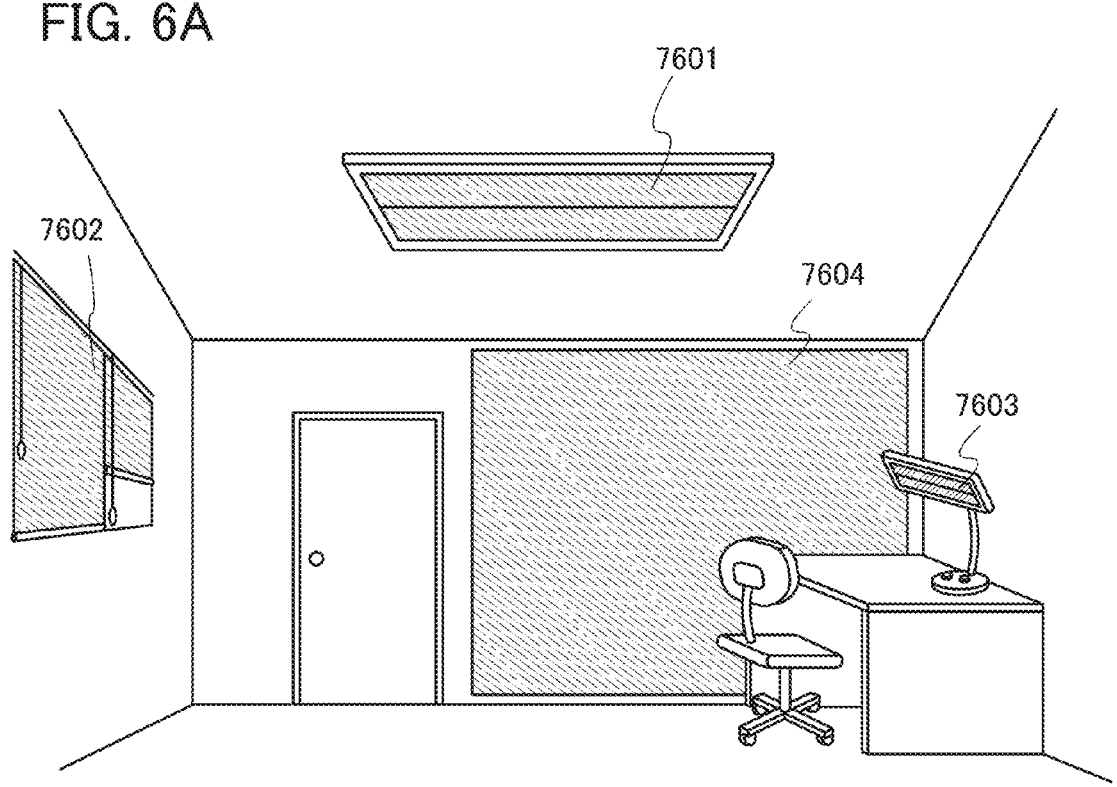
FIGS. 6A and 6B illustrate examples of lighting devices.

An indoor lighting device 7601, a roll-type lighting device 7602, a desk lamp 7603, and a planar lighting device 7604, which are illustrated in FIG. 6A, are each an example of a lighting device including the light-emitting device of one embodiment of the present invention. The light-emitting device of one embodiment of the present invention can have a larger area and thus can be used as a lighting device having a large area. In addition, the light-emitting device is thin and thus can be mounted on a wall.

Figure 6B:
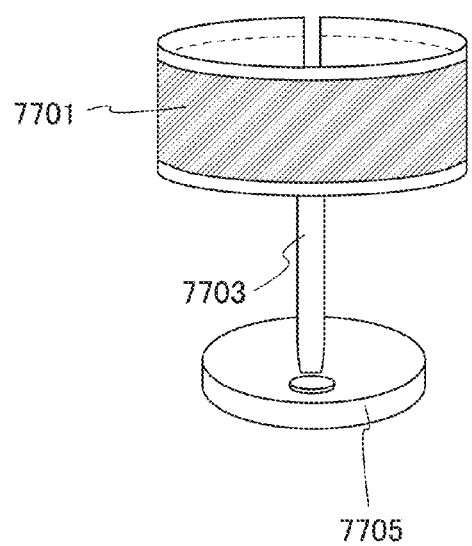

A desk lamp illustrated in FIG. 6B includes a lighting portion 7701, a support 7703, a support base 7705, and the like. The light-emitting device of one embodiment of the present invention is used for the lighting portion 7701. In one embodiment of the present invention, a lighting device whose light-emitting portion has a curved surface or a lighting device including a flexible lighting portion can be achieved. The use of a flexible light-emitting device for a lighting device as described above not only improves the degree of freedom in design of the lighting device but also enables the lighting device to be mounted onto a portion having a curved surface, such as the ceiling or a dashboard of a car.

This embodiment can be combined with any of the other embodiments as appropriate.

Example 1

Synthesis Example 1

In this example, a specific example of a method for synthesizing 2'-(3,5-diphenyl)phenyl-dispiro[9H-fluorene-9,9'(10'H)-anthracene-10',9"-(9H)fluorene] (abbreviation: 2mTPDfha), which is one embodiment of the anthracene compound described in Embodiment 1, is described. Note that Structural Formula (100) of 2mTPDfha (abbreviation) is shown below.

(100)

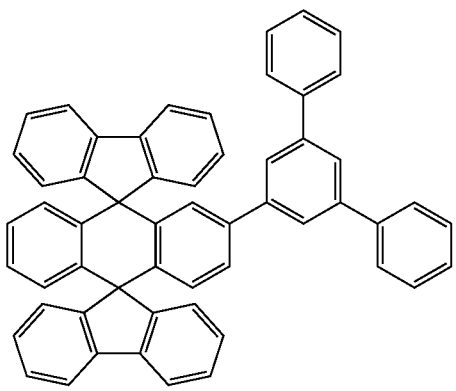

In a 100 ml three-neck flask were put 1.4 g (2.4 mmol) of 2'-bromo-dispiro[9H-fluorene-9,9'(10'H)-anthracene-10',9''-(9H)-fluorene] (abbreviation: 2BrDfha), 0.80 g (2.9 mmol) of (3,5-diphenylphenyl)boronic acid, and 89 mg (292 μmol) of tris(2-methylphenyl)phosphine, and the air in the flask was replaced with nitrogen. Then, 30 ml of toluene, 2.9 ml of ethanol, and 2.9 ml of a 2M aqueous solution of potassium carbonate (810 mg of potassium carbonate) were added thereto, and the mixture was degassed while being stirred under reduced pressure. Then, 32 mg (150 μmol) of palladium acetate was added thereto, and the mixture was stirred at 85° C. under a nitrogen stream for 8 hours. Then, 89 mg (290 μmol) of tris(2-methylphenyl)phosphine and 33 mg (150 μmol) of palladium acetate were added thereto, and the mixture was stirred at 85° C. for 5 hours. Then, 200 mg (730 μmol) of (3,5-diphenylphenyl)boronic acid, 270 mg (880 μmol) of tris(2-methylphenyl)phosphine, and 98 mg (440 μmol) of palladium acetate were added thereto, and the mixture was stirred at 85° C. under a nitrogen stream for 9.5 hours. After the stirring for a predetermined time, toluene was added to the mixture and the mixture was filtered with diatomaceous earth. Water was added to the obtained filtrate, and extraction with toluene was performed to obtain an organic layer. The obtained organic layer was washed with saturated saline, and magnesium sulfate was added thereto. The mixture was gravity-filtered, and the obtained filtrate was condensed to give a yellow solid. The obtained yellow solid was purified by silica gel column chromatography (from a mixed solution of toluene and hexane to a mixed solution of ethyl acetate and hexane) to give a fraction including a target substance and a fraction including a target substance mixed with an impurity. The fraction including the target substance was condensed, a mixed solution of hexane and acetone was added thereto, the mixture was irradiated with ultrasonic waves, and the mixture was subjected to suction filtration to give 650 mg of a white solid, which was a target substance, in a yield of 38%. The fraction including the target substance mixed with the impurity was condensed, dissolved in approximately 40 ml of hot toluene, and approximately 10 ml of hexane was added thereto to perform recrystallization, so that a white solid was obtained. A mixed solution of hexane and acetone was added to the obtained white solid, the mixture was irradiated with ultrasonic waves, and the mixture was subjected to suction filtration to give 390 mg of a white solid, which was a target substance, in a yield of 22%. The obtained substance was 1.0 g in total, and the yield was 60%. Synthesis Scheme (a-1) of this synthesis is shown below.

(a-1)

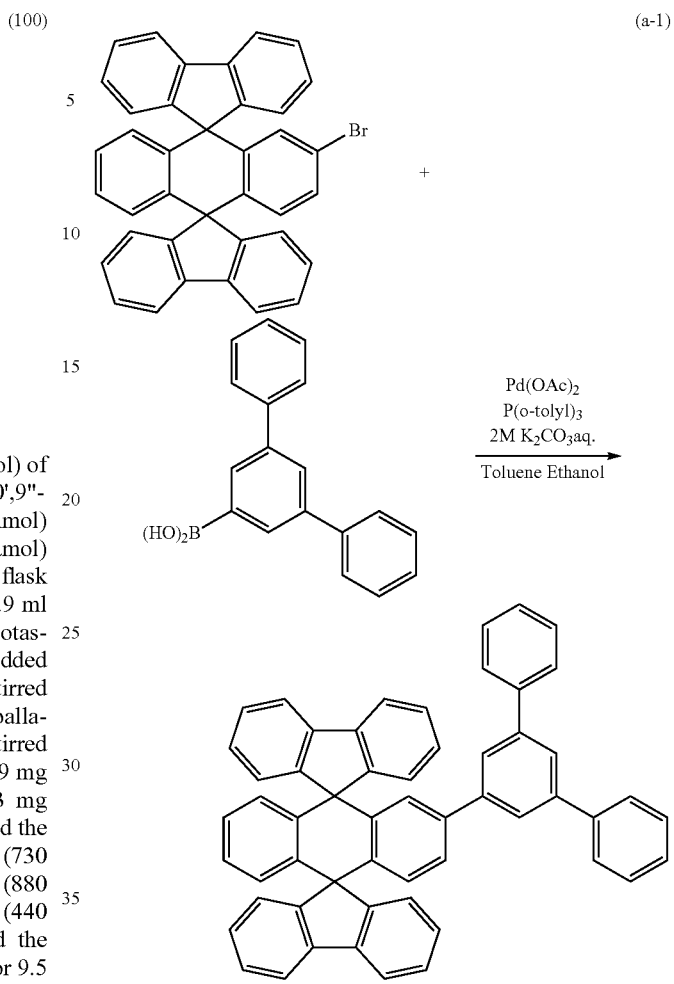

¹H NMR (300 MHz, CDCl₃) data of the obtained substance are as follows. ¹H NMR (300 MHz, CDCl₃): δ (ppm)=6.40-6.45 (m, 2H), 6.50 (d, J=8.4 Hz, 1H), 6.65 (d, J=1.8 Hz, 1H), 6.77-6.82 (m, 2H), 7.08 (dd, J=1.8 Hz, 8.3 Hz, 1H), 7.25-7.50 (m, 24H), 7.60 (t, J=1.5 Hz, 1H), 7.90-7.96 (m, 4H).

Figure 8A:
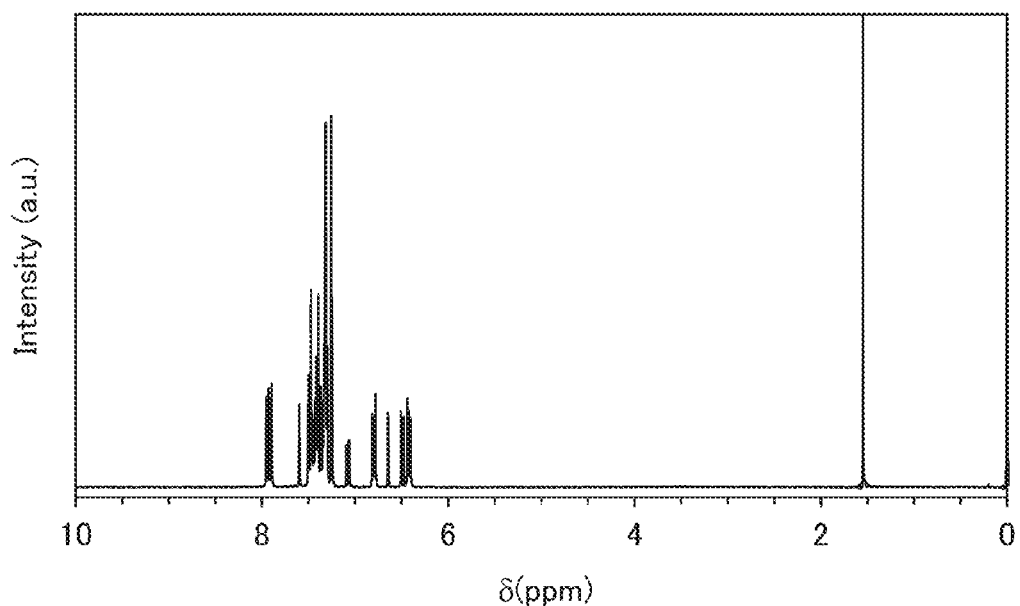
FIGS. 8A and 8B are $^1$H NMR charts of an anthracene compound (2mTPDfha) represented by Structural Formula (100).
Figure 8B:
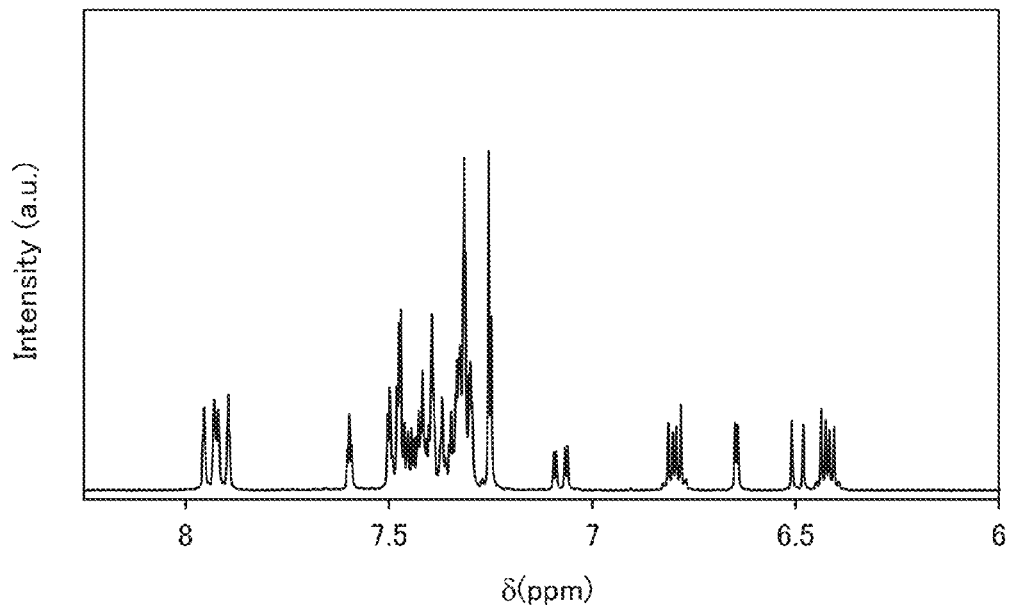

FIGS. 8A and 8B show ¹H NMR (300 MHz, CDCl₃) data of the obtained substance. FIG. 8B is a chart where the range of from 6 ppm to 9 ppm in FIG. 8A is enlarged.

An ultraviolet-visible absorption spectrum (hereinafter, simply referred to as absorption spectrum) and an emission spectrum of 2'-(3,5-diphenyl)phenyl-dispiro[9H-fluorene-9,9'(10'H)-anthracene-10',9''-(9H)fluorene] (abbreviation: 2mTPDfha) in a toluene solution were measured. The absorption spectrum was measured at room temperature with the use of an ultraviolet-visible light spectrophotometer (V-550, manufactured by JASCO Corporation) in a state where a toluene solution was put in a quartz cell. The emission spectrum was measured with the use of a fluorescence spectrophotometer (FS920, manufactured by Hamamatsu Photonics Corporation) in a state where a degassed toluene solution was put in a quartz cell at room temperature. As for the measurement of the absorption spectrum of a thin film, the absorption spectrum was obtained as follows: the thin film that was formed by evaporation on a quartz substrate was used and an absorption spectrum of quartz was subtracted from absorption spectra of the thin film and the quartz.

In the case of the toluene solution of 2mTPDfha (abbreviation), the absorption peak was observed at around 311 nm. In the case of the thin film of 2mTPDfha (abbreviation), the absorption peak was observed at around 312 nm.

Further, in the case of the toluene solution of 2mTPDfha (abbreviation), the maximum emission wavelength was 350 nm (excitation wavelength: 270 nm). In the case of the thin film of 2mTPDfha (abbreviation), the maximum emission wavelength was 353 nm (excitation wavelength: 312 nm).

The above results demonstrate that 2mTPDfha (abbreviation) of one embodiment of the present invention has a high $S_1$ level and emits ultraviolet fluorescence.

Next, 2mTPDfha (abbreviation) was subjected to cyclic voltammetry (CV) measurement. An electrochemical analyzer (ALS model 600A or 600C, manufactured by BAS Inc.) was used for the CV measurement.

Further, as for a solution used for the CV measurements, dehydrated dimethylformamide (DMF, produced by Sigma-Aldrich Inc., 99.8%, Catalog No. 22705-6) was used as a solvent, and tetra-n-butylammonium perchlorate (n-Bu$_4$NClO$_4$, produced by Tokyo Chemical Industry Co., Ltd., Catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 2 mmol/L. A platinum electrode (PTE platinum electrode, produced by BAS Inc.) was used as a working electrode, another platinum electrode (Pt counter electrode for VC-3 (5 cm), produced by BAS Inc.) was used as an auxiliary electrode, and an Ag/Ag$^+$ electrode (RE7 reference electrode for non-aqueous solvent, produced by BAS Inc.) was used as a reference electrode. The CV measurement was performed under the following conditions: room temperature (20° C. to 25° C.) and a scan rate of 0.1 V/sec. Note that the potential energy of the reference electrode with respect to the vacuum level was assumed to be −4.94 eV in this example.

The LUMO level of 2mTPDfha (abbreviation) was obtained from the CV measurement results. From a reduction peak potential (from the neutral state to the reduction state) $E_{pa}$ [V] and an oxidation peak potential (from the reduction state to the neutral state) $E_{pc}$ [V], a half wave potential (a potential between $E_{pa}$ and $E_{pc}$) was calculated to be −2.75 eV (($E_{pa}$+$E_{pc}$)/2 [V]=−2.75 eV). Then, a half wave potential of −2.75 eV was subtracted from a potential energy of the reference electrode with respect to the vacuum level of −4.94 eV to obtain a LUMO level (a reduction potential) of −2.20 eV.

The above results demonstrate that 2mTPDfha (abbreviation) of one embodiment of the present invention has a relatively shallow LUMO level.

Furthermore, mass spectrometry (MS) of 2mTPDfha (abbreviation) was carried out by liquid chromatography mass spectrometry (LC/MS).

The analysis by LC/MS was carried out with Acquity UPLC (produced by Waters Corporation) and Xevo G2 Tof MS (produced by Waters Corporation). ACQUITY UPLC BEH C8 (2.1×100 mm, 1.7 μm) was used as a column for the LC separation, and the column temperature was 40° C. Acetonitrile was used for Mobile Phase A and 0.1 volume % of a formic acid aqueous solution was used for Mobile Phase B. Further, a sample was prepared in such a manner that 2mTPDfha (abbreviation) was dissolved in toluene at a given concentration and the mixture was diluted with acetonitrile. The injection amount was 5.0 μL.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 709.29 that underwent the ionization under the above-described conditions was collided with an argon gas in a collision cell to dissociate into product ions. Energy (collision energy) for the collision with argon was 70 eV. The mass range for the measurement was m/z=100 to 1200. The detection results of the dissociated product ions by time-of-flight (TOF) MS are shown in FIGS. 9A and 9B. FIG. 9B is obtained by increasing the scale of the vertical axis of FIG. 9A.

The results in FIGS. 9A and 9B show that the product ion of 2mTPDfha (abbreviation) is detected mainly around m/z=403.15. Note that the results in FIGS. 9A and 9B show characteristics derived from 2mTPDfha (abbreviation) and therefore can be regarded as important data for identifying 2mTPDfha (abbreviation) contained in the mixture.

Note that the product ion around m/z=403.15 is presumed to be a radical cation in the state (C$_{32}$H$_{19}$) where a benzene skeleton is dissociated from 2mTPDfha (abbreviation).

Example 2

Synthesis Example 2

In this example, a specific example of a method for synthesizing 9-(3-{dispiro[9H-fluorene-9,9'(10'H)-anthracene-10',9''-(9H)fluorene]2'-yl}phenyl)-9H-carbazole (abbreviation: 2mCzPDfha), which is one embodiment of the anthracene compound described in Embodiment 1, is described. Note that Structural Formula (103) of 2mCzPDfha (abbreviation) is shown below.

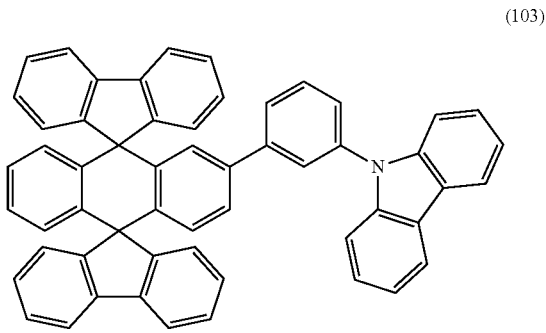 [SMILES: c1cc(-c2ccc3c(c2)C2(c4ccccc4-c4ccccc42)c2ccccc2C32c3ccccc3-c3ccccc32)cc(-n2c3ccccc3c3ccccc32)c1]

(103)

In a 100 ml three-neck flask were put 1.25 g (2.23 mmol) of 7-bromo-dispiro[9H-fluorene-9,9'(10'H)-anthracene-10',9''-(9H)-fluorene] (abbreviation: 2BrDfha), 770 mg (2.68 mmol) of 3-(carbazol-9-yl)phenylboronic acid, and 81.6 mg (268 μmol) of tris(2-methylphenyl)phosphine, and the air in the flask was replaced with nitrogen. Then, 30 ml of toluene, 2.7 ml of ethanol, and 2.7 ml of a 2M aqueous solution of potassium carbonate (741 mg of potassium carbonate) were added thereto, and the mixture was degassed while being stirred under reduced pressure. Then, 30.1 mg (134 μmol) of palladium acetate was added thereto, and the mixture was stirred at 85° C. under a nitrogen stream for 8 hours. Then, 81.6 mg (268 μmol) of tris(2-methylphenyl)phosphine and 30.1 mg (134 μmol) of palladium acetate were added thereto, and the mixture was stirred at 85° C. for 5 hours. Then, 201 mg (699 μmol) of 3-(carbazol-9-yl)phenylboronic acid, 245 mg (804 μmol) of tris(2-methylphenyl)phosphine, and 90.3 mg (402 μmol) of palladium acetate were added thereto, and the mixture was stirred at 85° C. under a nitrogen stream for 9.5 hours. After the stirring for a predetermined time, toluene was added to the mixture and the mixture was filtered with diatomaceous earth. Then, water was added to the obtained filtrate and extraction with toluene was performed to obtain an organic layer. The obtained organic layer was washed with saturated saline, and magnesium sulfate was added thereto so that moisture was adsorbed. The mixture was gravity-filtered and the filtrate was condensed, followed by purification by silica gel column chromatography (toluene, a mixed solution of toluene and hexane, and a mixed solution of ethyl acetate and hexane were used) to give a white solid. A mixed solution of hexane and acetone was added to the obtained white solid, and the resulting suspension was subjected to suction filtration to give 0.99 g of a white solid, which was a target substance, in a yield of 61.4%. Synthesis Scheme (a-2) of this synthesis is shown below.

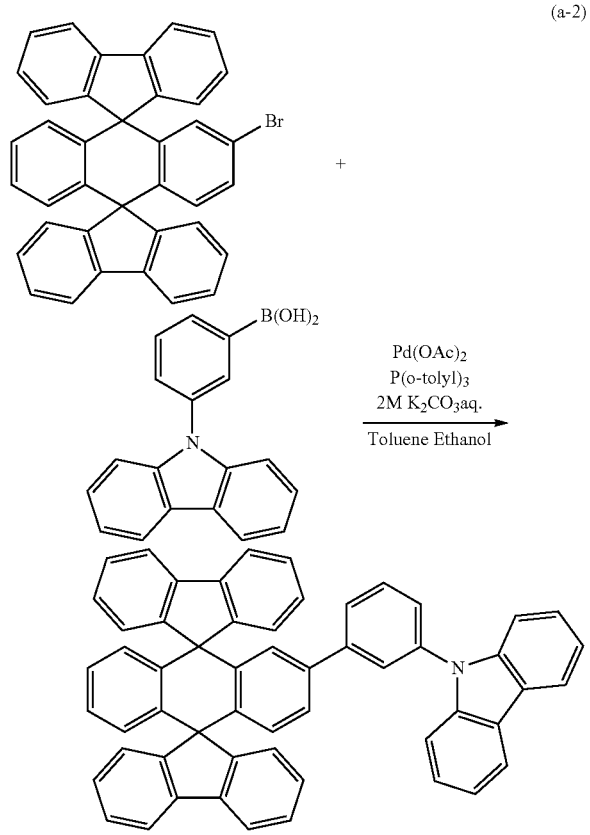

(a-2)

$^1$H NMR data of the obtained substance are as follows.
$^1$H NMR (300 MHz, CDCl$_3$): δ (ppm)=6.38-6.52 (m, 3H), 6.64-6.69 (m, 1H), 6.76-6.85 (m, 2H), 7.04 (dd, J=2.4 Hz, 8.4 Hz, 1H), 7.09-7.17 (m, 1H), 7.21-7.49 (m, 21H), 7.93 (d, J=7.2 Hz, 4H), 8.10 (d, J=7.8 Hz, 2H).

Figure 10A:
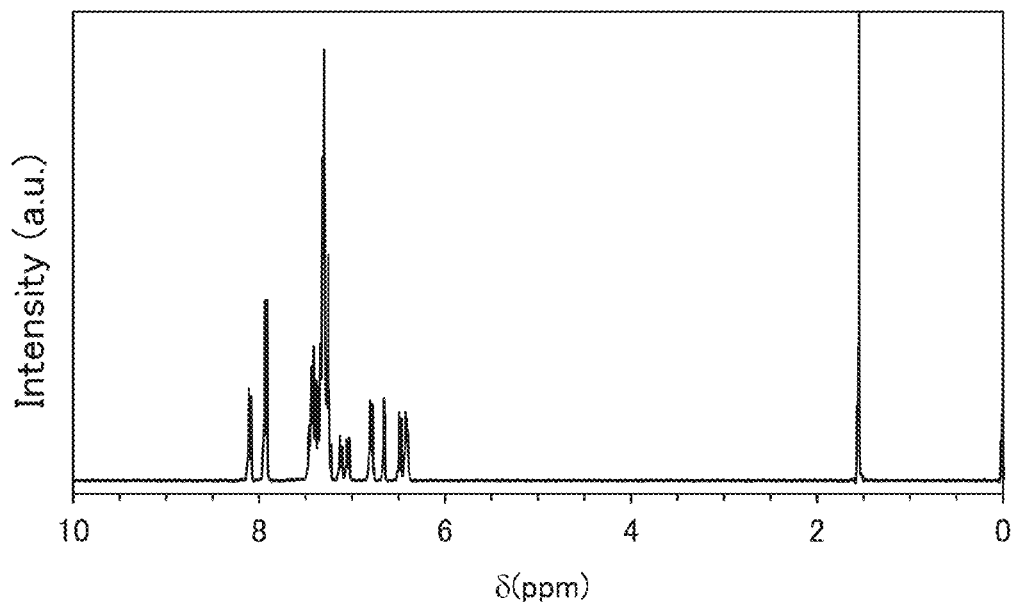
FIGS. 10A and 10B are $^1$H NMR charts of an anthracene compound (2mCzPDfha) represented by Structural Formula (103).
Figure 10B:
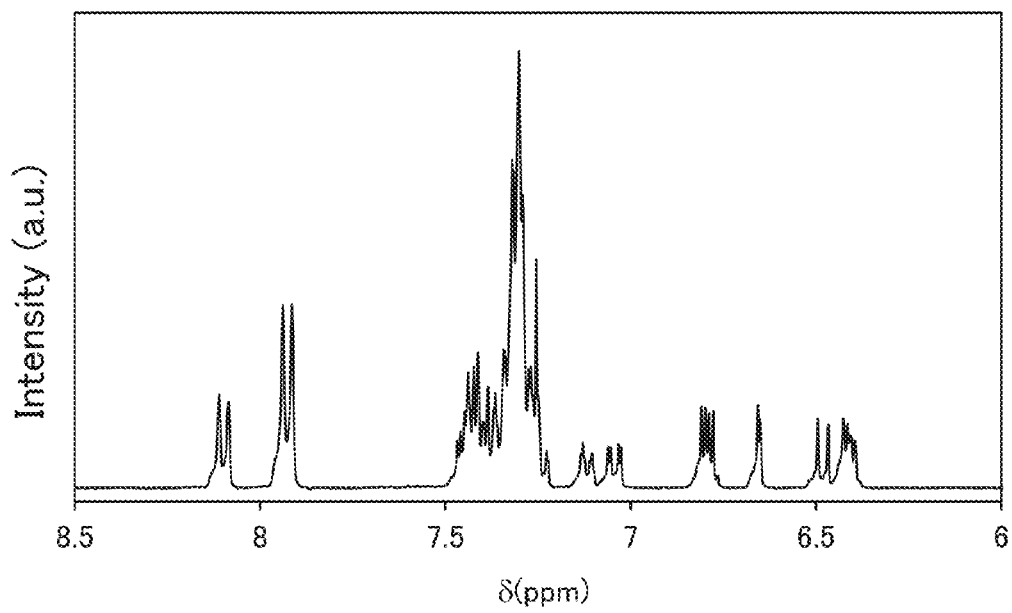

FIGS. 10A and 10B show $^1$H NMR (300 MHz, CDCl$_3$) data of the obtained substance. FIG. 10B is a chart where the range of from 6 ppm to 8.5 ppm in FIG. 10A is enlarged.

An ultraviolet-visible absorption spectrum and an emission spectrum of 9-(3-{dispiro[9H-fluorene-9,9'(10'H)-anthracene-10',9'''-(9H)fluorene]2'-yl}phenyl)-9H-carbazole (abbreviation: 2mCzPDfha) in a toluene solution were measured. The absorption spectrum was measured at room temperature with the use of an ultraviolet-visible light spectrophotometer (V-550, manufactured by JASCO Corporation) in a state where a toluene solution was put in a quartz cell. The emission spectrum was measured with the use of a fluorescence spectrophotometer (FS920, manufactured by Hamamatsu Photonics Corporation) in a state where a degassed toluene solution was put in a quartz cell at room temperature. As for the measurement of the absorption spectrum of a thin film, the absorption spectrum was obtained as follows: the thin film that was formed by evaporation on a quartz substrate was used and an absorption spectrum of quartz was subtracted from absorption spectra of the thin film and quartz.

In the case of the toluene solution of 2mCzPDfha (abbreviation), the absorption peak was observed at around 341 nm. In the case of the thin film of 2mCzPDfha (abbreviation), the absorption peak was observed at around 343 nm.

Further, in the case of the toluene solution of 2mCzPDfha (abbreviation), the emission peaks were observed at 362 nm and 347 nm (excitation wavelength: 290 nm), and the maximum emission wavelength was 347 nm. In the case of the thin film of 2mCzPDfha (abbreviation), the emission peaks were observed at 450 nm, 424 nm, 366 nm, and 351 nm (excitation wavelength: 344 nm), and the maximum emission wavelength was 351 nm.

The above results demonstrate that 2mCzPDfha (abbreviation) of one embodiment of the present invention has a high $S_1$ level and emits purple fluorescence.

Next, 2mCzPDfha (abbreviation) was subjected to cyclic voltammetry (CV) measurement. An electrochemical analyzer (ALS model 600A or 600C, manufactured by BAS Inc.) was used for the CV measurement.

Further, as for a solution used for the CV measurements, dehydrated dimethylformamide (DMF, produced by Sigma-Aldrich Inc., 99.8%, Catalog No. 22705-6) was used as a solvent, and tetra-n-butylammonium perchlorate (n-Bu$_4$NClO$_4$, produced by Tokyo Chemical Industry Co., Ltd., Catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 2 mmol/L. A platinum electrode (PTE platinum electrode, produced by BAS Inc.) was used as a working electrode, another platinum electrode (Pt counter electrode for VC-3 (5 cm), produced by BAS Inc.) was used as an auxiliary electrode, and an Ag/Ag$^+$ electrode (RE7 reference electrode for non-aqueous solvent, produced by BAS Inc.) was used as a reference electrode. The CV measurement was performed under the following conditions: room temperature (20° C. to 25° C.) and a scan rate of 0.1 V/sec. Note that the potential energy of the reference electrode with respect to the vacuum level was assumed to be −4.94 eV in this example.

The LUMO level of 2mCzPDfha (abbreviation) was obtained from the CV measurement results. From a reduction peak potential (from the neutral state to the reduction state) $E_{pa}$ [V] and an oxidation peak potential (from the reduction state to the neutral state) $E_{pc}$ [V], a half wave potential (a potential between $E_{pa}$ and $E_{pc}$) was calculated to be −2.78 eV (($E_{pa}+E_{pc}$)/2 [V]=−2.78 eV). Then, a half wave potential of −2.78 eV was subtracted from a potential energy of the reference electrode with respect to the vacuum level of −4.94 eV to obtain a LUMO level (a reduction potential) of −2.16 eV.

Next, the HOMO level (oxidation potential) of 2mCzPDfha (abbreviation) was obtained from the CV measurement results. Scan was performed to the oxidation side (0.2 eV to 1.0 eV) to obtain a HOMO level of −5.90 eV.

The above results demonstrate that 2mCzPDfha (abbreviation) of one embodiment of the present invention has a relatively shallow LUMO level and a relatively deep HOMO level.

Furthermore, mass spectrometry (MS) of 2mCzPDfha (abbreviation) was carried out by liquid chromatography mass spectrometry (LC/MS).

The analysis by LC/MS was carried out with Acquity UPLC (produced by Waters Corporation) and Xevo G2 Tof MS (produced by Waters Corporation). ACQUITY UPLC BEH C8 (2.1×100 mm, 1.7 μm) was used as a column for the LC separation, and the column temperature was 40° C. Acetonitrile was used for Mobile Phase A and 0.1 volume % of a formic acid aqueous solution was used for Mobile Phase B. Further, a sample was prepared in such a manner that 2mCzPDfha (abbreviation) was dissolved in toluene at a given concentration and the mixture was diluted with acetonitrile. The injection amount was 5.0 μL.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 722.29 that underwent the ionization under the above-described conditions was collided with an argon gas in a collision cell to dissociate into product ions. Energy (collision energy) for the collision with argon was 50 eV. The mass range for the measurement was m/z=100 to 1200. The detection results of the dissociated product ions by time-of-flight (TOF) MS are shown in FIG. 11.

Figure 11:
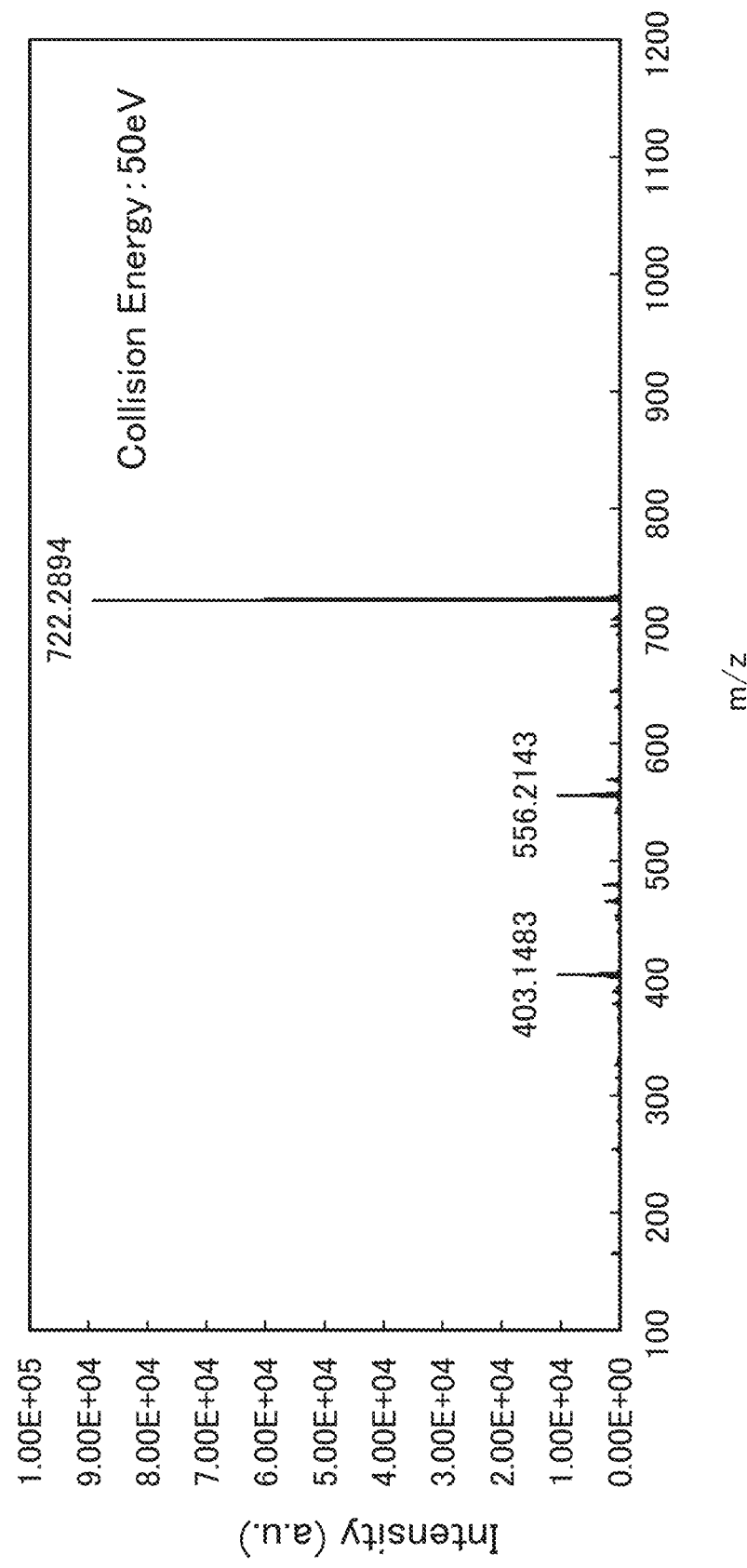
FIG. 11 shows results of LC/MS analysis of the anthracene compound (2mCzPDfha) represented by Structural Formula (103).

The results in FIG. 11 show that the product ions of 2mCzPDfha (abbreviation) are detected mainly around m/z=556.12 and around m/z=403.15. Note that the results in FIG. 11 show characteristics derived from 2mCzPDfha (abbreviation) and therefore can be regarded as important data for identifying 2mCzPDfha (abbreviation) contained in the mixture.

The product ion detected around m/z=556.12 is presumed to be a radical cation in the state ($C_{44}H_{28}$) where a carbazolyl group is dissociated from 2mCzPDfha (abbreviation), which means that 2mCzPDfha (abbreviation) contains a carbazolyl group.

The product ion detected around m/z=403.15 is presumed to be a cation in the state ($C_{32}H_{19}$) where a carbazolyl group and two benzene skeletons are dissociated from 2mCzPDfha (abbreviation).

Example 3

Synthesis Example 3

In this example, a specific example of a method for synthesizing 2-(3-{dispiro[9H-fluorene-9,9'(10'H)-anthracene-10',9'''-(9H)fluoren]2'-yl}phenyl)dibenzo[f,h]quinoxaline (abbreviation: 2mDBqPDfha), which is one embodiment of the anthracene compound described in Embodiment 1, is described. Note that Structural Formula (112) of 2mDBqPDfha (abbreviation) is shown below.

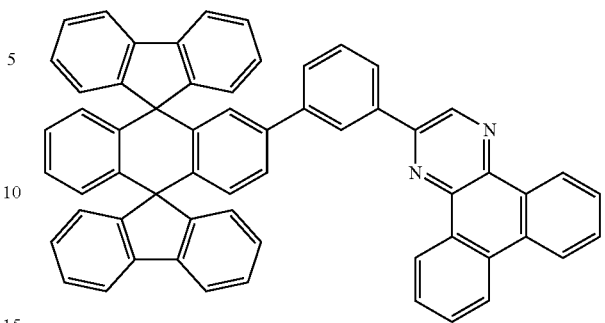

(112)

In a 100 ml three-neck flask were put 1.23 g (3.20 mmol) of 2-(3-bromophenyl)dibenzo[f,h]quinoxaline, 1.85 g (3.52 mmol) of dispiro[9H-fluorene-9,9'(10'H)-anthracene-10',9'''-(9H)fluorene]-2-boronic acid, and 42.9 mg (141 μmol) of tris(2-methylphenyl)phosphine, and the air in the flask was replaced with nitrogen. Then, 35 ml of toluene, 3.5 ml of ethanol, and 3.52 ml (7.04 mmol) of a 2M aqueous solution of potassium carbonate were added thereto, and the mixture was degassed. The degassed mixture was stirred and heated at 85° C. for 25 hours while 47.7 mg (0.21 mmol) of palladium acetate was added thereto in three times and 85.8 mg (0.28 mmol) of tris(2-methylphenyl)phosphine was added thereto in two times. After completion of a reaction, toluene was added thereto to control the amount of liquid to 350 ml and the mixture was heated. Water was added thereto, followed by suction filtration to give a gray solid. Then, 150 ml of toluene was added to the obtained gray solid and the mixture was heated, followed by suction filtration to give a gray solid. Then, 100 ml of toluene was added to the obtained gray solid and the mixture was heated, followed by suction filtration to give a gray solid. Methanol was added to the obtained gray solid and the mixture was irradiated with ultrasonic waves, so that the gray solid was suspended, followed by suction filtration to give 1.84 g of a gray solid, which was a target substance, in a yield of 73.3%. Synthesis Scheme (a-3) of this synthesis is shown below.

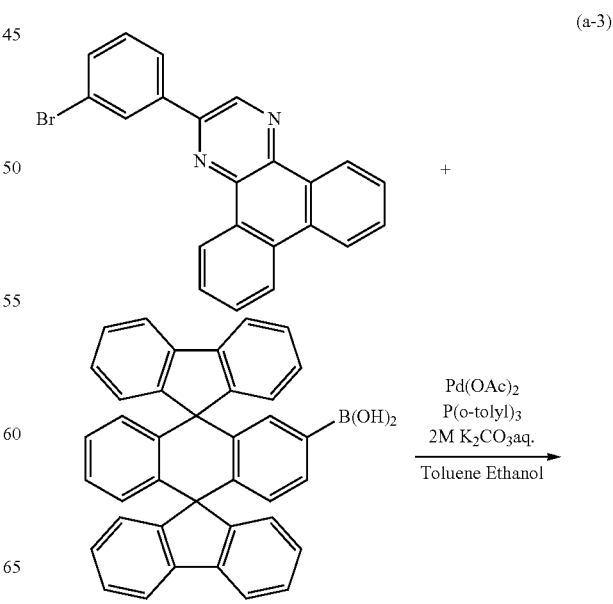

(a-3)

-continued

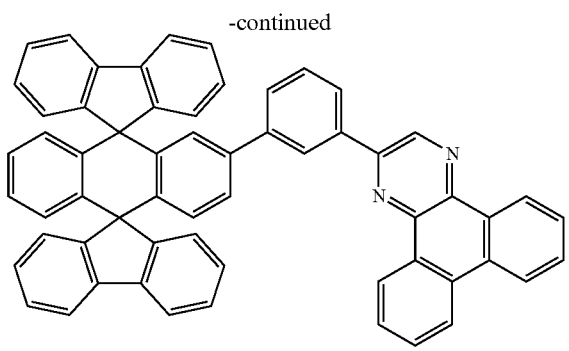

An absorption spectrum and an emission spectrum of 2-(3-{dispiro[9H-fluorene-9,9'(10'H)-anthracene-10',9"-(9H)fluoren]T-yl}phenyl)dibenzo[f,h]quinoxaline (abbreviation: 2mDBqPDfha) in a toluene solution were measured. The absorption and emission spectra were measured in a manner similar to that described in Example 1.

The absorption peak of 2mDBqPDfha (abbreviation) in the toluene solution was observed at around 376 nm.

The emission peaks of 2mDBqPDfha (abbreviation) in the toluene solution were observed at around 408 nm and 487 nm (excitation wavelength: 311 nm), and the maximum emission wavelength was 408 nm.

The above results demonstrate that 2mDBqPDfha (abbreviation) of one embodiment of the present invention has a high $S_1$ level and emits purple fluorescence.

The phosphorescence spectrum of 2mDBqPDfha (abbreviation) was measured by low-temperature PL spectroscopy. The measurement was performed by using a PL microscope, LabRAM HR-PL, produced by HORIBA, Ltd., a He—Cd laser (325 nm) as excitation light, and a CCD detector at a measurement temperature of 10 K. For the measurement, a thin film of 2mDBqPDfha (abbreviation) was formed over a quartz substrate to a thickness of 30 nm and another quartz substrate was attached to the deposition surface in a nitrogen atmosphere. Measurement results demonstrate that 2mDBqPDfha (abbreviation) has a phosphorescence peak at 515 nm and a $T_1$ level high enough to serve as a host material for a green phosphorescent material.

Next, 2mDBqPDfha (abbreviation) was subjected to cyclic voltammetry (CV) measurement. An electrochemical analyzer (ALS model 600A or 600C, manufactured by BAS Inc.) was used for the CV measurement. The measurement was performed in a manner similar to that described in Example 1.

The LUMO level (reduction potential) of 2mDBqPDfha (abbreviation) was calculated from the CV measurement results to be −2.93 eV.

The above results demonstrate that 2mDBqPDfha (abbreviation) of one embodiment of the present invention has a relatively deep LUMO level.

Furthermore, the ionization potential of 2mDBqPDfha (abbreviation) in a thin film state was measured by a photoelectron spectrometer (AC-3 produced by Riken Keiki, Co., Ltd.) in the atmosphere. The obtained value of the ionization potential was converted into a negative value, so that the HOMO level of 2mDBqPDfha (abbreviation) was −6.51 eV. From the data of the absorption spectra of the thin film, the absorption edge of 2mDBqPDfha (abbreviation), which was obtained from Tauc plot with an assumption of direct transition, was 3.11 eV. Therefore, the optical energy gap of 2mDBqPDfha (abbreviation) in the solid state was estimated at 3.11 eV; from the values of the HOMO level obtained above and this energy gap, the LUMO level of 2mDBqPDfha (abbreviation) was able to be estimated at −3.4 eV. It was thus found that 2mDBqPDfha (abbreviation) in the solid state has a relatively deep HOMO and LUMO levels and a wide energy gap of 3.11 eV.

Furthermore, mass spectrometry (MS) of 2mDBqPDfha (abbreviation) was carried out by liquid chromatography mass spectrometry (LC/MS). The measurement was performed in a manner similar to that described in Example 1.

The detection results of the dissociated product ions by time-of-flight (TOF) MS are shown in FIGS. 37A and 37B.

The results in FIGS. 37A and 37B show that the product ions of 2mDBqPDfha (abbreviation) are detected mainly around m/z=785, around m/z=403, and around m/z=631. Note that the results in FIGS. 37A and 37B show characteristics derived from 2mDBqPDfha (abbreviation) and therefore can be regarded as important data for identifying 2mDBqPDfha (abbreviation) contained in the mixture.

Note that the product ion around m/z=631 is presumed to be a radical cation in the state ($C_{48}H_{27}$) where two benzene skeletons are dissociated from 2mDBqPDfha (abbreviation).

Further, the product ion around m/z=403 is presumed to be a cation in the state ($C_{32}H_{19}$) where a 2-phenyl-dibenzo[f,h]quinoxalinyl group and one benzene skeleton are dissociated from 2mDBqPDfha (abbreviation).

Example 4

Figure 7:
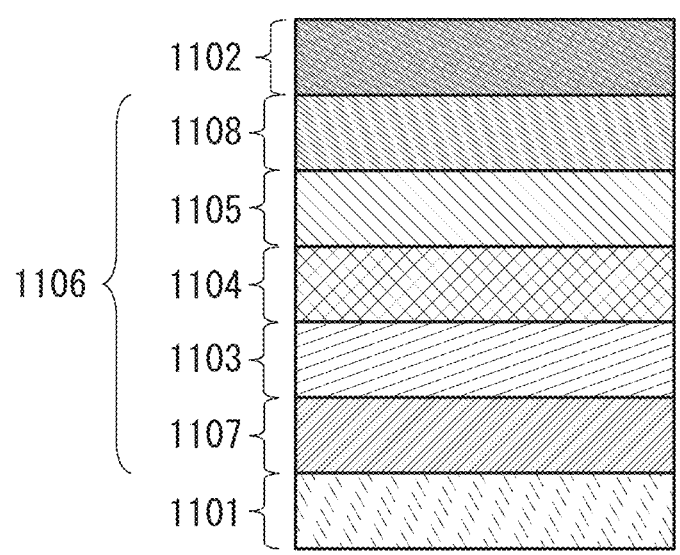
FIG. 7 illustrates a light-emitting element of Examples.

In this example, a light-emitting element 1 that is one embodiment of the present invention is described with reference to FIG. 7. Shown below are molecular structures of organic compounds used in this example.

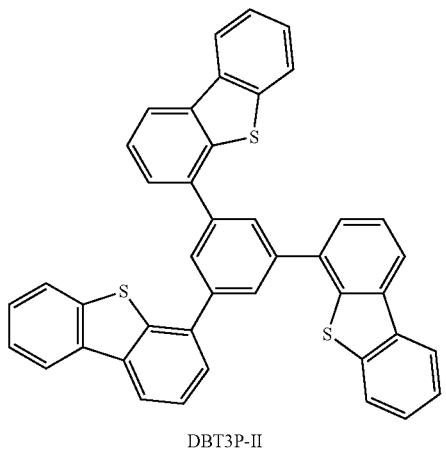

DBT3P-II

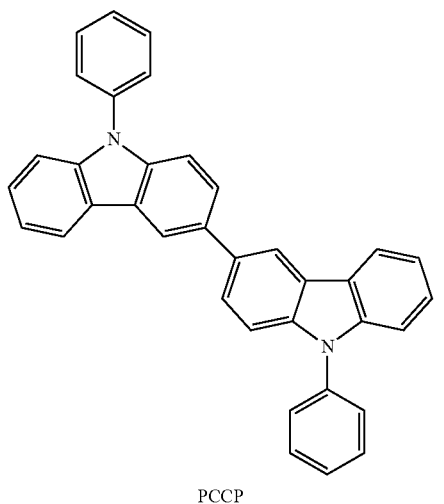

PCCP

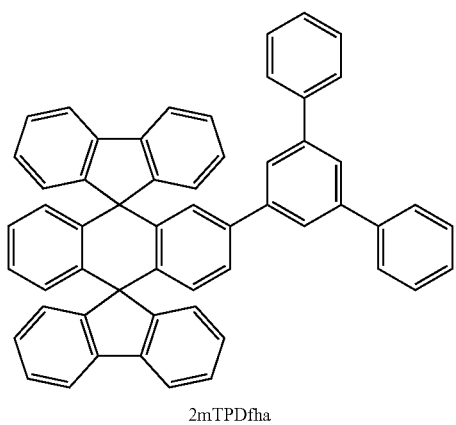

2mTPDfha

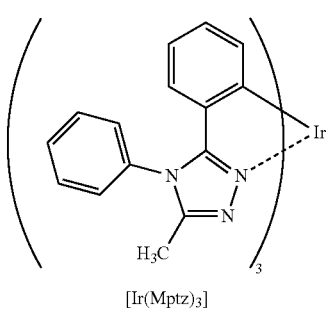

[Ir(Mptz)₃]

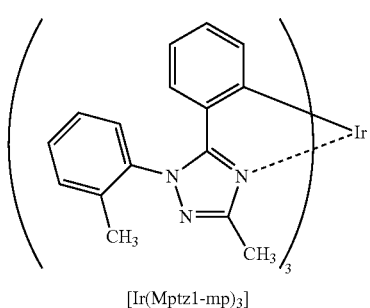

[Ir(Mptz1-mp)₃]

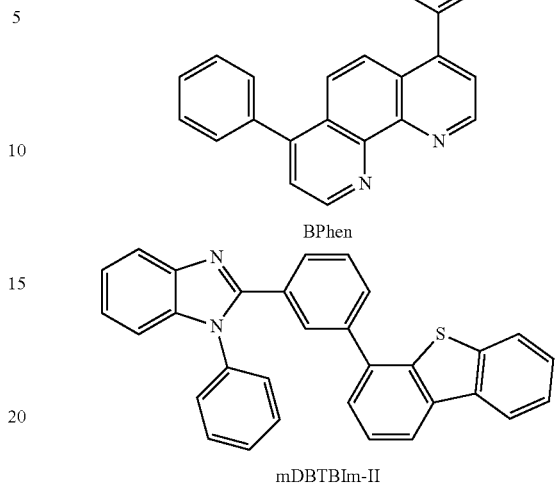

BPhen mDBTBIm-II

<<Manufacture of Light-Emitting Element>>

First, a glass substrate over which a film of indium tin oxide containing silicon (ITSO) with a thickness of 110 nm had been formed as an anode 1101 was prepared. A surface of the ITSO was covered with a polyimide film so that an area of 2 mm×2 mm of the surface was exposed. As pretreatment for forming the light-emitting element over the substrate, the surface of the substrate was washed with water and baked at 200° C. for 1 hour, and then UV ozone treatment was performed for 370 seconds. Then, the substrate was transferred into a vacuum evaporation apparatus where the pressure had been reduced to about $10^{-4}$ Pa, vacuum baking at 170° C. for 30 minutes was performed in a heating chamber of the vacuum evaporation apparatus, and then the substrate was cooled down for about 30 minutes.

Next, the substrate was fixed to a holder provided in the vacuum evaporation apparatus so that a surface of the substrate provided with the anode 1101 was faced downward.

After reducing the pressure of the vacuum evaporation apparatus to $10^{-4}$ Pa, 1,3,5-tri(dibenzothiophen-4-yl)benzene (abbreviation: DBT3P-II) and molybdenum(VI) oxide were deposited by co-evaporation so that the weight ratio of DBT3P-II to molybdenum oxide was 2:1, whereby a hole-injection layer 1107 was formed. The thickness of the hole-injection layer 1107 was 40 nm. Note that the co-evaporation is an evaporation method in which a plurality of different substances are concurrently vaporized from the respective evaporation sources.

Next, a film of 9-phenyl-9H-3-(9-phenyl-9H-carbazol-3-yl)carbazole (abbreviation: PCCP) was formed to a thickness of 20 nm by evaporation, whereby a hole-transport layer 1103 was formed.

Then, on the hole-transport layer 1103, 2'-(3,5-diphenyl)phenyl-dispiro[9H-fluorene-9,9'(10'H)-anthracene-10',9"-(9H)fluorene] (abbreviation: 2mTPDfha) that is the anthracene compound described in Embodiment 1 and tris(5-methyl-3,4-diphenyl-4H-1,2,4-triazolato)iridium(III) (abbreviation: [Ir(Mptz)₃]) were deposited to a thickness of 30 nm by evaporation so that the weight ratio of 2mTPDfha to [Ir(Mptz)₃] was 1:0.06, and then 2-[3-(dibenzothiophen-4-yl)phenyl]-1-phenyl-1H-benzimidazole (abbreviation: mDBTBIm-II) and tris[3-methyl-1-(2-methylphenyl)-5- phenyl-1H-1,2,4-triazolato]iridium(III) (abbreviation: [Ir(Mptz1-mp)₃]) were deposited thereon to a thickness of 10 nm by evaporation so that the weight ratio of mDBTBIm-II to [Ir(Mptz1-mp)₃] was 1:0.06, whereby a light-emitting layer 1104 was formed.

Next, bathophenanthroline (abbreviation: BPhen) was deposited to a thickness of 20 nm by evaporation, whereby an electron-transport layer 1105 was formed.

Furthermore, lithium fluoride was deposited to a thickness of 1 nm on the electron-transport layer 1105 by evaporation, whereby an electron-injection layer 1108 was formed. Lastly, a 200-nm-thick aluminum film was formed as a cathode 1102. Thus, the light-emitting element was manufactured. Note that in all the above evaporation steps, evaporation was performed by a resistance-heating method.

Figure 16:
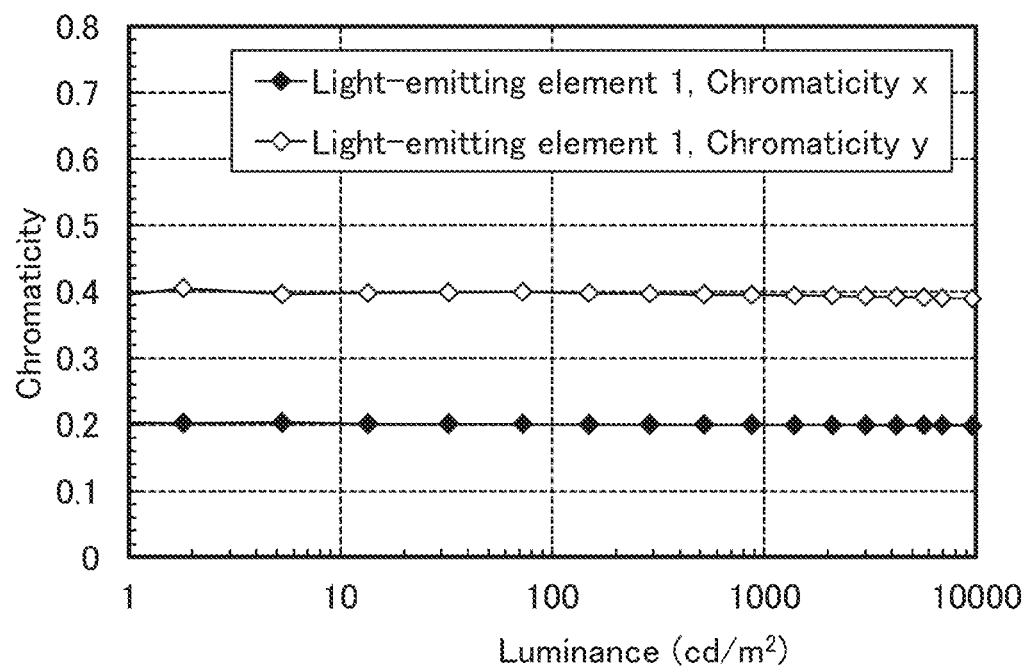
FIG. 16 shows luminance-chromaticity characteristics of the light-emitting element 1 manufactured in Example 4.

The element structure of the manufactured light-emitting element 1 is shown below.

vertical axis represents current (mA) and the horizontal axis represents voltage (V). FIG. 16 shows chromaticity characteristics of the light-emitting element 1. In FIG. 16, the vertical axis represents chromaticity and the horizontal axis represents luminance.

Figure 12:
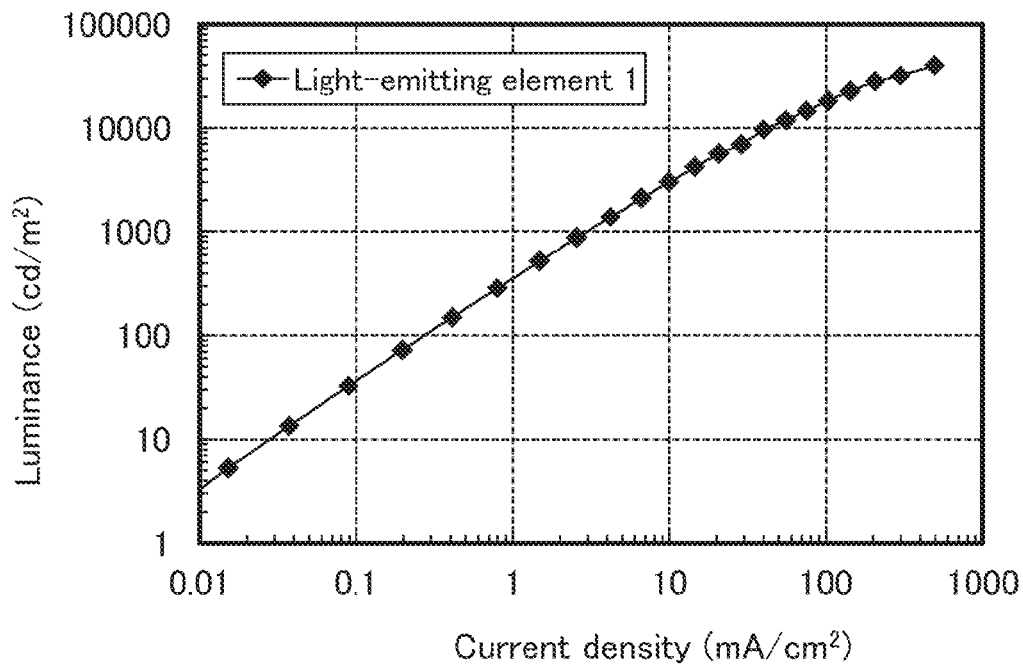
FIG. 12 shows current density-luminance characteristics of a light-emitting element 1 manufactured in Example 4.

FIG. 12 demonstrates that the use of 2mTPDfha (abbreviation) that is one embodiment of the present invention for a light-emitting layer enables a highly efficient element to be obtained. According to FIG. 16, the light-emitting element 1 has a small change in chromaticity that depends on luminance and has excellent carrier balance. In addition, excellent chromaticity can be obtained and 2mTPDfha (abbreviation) that is one embodiment of the present invention is suitable as a host material for an element emitting phosphorescence in the blue region because 2mTPDfha (abbreviation) has a high $T_1$ level. Table 2 shows initial values of main characteristics of the light-emitting element 1 at a luminance of approximately 1000 cd/m².

TABLE 1

| | Functional layer | Hole-injection layer | Hole-transport layer | Light-emitting layer | | Electron-transport layer | Electron-injection layer |
|---|---|---|---|---|---|---|---|
| Light-emitting element 1 | Thickness Structure | 40 nm DBT3P-II:MoOx = 2:1 | 20 nm PCCP | 30 nm 2mTPDfha:[Ir(Mptz)₃] = 1:0.06 | 10 nm mDBTBIm-II: [Ir(Mptz1-mp)₃] = 1:0.06 | 20 nm BPhen | 1 nm LiF |

Anode: 110 nm ITSO
Cathode: 200 nm Al

<<Operation Characteristics of Light-Emitting Element>>

The light-emitting element 1 thus obtained was sealed in a glove box under a nitrogen atmosphere without being exposed to the air. Then, the operation characteristics of the light-emitting element 1 were measured. Note that the measurement was carried out at room temperature (in an atmosphere kept at 25° C.).

TABLE 2

| | Voltage (V) | Current (mA) | Current density (mA/cm²) | Chromaticity (x, y) | Luminance (cd/m²) | Current efficiency (cd/A) | Power efficiency (lm/W) |
|---|---|---|---|---|---|---|---|
| Light-emitting element 1 | 6.2 | 0.10 | 2.6 | (0.20, 0.40) | 880 | 34 | 17 |

The above results demonstrate that the light-emitting element 1 manufactured in this example is a highly efficient element emitting phosphorescence in the blue region.

Example 5

In this example, a light-emitting element 2 that is one embodiment of the present invention is described. Note that the light-emitting element 2 in this example is described with reference to FIG. 7 that is used for describing the light-emitting element 1 in Example 4. Shown below are molecular structures of organic compounds used in this example.

Figure 13:
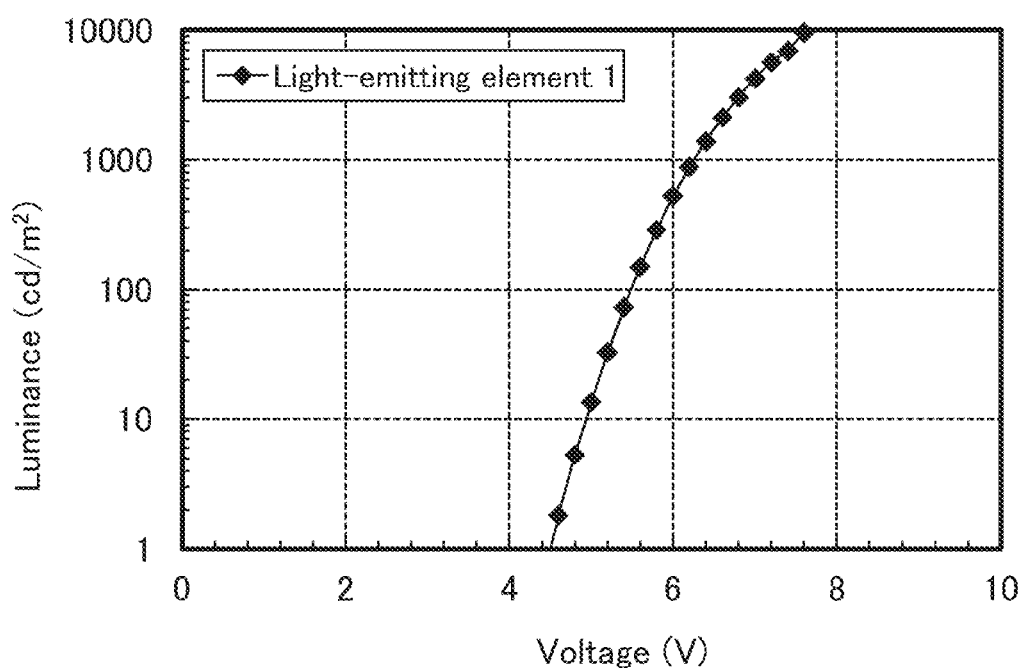
FIG. 13 shows voltage-luminance characteristics of the light-emitting element 1 manufactured in Example 4.
Figure 14:
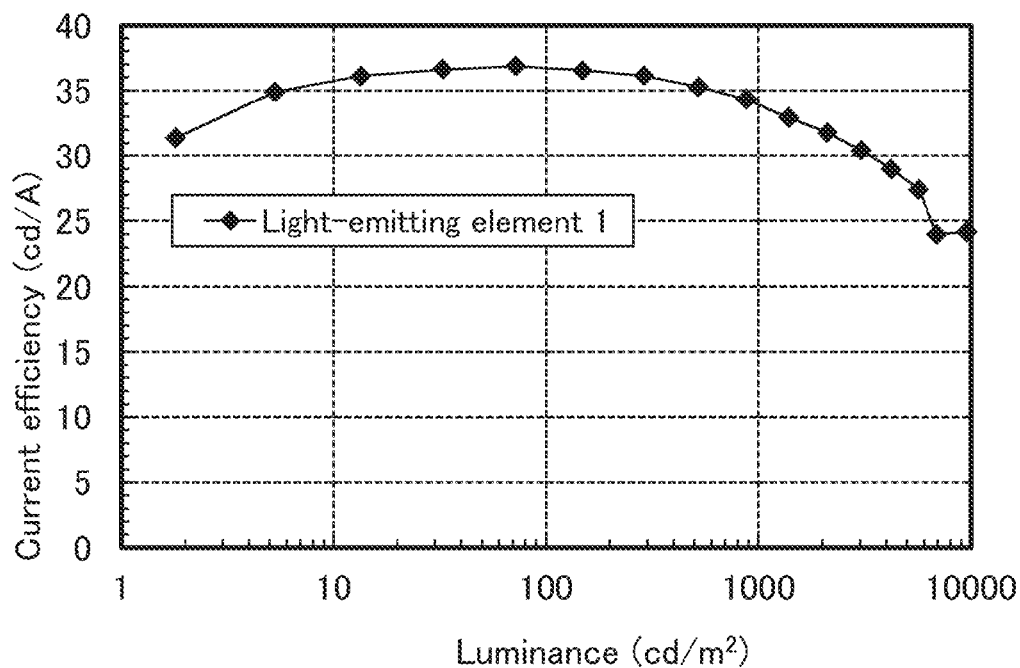
FIG. 14 shows luminance-current efficiency characteristics of the light-emitting element 1 manufactured in Example 4.
Figure 15:
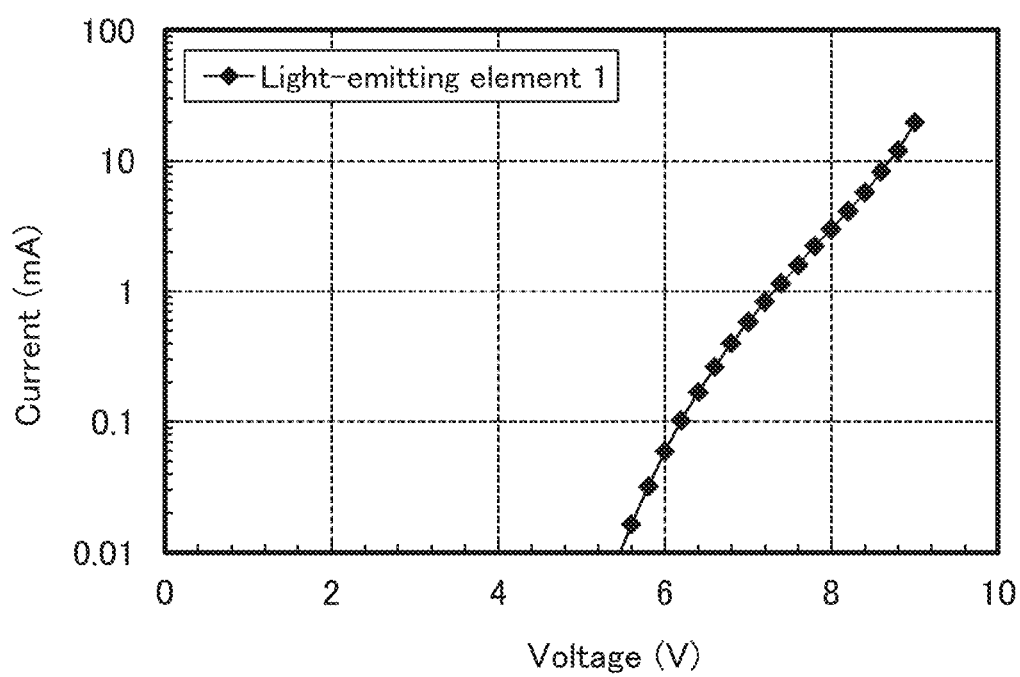
FIG. 15 shows voltage-current characteristics of the light-emitting element 1 manufactured in Example 4.

FIG. 12 shows current density-luminance characteristics of the light-emitting element 1. In FIG. 12, the vertical axis represents luminance (cd/m²) and the horizontal axis represents current density (mA/cm²). FIG. 13 shows voltage-luminance characteristics of the light-emitting element 1. In FIG. 13, the vertical axis represents luminance (cd/m²) and the horizontal axis represents voltage (V). FIG. 14 shows luminance-current efficiency characteristics of the light-emitting element 1. In FIG. 14, the vertical axis represents current efficiency (cd/A) and the horizontal axis represents luminance (cd/m²). FIG. 15 shows voltage-current characteristics of the light-emitting element 1. In FIG. 15, the

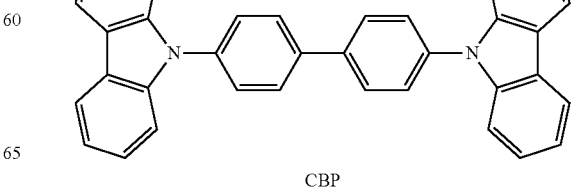

CBP

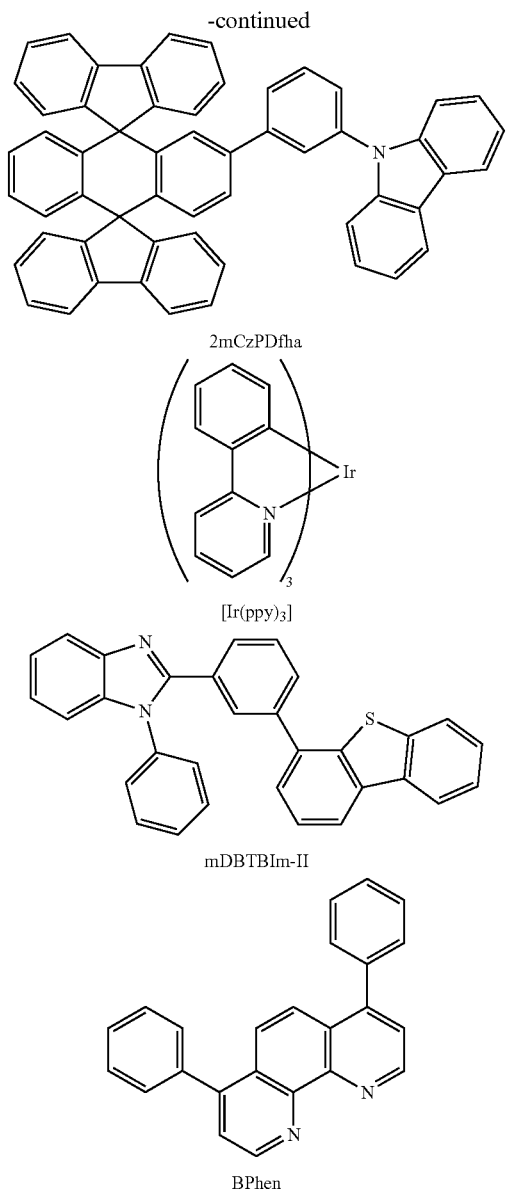

2mCzPDfha

[Ir(ppy)₃]

mDBTBIm-II

BPhen and baked at 200° C. for 1 hour, and then UV ozone treatment was performed for 370 seconds. Then, the substrate was transferred into a vacuum evaporation apparatus where the pressure had been reduced to about $10^{-4}$ Pa, vacuum baking at 170° C. for 30 minutes was performed in a heating chamber of the vacuum evaporation apparatus, and then the substrate was cooled down for about 30 minutes.

Next, the substrate was fixed to a holder provided in the vacuum evaporation apparatus so that a surface of the substrate provided with the anode 1101 was faced downward.

After reducing the pressure of the vacuum evaporation apparatus to $10^{-4}$ Pa, 4,4'-di(N-carbazolyl)biphenyl (abbreviation: CBP) and molybdenum(VI) oxide were deposited by co-evaporation so that the weight ratio of CBP to molybdenum oxide was 2:1, whereby the hole-injection layer 1107 was formed. The thickness of the hole-injection layer 1107 was 60 nm.

Next, 9-(3-{dispiro[9H-fluorene-9,9'(10'H)-anthracene-10',9"-(9H)fluorene]T-yl}phenyl)-9H-carbazole (abbreviation: 2mCzPDfha) that is the anthracene compound represented by Structural Formula (103) was deposited to a thickness of 20 nm by evaporation, whereby the hole-transport layer 1103 was formed.

On the hole-transport layer 1103, 2mCzPDfha (abbreviation) that is the anthracene compound represented by Structural Formula (103) and tris(2-phenylpyridinato)iridium(III) (abbreviation: [Ir(ppy)₃]) were deposited to a thickness of 40 nm by evaporation so that the weight ratio of 2mCzPDfha to [Ir(ppy)₃] was 1:0.06, whereby the light-emitting layer 1104 was formed.

Next, 2-[3-(dibenzothiophen-4-yl)phenyl]-1-phenyl-1H-benzimidazole (abbreviation: mDBTBIm-II) was deposited to a thickness of 15 nm by evaporation, and then bathophenanthroline (abbreviation: BPhen) was deposited to a thickness of 20 nm by evaporation, whereby the electron-transport layer 1105 was formed.

Furthermore, lithium fluoride was deposited to a thickness of 1 nm on the electron-transport layer 1105 by evaporation, whereby an electron-injection layer 1108 was formed. Lastly, a 200-nm-thick aluminum film was formed as the cathode 1102 functioning as a cathode. Thus, the light-emitting element was manufactured. Note that in all the above evaporation steps, evaporation was performed by a resistance-heating method.

The element structure of the manufactured light-emitting element 2 is shown below.

TABLE 3

| | Functional layer | Hole-injection layer | Hole-transport layer | Light-emitting layer | Electron-transport layer | | Electron-injection layer |
|---|---|---|---|---|---|---|---|
| Light-emitting element 2 | Thickness Structure | 60 nm CBP:MoOx = 2:1 | 20 nm 2mCzPDfha | 40 nm 2mCzPDfha:[Ir(ppy)₃] = 1:0.06 | 15 nm mDBTBIm-II | 20 nm BPhen | 1 nm LiF |

Anode: 110 nm ITSO
Cathode: 200 nm Al

<<Manufacture of Light-Emitting Element>>

First, a glass substrate over which a film of indium tin oxide containing silicon (ITSO) with a thickness of 110 nm had been formed as an anode 1101 was prepared. A surface of the ITSO was covered with a polyimide film so that an area of 2 mm×2 mm of the surface was exposed. As pretreatment for forming the light-emitting element over the substrate, the surface of the substrate was washed with water <<Operation Characteristics of Light-Emitting Element>>

The light-emitting element 2 thus obtained was sealed in a glove box under a nitrogen atmosphere without being exposed to the air. Then, the operation characteristics of the light-emitting element 2 were measured. Note that the measurement was carried out at room temperature (in an atmosphere kept at 25° C.).

Figure 17:
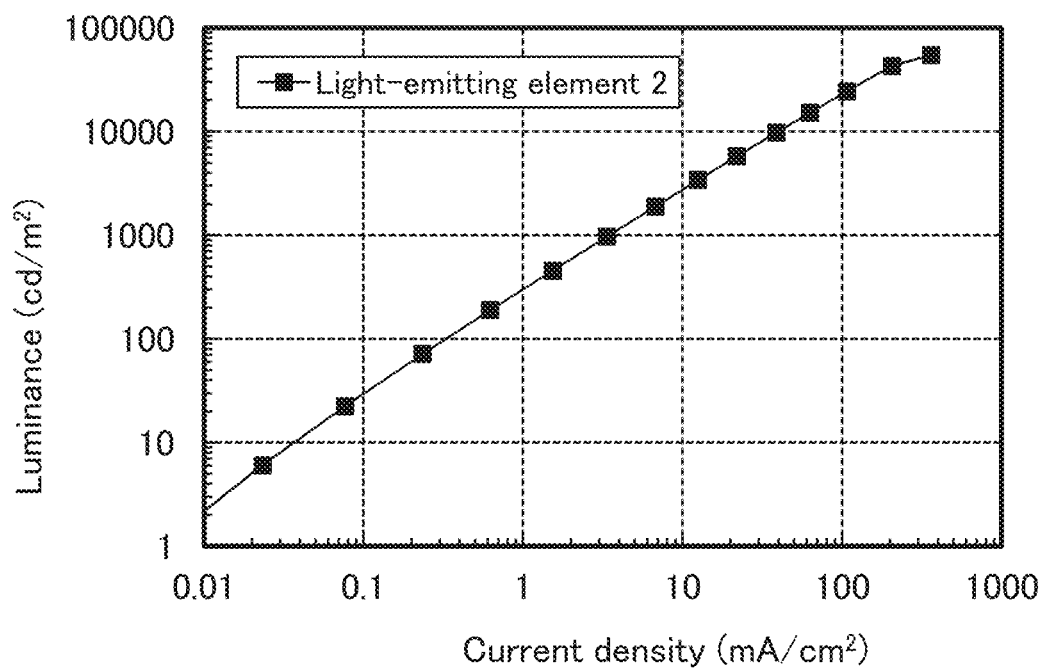
FIG. 17 shows current density-luminance characteristics of a light-emitting element 2 manufactured in Example 5.
Figure 18:
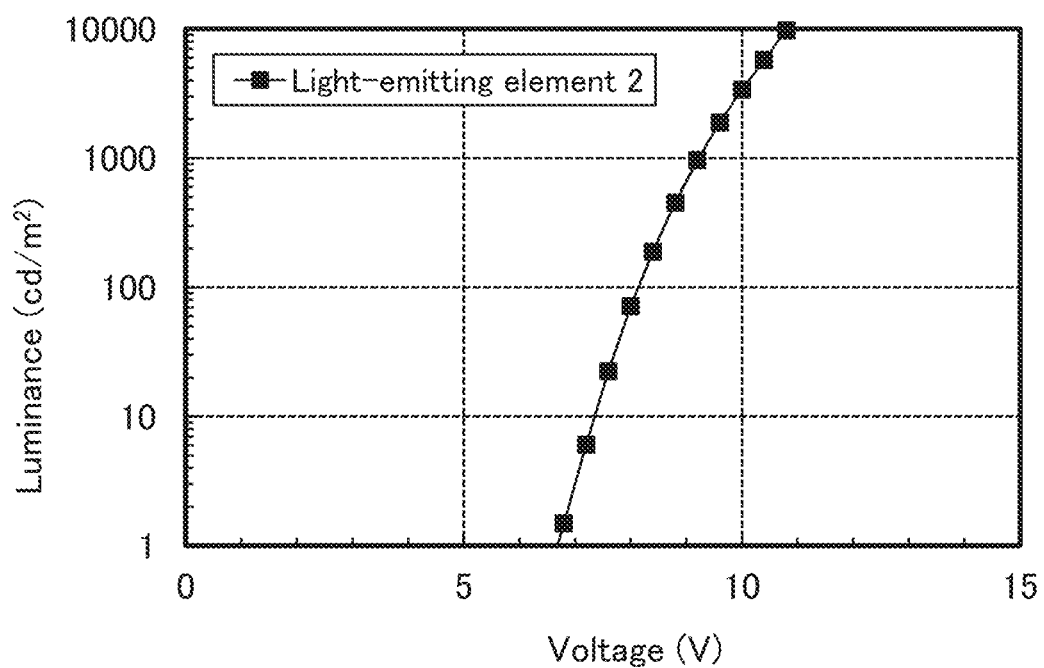
FIG. 18 shows voltage-luminance characteristics of the light-emitting element 2 manufactured in Example 5.
Figure 19:
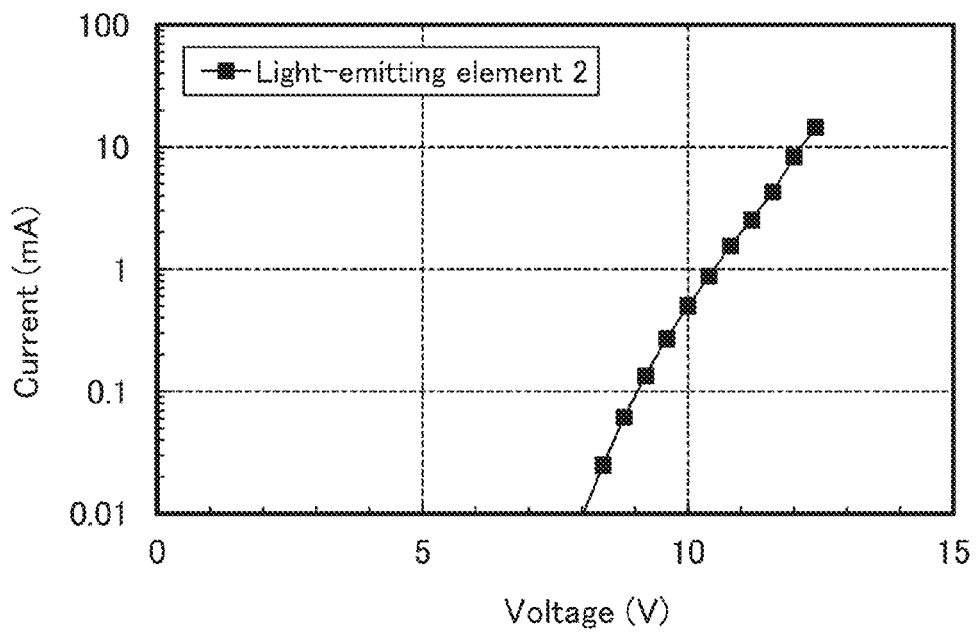
FIG. 19 shows voltage-current characteristics of the light-emitting element 2 manufactured in Example 5.
Figure 20:
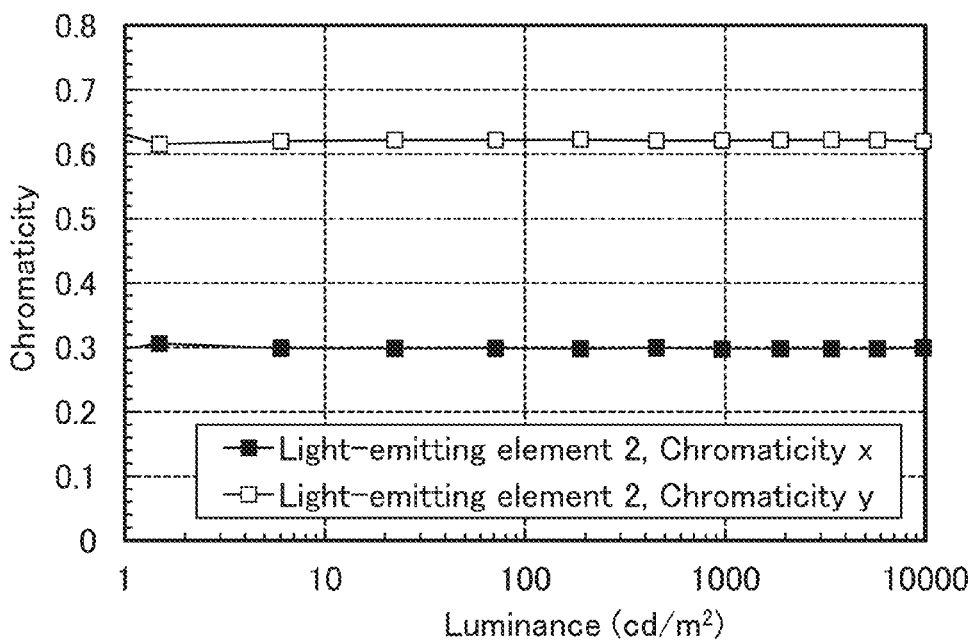
FIG. 20 shows luminance-chromaticity characteristics of the light-emitting element 2 manufactured in Example 5.

FIG. 17 shows current density-luminance characteristics of the light-emitting element 2. In FIG. 17, the vertical axis represents luminance (cd/m$^2$) and the horizontal axis represents current density (mA/cm$^2$). FIG. 18 shows voltage-luminance characteristics of the light-emitting element 2. In FIG. 18, the vertical axis represents luminance (cd/m$^2$) and the horizontal axis represents voltage (V). FIG. 19 shows voltage-current characteristics of the light-emitting element 2. In FIG. 19, the vertical axis represents current (mA) and the horizontal axis represents voltage (V). FIG. 20 shows chromaticity characteristics of the light-emitting element 2. In FIG. 20, the vertical axis represents chromaticity and the horizontal axis represents luminance.

FIG. 17 demonstrates that the use of 2mCzPDfha (abbreviation) that is one embodiment of the present invention for a hole-transport layer and a light-emitting layer enables a highly efficient element to be obtained. According to FIG. 20, the light-emitting element 2 has a small change in chromaticity that depends on luminance and has excellent carrier balance. In addition, excellent chromaticity can be obtained and 2mCzPDfha (abbreviation) that is one embodiment of the present invention is suitable as a host material for an element emitting phosphorescence in the green region because 2mCzPDfha (abbreviation) has a high $T_1$ level. Table 4 shows initial values of main characteristics of the light-emitting element 2 at a luminance of approximately 1000 cd/m$^2$.

TABLE 4

|  | Voltage (V) | Current (mA) | Current density (mA/cm$^2$) | Chromaticity (x, y) | Luminance (cd/m$^2$) | Current efficiency (cd/A) | Power efficiency (lm/W) |
| --- | --- | --- | --- | --- | --- | --- | --- |
| Light-emitting element 2 | 9.2 | 0.13 | 3.4 | (0.30, 0.62) | 970 | 29 | 9.8 |

The above results demonstrate that the light-emitting element 2 manufactured in this example is a highly efficient element emitting light in the green region.

Figure 21:
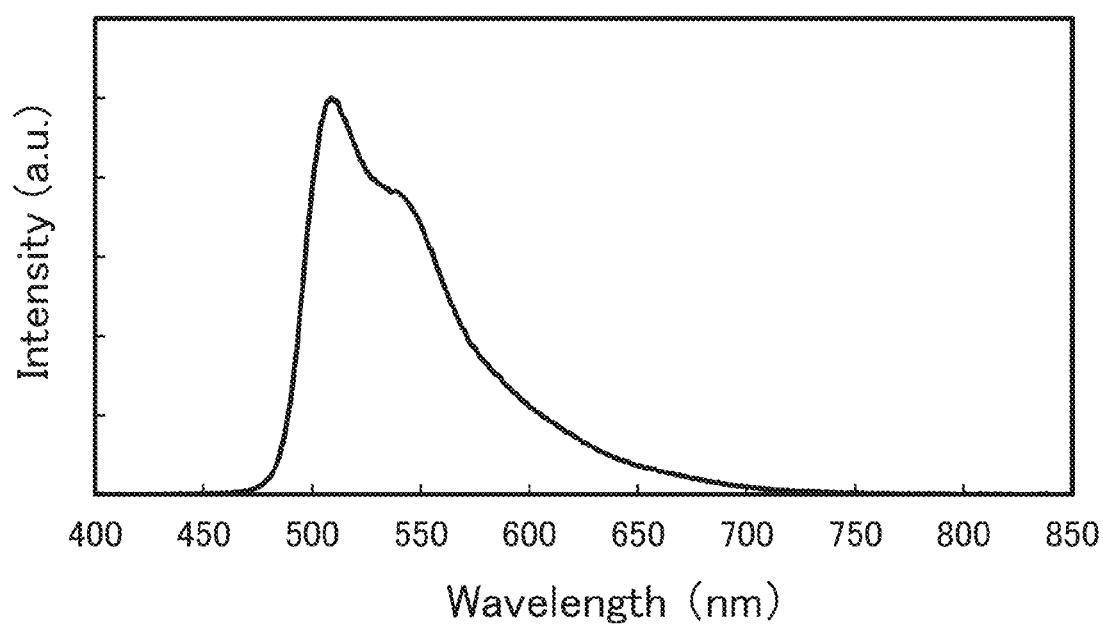
FIG. 21 shows an emission spectrum of the light-emitting element 2 manufactured in Example 5.

FIG. 21 shows an emission spectrum of the light-emitting element 2, which was obtained by applying a current of 0.1 mA to the light-emitting element 2. In FIG. 21, the vertical axis represents emission intensity (arbitrary unit) and the horizontal axis represents wavelength (nm). The emission intensity is shown as a value relative to the greatest emission intensity assumed to be 1. As shown in FIG. 21, the emission spectrum of the light-emitting element 2 is a spectrum that has the maximum emission wavelength at around 509 nm and is derived from [Ir(ppy)$_3$]. This means that the light-emitting element 2 emits green light.

Example 6

In this example, a light-emitting element 3 that is one embodiment of the present invention is described. Note that the light-emitting element 3 in this example is described with reference to FIG. 7 that is used for describing the light-emitting element 1 in Example 4. Shown below are molecular structures of organic compounds used in this example.

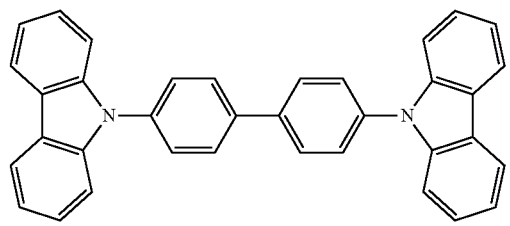

CBP

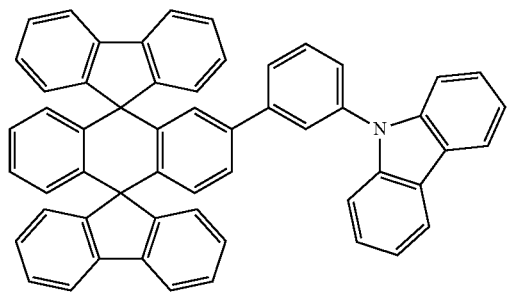

2mCzPDfha

-continued

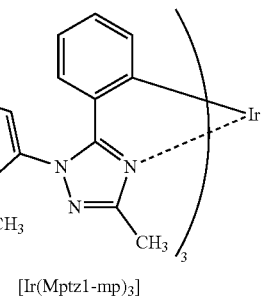

[Ir(Mptz1-mp)$_3$]

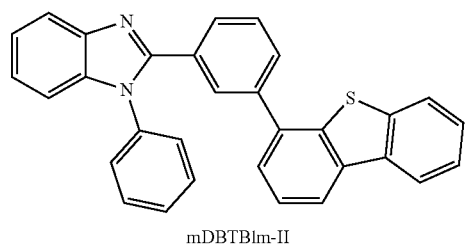

mDBTBIm-II

-continued

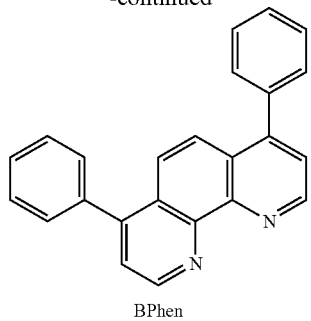
BPhen

<<Manufacture of Light-Emitting Element>>

First, a glass substrate over which a film of indium tin oxide containing silicon (ITSO) with a thickness of 110 nm had been formed as an anode 1101 was prepared. A surface of the ITSO was covered with a polyimide film so that an area of 2 mm×2 mm of the surface was exposed. As pretreatment for forming the light-emitting element over the substrate, the surface of the substrate was washed with water and baked at 200° C. for 1 hour, and then UV ozone treatment was performed for 370 seconds. Then, the substrate was transferred into a vacuum evaporation apparatus where the pressure had been reduced to about $10^{-4}$ Pa, vacuum baking at 170° C. for 30 minutes was performed in a heating chamber of the vacuum evaporation apparatus, and then the substrate was cooled down for about 30 minutes.

Next, the substrate was fixed to a holder provided in the vacuum evaporation apparatus so that a surface of the substrate provided with the anode 1101 was faced downward.

After reducing the pressure of the vacuum evaporation apparatus to $10^{-4}$ Pa, 4,4'-di(N-carbazolyl)biphenyl (abbreviation: CBP) and molybdenum(VI) oxide were deposited by co-evaporation so that the weight ratio of CBP to molybdenum oxide was 2:1, whereby the hole-injection layer 1107 was formed. The thickness of the hole-injection layer 1107 was 60 nm.

Next, 9-(3-{dispiro[9H-fluorene-9,9'(10'H)-anthracene-10',9"-(9H)fluorene]T-yl}phenyl)-9H-carbazole (abbreviation: 2mCzPDfha) that is the anthracene compound represented by Structural Formula (103) was deposited to a thickness of 20 nm by evaporation, whereby the hole-transport layer 1103 was formed.

On the hole-transport layer 1103, 2mCzPDfha (abbreviation) that is the anthracene compound represented by Structural Formula (103) and tris[3-methyl-1-(2-methylphenyl)-5-phenyl-1H-1,2,4-triazolato]iridium(III) (abbreviation: [Ir(Mptz1-mp)$_3$]) were deposited to a thickness of 30 nm by evaporation so that the weight ratio of 2mCzPDfha to [Ir(Mptz1-mp)$_3$] was 1:0.06, and then 2-[3-(dibenzothiophen-4-yl)phenyl]-1-phenyl-1H-benzimidazole (abbreviation: mDBTBIm-II) and Ir(Mptz1-mp)$_3$ (abbreviation) were deposited thereon to a thickness of 10 nm by evaporation so that the weight ratio of mDBTBIm-II to Ir(Mptz1-mp)$_3$ was 1:0.06, whereby the light-emitting layer 1104 was formed.

bathophenanthroline (abbreviation: BPhen) was deposited to a thickness of 15 nm by evaporation, whereby the electron-transport layer 1105 was formed.

Furthermore, lithium fluoride was deposited to a thickness of 1 nm on the electron-transport layer 1105 by evaporation, whereby an electron-injection layer 1108 was formed. Lastly, a 200-nm-thick aluminum film was formed as a cathode 1102 functioning as a cathode. Thus, the light-emitting element was manufactured. Note that in all the above evaporation steps, evaporation was performed by a resistance-heating method.

The element structure of the manufactured light-emitting element 3 is shown below.

TABLE 5

| | Functional layer | Hole-injection layer | Hole-transport layer | Light-emitting layer | | Electron-transport layer | Electron-injection layer |
|---|---|---|---|---|---|---|---|
| Light-emitting element 3 | Thickness Structure | 60 nm CBP:MoOx = 2:1 | 20 nm 2mCzPDfha | 30 nm 2mCzPDfha:[Ir(Mptz1-mp)$_3$] = 1:0.06 | 10 nm mDBTBIm-II:[Ir(Mptz1-mp)$_3$] = 1:0.06 | 15 nm BPhen | 1 nm LiF |

Anode: 110 nm ITSO
Cathode: 200 nm Al

<<Operation Characteristics of Light-Emitting Element>>

The light-emitting element 3 thus obtained was sealed in a glove box under a nitrogen atmosphere without being exposed to the air. Then, the operation characteristics of the light-emitting element 3 were measured. Note that the measurement was carried out at room temperature (in an atmosphere kept at 25° C.).

Figure 22:
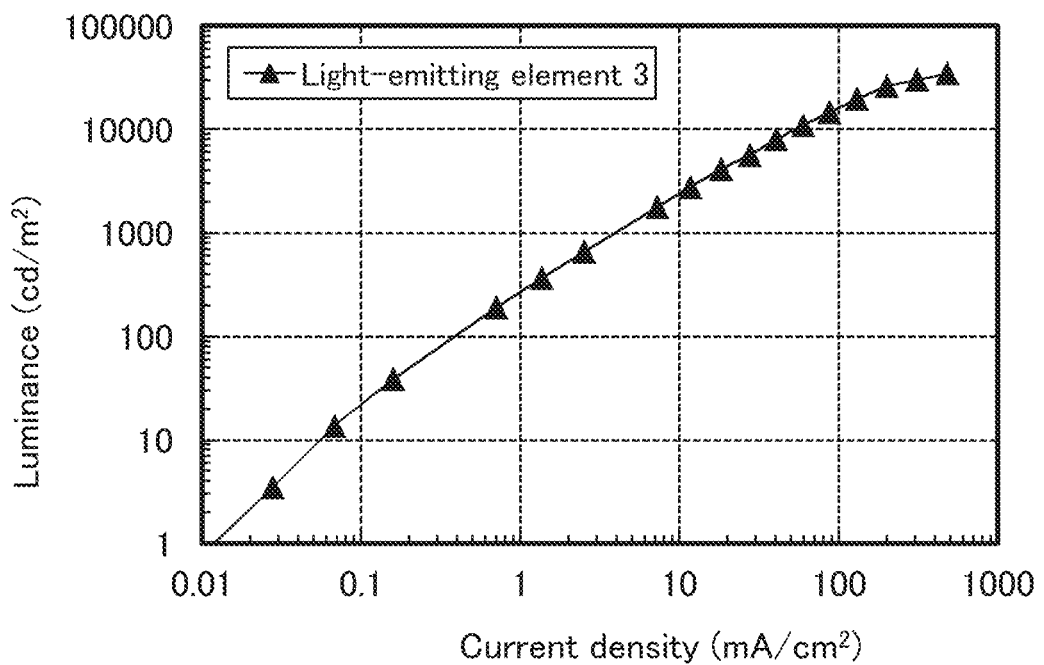
FIG. 22 shows current density-luminance characteristics of a light-emitting element 3 manufactured in Example 6.
Figure 23:
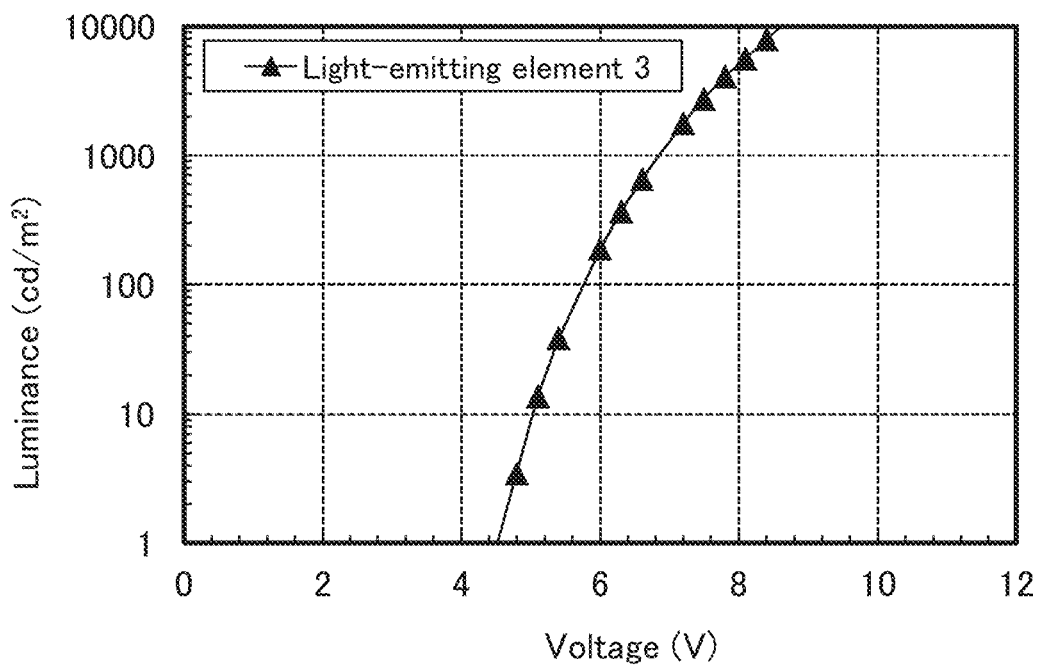
FIG. 23 shows voltage-luminance characteristics of the light-emitting element 3 manufactured in Example 6.
Figure 24:
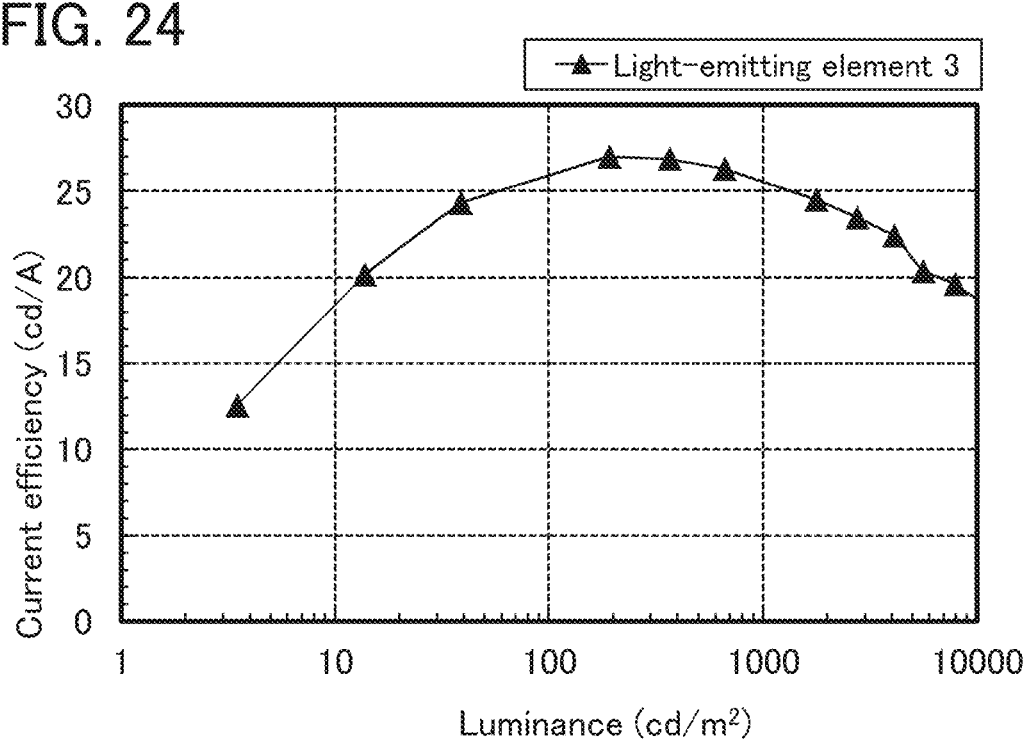
FIG. 24 shows luminance-current efficiency characteristics of the light-emitting element 3 manufactured in Example 6.
Figure 25:
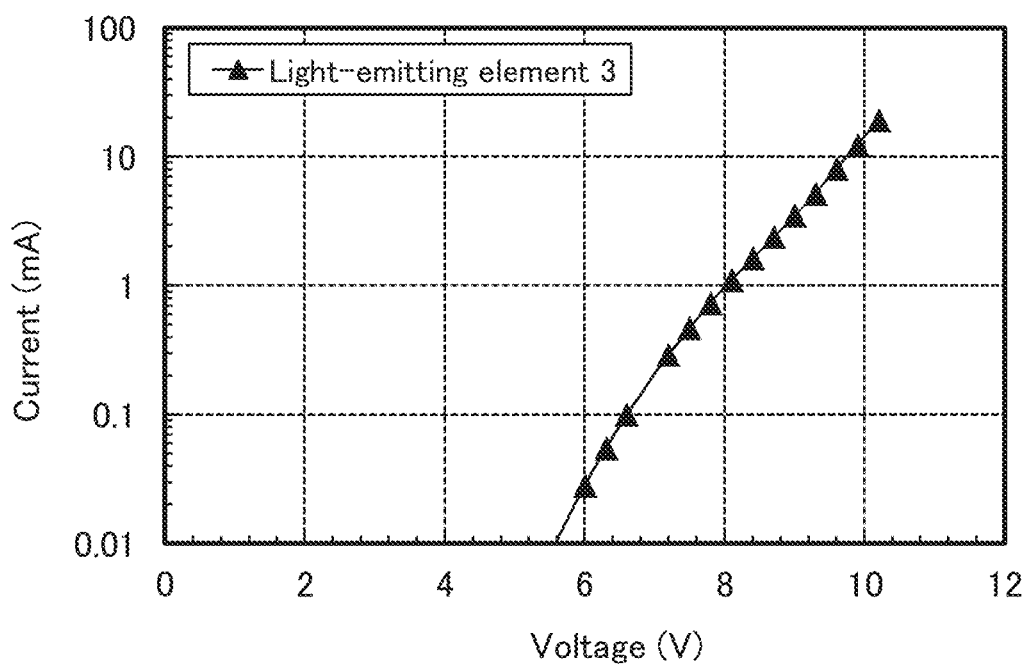
FIG. 25 shows voltage-current characteristics of the light-emitting element 3 manufactured in Example 6.
Figure 26:
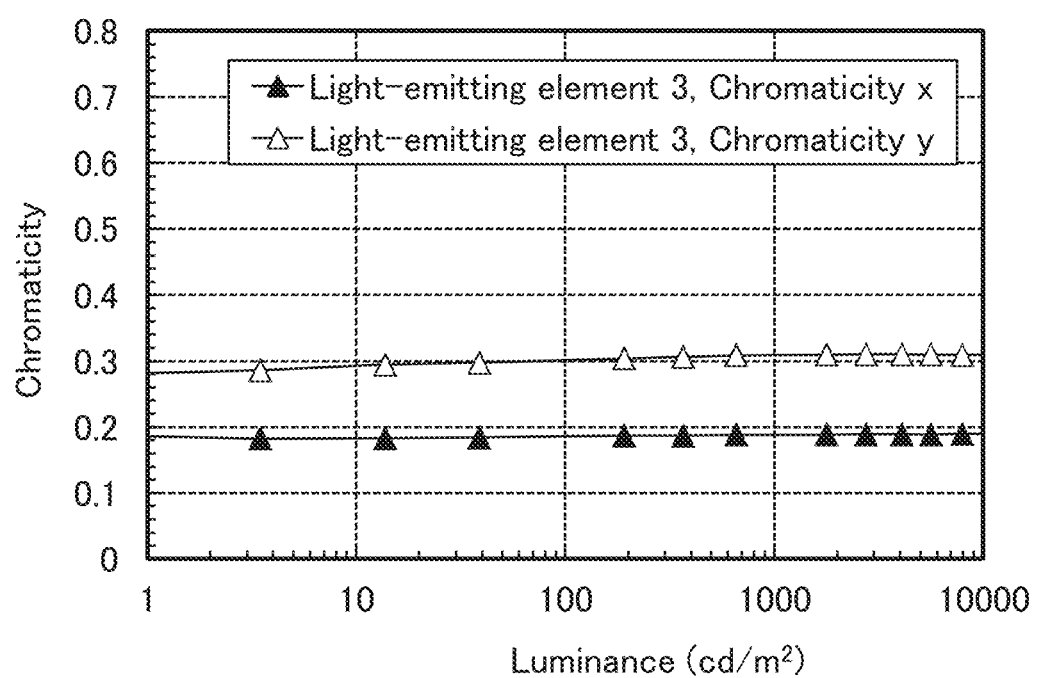
FIG. 26 shows luminance-chromaticity characteristics of the light-emitting element 3 manufactured in Example 6.

FIG. 22 shows current density-luminance characteristics of the light-emitting element 3. In FIG. 22, the vertical axis represents luminance (cd/m$^2$) and the horizontal axis represents current density (mA/cm$^2$). FIG. 23 shows voltage-luminance characteristics of the light-emitting element 3. In FIG. 23, the vertical axis represents luminance (cd/m$^2$) and the horizontal axis represents voltage (V). FIG. 24 shows luminance-current efficiency characteristics of the light-emitting element 3. In FIG. 24, the vertical axis represents current efficiency (cd/A) and the horizontal axis represents luminance (cd/m$^2$). FIG. 25 shows voltage-current characteristics of the light-emitting element 3. In FIG. 25, the vertical axis represents current (mA) and the horizontal axis represents voltage (V). FIG. 26 shows chromaticity characteristics of the light-emitting element 3. In FIG. 26, the vertical axis represents chromaticity and the horizontal axis represents luminance.

FIG. 22 demonstrates that the use of 2mCzPDfha (abbreviation) that is one embodiment of the present invention for a hole-transport layer and a light-emitting layer enables a highly efficient element to be obtained. According to FIG. 26, the light-emitting element 2 has a small change in chromaticity that depends on luminance and has excellent carrier balance. In addition, excellent chromaticity can be obtained and 2mCzPDfha (abbreviation) that is one embodiment of the present invention is suitable as a host material for an element emitting phosphorescence in the blue region because 2mCzPDfha (abbreviation) has a high $T_1$ level. Table 6 shows initial values of main characteristics of the light-emitting element 3 at a luminance of approximately 1000 cd/m$^2$.

TABLE 6

| | Voltage (V) | Current (mA) | Current density (mA/cm$^2$) | Chromaticity (x, y) | Luminance (cd/m$^2$) | Current efficiency (cd/A) | Power efficiency (lm/W) |
|---|---|---|---|---|---|---|---|
| Light-emitting element 3 | 6.6 | 0.10 | 2.5 | (0.19, 0.31) | 660 | 26 | 13 |

The above results demonstrate that the light-emitting element 3 manufactured in this example is a blue light-emitting element with high efficiency.

Figure 27:
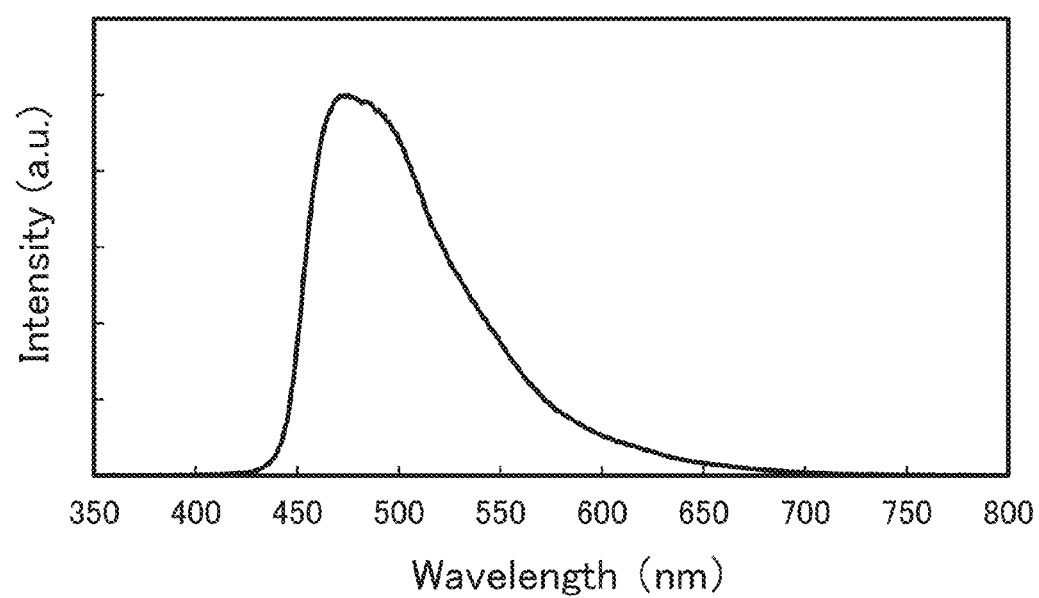
FIG. 27 shows an emission spectrum of the light-emitting element 3 manufactured in Example 6.

FIG. 27 shows an emission spectrum of the light-emitting element 3, which was obtained by applying a current of 0.1 mA to the light-emitting element 3. In FIG. 27, the vertical axis represents emission intensity (arbitrary unit) and the horizontal axis represents wavelength (nm). The emission intensity is shown as a value relative to the greatest emission intensity assumed to be 1. As shown in FIG. 27, the emission spectrum of the light-emitting element 3 has the maximum emission wavelength at around 472 nm. This means that the light-emitting element 3 emits blue light.

Example 7

In this example, the HOMO levels, LUMO levels, $T_1$ levels, and glass-transition temperatures (Tg) of the anthracene compounds 2mTPDfha (abbreviation) (Structural Formula (100)) and 2mCzPDfha (abbreviation) (Structural Formula (103)), each of which is one embodiment of the present invention represented by General Formula (G1) in Embodiment 1, were measured. The HOMO level, LUMO level, $T_1$ level, and glass-transition temperature (Tg) of 2tBuDfha (abbreviation) were also measured as a comparative example. Table 7 shows measurement results. Note that shown below is the structural formula of 2tBuDfha (abbreviation).

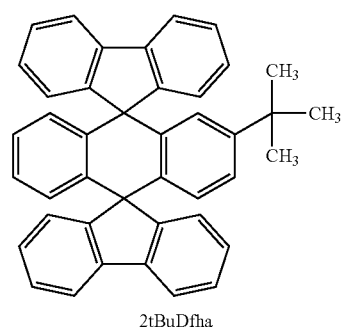

2tBuDfha

The HOMO levels of thin films of 2mCzPDfha (abbreviation) and 2mTPDfha (abbreviation) were measured with AC-2 and AC-3 (each produced by Riken Keiki, Co., Ltd.), respectively. The LUMO levels of 2mCzPDfha (abbreviation) and 2mTPDfha (abbreviation) were each obtained as follows: an energy gap (Bg, ΔE) was obtained from an absorption spectrum of the thin film, and the LUMO level was obtained by the measured HOMO level and the obtained energy gap.

The $T_1$ levels of 2mCzPDfha (abbreviation) and 2mTPDfha (abbreviation) were each obtained as follows: the thin film was cooled down to 10 K and then irradiated with excitation light to obtain an emission spectrum, which was time-resolved to find a phosphorescent peak, and the value of the peak on the shortest wavelength side of the phosphorescent was converted into an energy value.

The glass-transition temperatures of 2mCzPDfha (abbreviation) and 2mTPDfha (abbreviation) were each measured with a differential scanning calorimeter (Pyris 1 DSC, produced by PerkinElmer, Inc.).

TABLE 7

| | Solution (CV) [eV] | | Thin film (AC-2 or AC-3) [eV] | | | $T_1$ level | Tg |
|---|---|---|---|---|---|---|---|
| Compound | HOMO | LUMO | HOMO | LUMO | ΔE | [nm] | [° C.] |
| (100) 2mTPDfha | ND | −2.20 | −6.06 | −2.17 | 3.89 | 453 | 169 |
| (103) 2mCzPDfha | −5.90 | −2.16 | −5.91 | −2.41 | 3.50 | — | 185 |
| 2tBuDfha | ND | ND | −6.58 | −2.69 | 3.89 | — | 151 |

It was found that the anthracene compounds of the present invention have deep HOMO levels. It was also found that the anthracene compounds have relatively shallow LUMO levels because of their wide Bg.

It was also found that the anthracene compounds each have a high $T_1$ level and can be used as a host material for a material emitting light in the visible range. The anthracene compounds can be suitably used for an element emitting phosphorescence with a short wavelength, particularly phosphorescence in the blue or green region. In particular, 2mTPDfha (abbreviation) has Bg as wide as that of 2tBuDfha (abbreviation) and has a particularly high $S_1$ level.

Table 7 also shows oxidation potentials (HOMO) and reduction potentials (LUMO) of solutions of 2mTPDfha (abbreviation) and 2mCzPDfha (abbreviation), which were obtained in the CV measurement described in Example 1 and Example 2. Clear peaks were not detected when scan was performed to 1.5 V on the oxidation side and to −3 V on the reduction side. This is probably because a Dfha skeleton is difficult to oxidize and reduce. This indicates that when an aryl group is bonded to the 2-position of an anthracene skeleton as in the anthracene compound of the present invention, the Dfha skeleton is easily oxidized or reduced. Thus, 2mTPDfha (abbreviation) and 2mCzPDfha (abbreviation) probably have higher carrier-transport properties and drive voltages of an element than 2tBuDfha (abbreviation) and Dfha.

It was also found that the anthracene compounds of the present invention each have high Tg and thus have excellent heat resistance. This is probably because the Dfha (9,10-di (fluoren-9,9'-diyl)-9,10-anthracene) skeleton itself has high Tg. It was also found that the anthracene compounds of the present invention in each of which the aryl group is bonded to the Dfha skeleton have Tg much higher than that of 2tBuDfha (abbreviation) in which only an alkyl group is bonded. Thus, it is thought that when the anthracene compounds of the present invention are used for an element, the element can have excellent heat resistance.

The above indicates that the anthracene compounds of the present invention can be suitably used for a light-emitting element because of their deep HOMO levels, shallow LUMO levels, high $T_1$ levels, and excellent heat resistance. The anthracene compounds of the present invention are each thought to be suitable as a host material for an element emitting phosphorescence with a short wavelength, particularly phosphorescence in the blue or green region.

A material with a high $T_1$ level generally has a problem in that the heat resistance (Tg) is low because of a small molecular weight. It can be said that, in contrast, the anthracene compounds of the present invention each have excellent heat resistance as well as a high $T_1$ level.

Example 8

In this example, the HOMO levels, LUMO levels, and $T_1$ levels of 2mTPDfha (abbreviation) (Structural Formula (100)) and 2mCzPDfha (abbreviation) (Structural Formula (103)), each of which is the anthracene compound of one embodiment of the present invention represented by General Formula (G1) in Embodiment 1, were calculated. The HOMO levels, LUMO levels, and $T_1$ levels of 2tBuDfha (abbreviation), 2CzPDfha (abbreviation), and Dfha (abbreviation) were also calculated as comparative examples. Shown below are the structural formulae of the compounds.

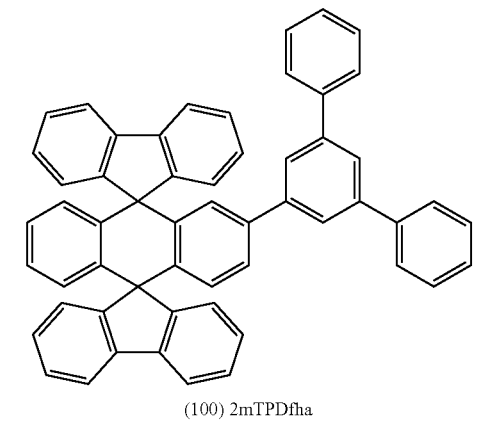

(100) 2mTPDfha

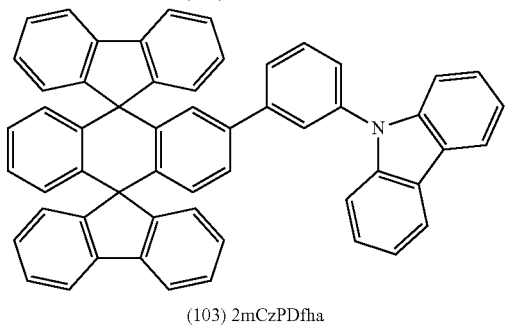

(103) 2mCzPDfha

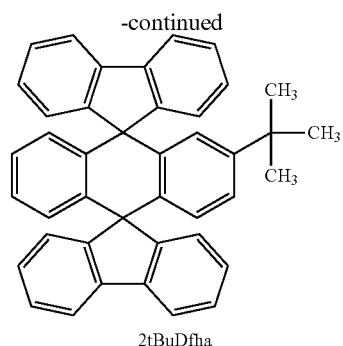

2tBuDfha

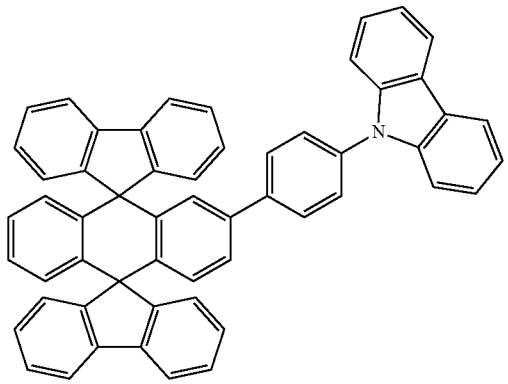

2CzPDfha

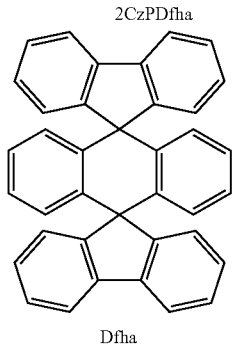

Dfha

The calculating method is described below. Note that Gaussian 09 was used as the quantum chemistry computational program. A high performance computer (Altix 4700, manufactured by SGI Japan, Ltd.) was used for the calculations.

First, the most stable structure in the singlet state was calculated using the density functional theory. As a basis function, 6-311 (a basis function of a triple-split valence basis set using three contraction functions for each valence orbital) was applied to all the atoms. By the above basis function, for example, 1s to 3s orbitals are considered in the case of hydrogen atoms, while 1s to 4s and 2p to 4p orbitals are considered in the case of carbon atoms. Furthermore, to improve calculation accuracy, the p function and the d function as polarization basis sets were added respectively to hydrogen atoms and atoms other than hydrogen atoms. As a functional, B3LYP was used. In addition, the LUMO level and HOMO level of the structure were each calculated.

Next, the most stable structure in the triplet state was calculated. The energy of the $T_1$ level was calculated from an energy difference between the most stable structures in the singlet state and in the triplet state. As a basis function, 6-311G (d, p) was used. As a functional, B3LYP was used.

The calculation results are shown in Table 8.

TABLE 8

| Compound | HOMO [eV] | LUMO [eV] | ΔE [eV] | T₁ level [nm] |
|---|---|---|---|---|
| (100) 2mTPDfha | −5.93 | −1.17 | 4.76 | 442 |
| (103) 2mCzPDfha | −5.53 | −1.23 | 4.30 | 443 |
| 2tBuDfha | −5.92 | −1.13 | 4.79 | 441 |
| 2CzPDfha | −5.51 | −1.22 | 4.28 | 461 |
| Dfha | −5.96 | −1.14 | 4.82 | 441 |

The above results indicate that the Dfha (9,10-di(fluoren-9,9'-diyl)-9,10-anthracene) skeleton itself has an extremely high T₁ level. The above results also indicate that 2mTPDfha (abbreviation) and 2mCzPDfha (abbreviation), each of which is the anthracene compound of one embodiment of the present invention and in each of which a substituent is bonded to the 2-position of the anthracene skeleton, also have extremely high T₁ levels. The above results also indicate that 2mCzPDfha (abbreviation), in which a carbazol-9-yl group is bonded via m-phenylene to the substituent bonded to the 2-position of the anthracene skeleton, has a higher T₁ level than 2CzPDfha (abbreviation), in which a carbazol-9-yl group is bonded via p-phenylene to the substituent. Thus, 2mCzPDfha (abbreviation) is more suitable than 2CzPDfha (abbreviation) as a host material for an element emitting phosphorescence with a shorter wavelength.

Figure 28A:
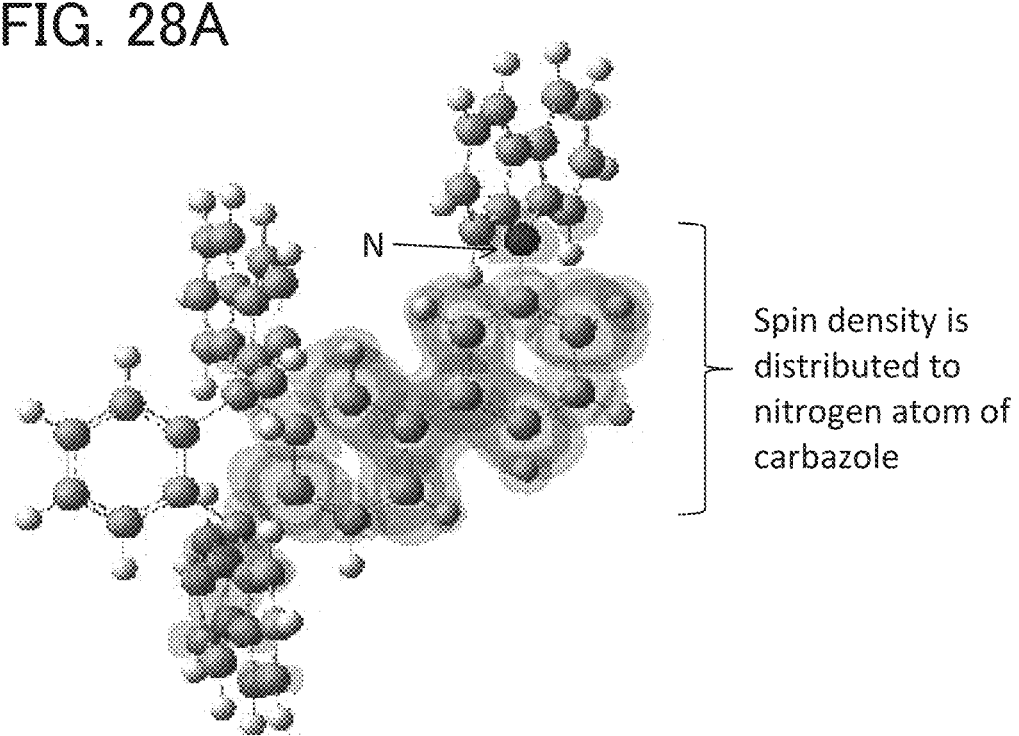
FIGS. 28A and 28B show calculation results in Example 8.
Figure 28B:
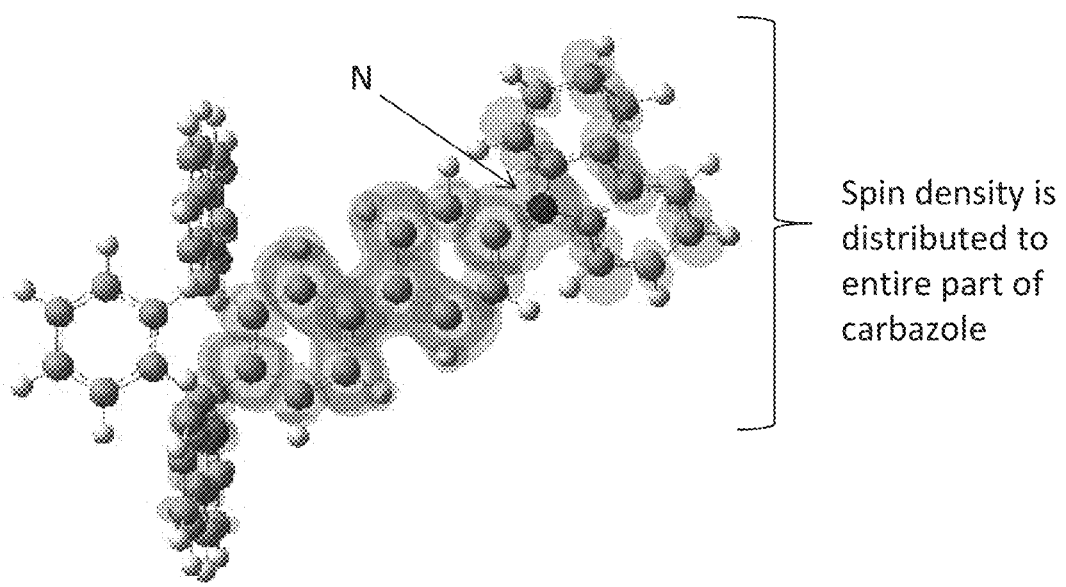

This is probably because of a difference in spin density distribution. FIGS. 28A and 28B show spin density distributions of 2mCzPDfha (abbreviation) and 2CzPDfha (abbreviation), respectively, which were calculated by the above-described method.

In 2mCzPDfha (abbreviation), as shown in FIG. 28A, the spin density is distributed from fluorene bonded to the 9-position of anthracene to the vicinity of a nitrogen atom of carbazole bonded to phenylene through a benzene skeleton on the 2-position side to the 4-position side of the anthracene and phenylene bonded to the 2-position of the anthracene.

The spin density is distributed to the entire part of carbazole in 2CzPDfha (abbreviation) as shown in FIG. 28B in contrast to 2mCzPDfha (abbreviation), in which the spin density is distributed to the nitrogen atom of carbazole. Thus, 2mCzPDfha (abbreviation) is more unstable in terms of energy and has a higher T₁ level than 2CzPDfha (abbreviation).

Thus, 2mTPDfha (abbreviation) and 2mCzPDfha (abbreviation), in each of which the substituent is bonded to the 2-position of the anthracene skeleton at the meta-position of the benzene ring in the substituent, have T₁ levels as high as those of 2tBuDfha (abbreviation) and Dfha (abbreviation).

A comparative light-emitting element 1, a comparative light-emitting element 2, and a comparative light-emitting element 3, in each of which 2tBuDfha (abbreviation) was used for a light-emitting layer, are described below with reference to FIG. 7. Shown below are molecular structures of organic compounds used in the comparative light-emitting element 1.

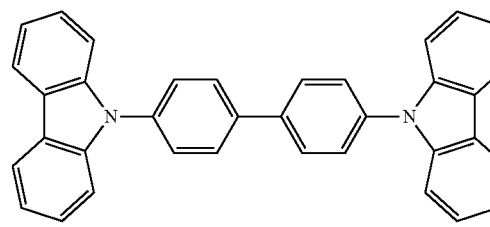
CBP

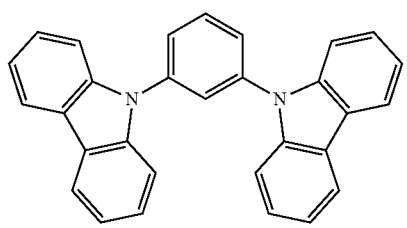
mCP

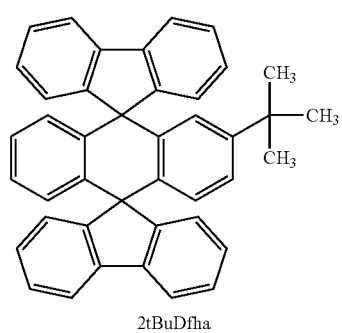 [SMILES: CC(C)(C)c1ccc2c(c1)C1(c3ccccc3-c3ccccc31)c1ccccc1C21c2ccccc2-c2ccccc21]
2tBuDfha

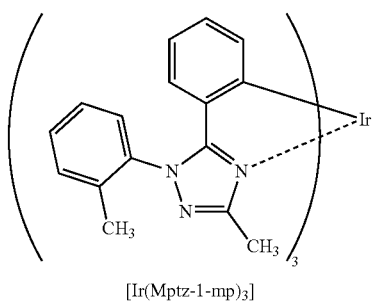
[Ir(Mptz-1-mp)₃]

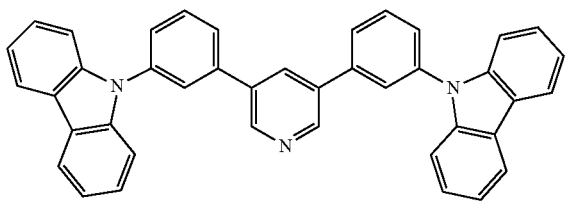
35DCzPPy

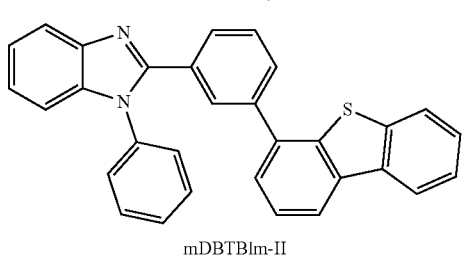
mDBTBIm-II

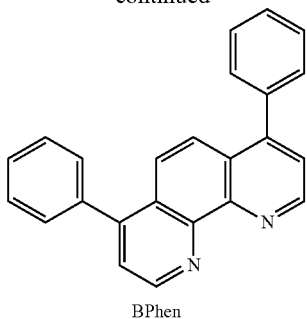

BPhen

<<Manufacture of Comparative Light-Emitting Element 1>>

First, a glass substrate over which a film of indium tin oxide containing silicon (ITSO) with a thickness of 110 nm had been formed as the anode 1101 was prepared. A surface of the ITSO was covered with a polyimide film so that an area of 2 mm×2 mm of the surface was exposed. As pretreatment for forming the light-emitting element over the substrate, the surface of the substrate was washed with water and baked at 200° C. for 1 hour, and then UV ozone treatment was performed for 370 seconds. Then, the substrate was transferred into a vacuum evaporation apparatus where the pressure had been reduced to about $10^{-4}$ Pa, vacuum baking at 170° C. for 30 minutes was performed in a heating chamber of the vacuum evaporation apparatus, and then the substrate was cooled down for about 30 minutes.

Next, the substrate was fixed to a holder provided in the vacuum evaporation apparatus so that a surface of the substrate provided with the anode 1101 was faced downward.

After reducing the pressure of the vacuum evaporation apparatus to $10^{-4}$ Pa, 4,4'-di(N-carbazolyl)biphenyl (abbreviation: CBP) and molybdenum(VI) oxide were deposited by co-evaporation so that the weight ratio of CBP to molybdenum oxide was 2:1, whereby the hole-injection layer 1107 was formed. The thickness of the hole-injection layer 1107 was 60 nm. Note that the co-evaporation is an evaporation method in which a plurality of different substances are concurrently vaporized from the respective evaporation sources.

Next, a film of 1,3-bis(N-carbazolyl)benzene (abbreviation: mCP) was formed to a thickness of 20 nm by evaporation, whereby the hole-transport layer 1103 was formed.

Then, on the hole-transport layer 1103, 2tBuDfha that was the anthracene compound used as the comparative example and tris[3-methyl-1-(2-methylphenyl)-5-phenyl-1H-1,2,4-triazolato]iridium(III) (abbreviation: Ir(Mptz1-mp)₃) were deposited to a thickness of 30 nm by evaporation so that the weight ratio of 2tBuDfha to Ir(Mptz1-mp)₃ was 1:0.06, and then 2-[3-(dibenzothiophen-4-yl)phenyl]-1-phenyl-1H-benzimidazole (abbreviation: mDBTBIm-II) and tris[3-methyl-1-(2-methylphenyl)-5-phenyl-1H-1,2,4-triazolato]iridium (III) (abbreviation: [Ir(Mptz1-mp)₃]) were deposited thereon to a thickness of 10 nm by evaporation so that the weight ratio of mDBTBIm-II to [Ir(Mptz1-mp)₃] was 1:0.06, whereby the light-emitting layer 1104 was formed.

Next, bathophenanthroline (abbreviation: BPhen) was deposited to a thickness of 15 nm by evaporation, whereby the electron-transport layer 1105 was formed.

Furthermore, lithium fluoride was deposited thereon to a thickness of 1 nm on the electron-transport layer 1105 by evaporation, whereby an electron-injection layer 1108 was formed. Lastly, a 200-nm-thick aluminum film was formed as the cathode 1102. Thus, the light-emitting element was manufactured. Note that in all the above evaporation steps, evaporation was performed by a resistance-heating method.

The element structure of the manufactured comparative light-emitting element 1 is shown below.

TABLE 9

| | Functional layer | Hole-injection layer | Hole-transport layer | Light-emitting layer | | Electron-transport layer | Electron-injection layer |
|---|---|---|---|---|---|---|---|
| Comparative light-emitting element 1 | Thickness Structure | 60 nm CBP:MoOx = 2:1 | 20 nm mCP | 30 nm 2tBuDfha:[Ir(Mptz1-mp)₃] = 1:0.06 | 10 nm mDBTBIm-II:[Ir(Mptz1-mp)₃] = 1:0.06 | 15 nm BPhen | 1 nm LiF |

Anode: 110 nm ITSO
Cathode: 200 nm Al

<<Manufacture of Comparative Light-Emitting Element 2>>

Components other than the light-emitting layer 1104 were manufactured in the same manner as the comparative light-emitting element 1. The light-emitting layer 1104 was formed as follows: on the hole-transport layer 1103, 2tBuDfha (abbreviation) that was the anthracene compound used as the comparative example, 3,5-bis[3-(9H-carbazol-9-yl)phenyl]pyridine (abbreviation: 35DCzPPy), and tris[3-methyl-1-(2-methylphenyl)-5-phenyl-1H-1,2,4-triazolato]iridium(III) (abbreviation: [Ir(Mptz1-mp)₃]) were deposited to a thickness of 30 nm by evaporation so that the weight ratio of 2tBuDfha to 35DCzPPy and [Ir(Mptz1-mp)₃] was 1:0.3:0.06, and then 2-[3-(dibenzothiophen-4-yl)phenyl]-1-phenyl-1H-benzimidazole (abbreviation: mDBTBIm-II) and tris[3-methyl-1-(2-methylphenyl)-5-phenyl-1H-1,2,4-triazolato]iridium(III) (abbreviation: [Ir(Mptz1-mp)₃]) were deposited thereon to a thickness of 10 nm by evaporation so that the weight ratio of mDBTBIm-II to [Ir(Mptz1-mp)₃] was 1:0.06.

The element structure of the manufactured comparative light-emitting element 2 is shown below.

TABLE 10

| | Functional layer | Hole-injection layer | Hole-transport layer | Light-emitting layer | | Electron-transport layer | Electron-injection layer |
|---|---|---|---|---|---|---|---|
| Comparative light-emitting element 2 | Thickness Structure | 60 nm CBP:MoOx = 2:1 | 20 nm mCP | 30 nm 2tBuDfha:35DCzPPy:[Ir(Mptz1-mp)$_3$] = 1:0.3:0.06 | 10 nm mDBTBIm-II:[Ir(Mptz1-mp)$_3$] = 1:0.06 | 15 nm BPhen | 1 nm LiF |

Anode: 110 nm ITSO
Cathode: 200 nm Al

<<Manufacture of Comparative Light-Emitting Element 3>>

The anode 1101 and the hole-injection layer 1107 were formed in the same manner as the comparative light-emitting element 1.

On the hole-injection layer 1107, 2tBuDfha (abbreviation) that was the anthracene compound used as the comparative example was deposited to a thickness of 20 nm by evaporation, whereby the hole-transport layer 1103 was formed.

On the hole-transport layer 1103, 2tBuDfha that was the anthracene compound of the comparative example and tris (2-phenylpyridinato)iridium(III) (abbreviation: [Ir(ppy)$_3$]) were deposited to a thickness of 40 nm by evaporation so that the weight ratio of 2tBuDfha to [Ir(ppy)$_3$] was 1:0.06, whereby the light-emitting layer 1104 was formed.

Next, 2-[3-(dibenzothiophen-4-yl)phenyl]-1-phenyl-1H-benzimidazole (abbreviation: mDBTBIm-II) was deposited to a thickness of 15 nm by evaporation, and then bathophenanthroline (abbreviation: BPhen) was deposited thereon to a thickness of 20 nm by evaporation, whereby the electron-transport layer 1105 was formed.

Furthermore, lithium fluoride was deposited to a thickness of 1 nm on the electron-transport layer 1105 by evaporation, whereby the electron-injection layer 1108 was formed. Lastly, a 200-nm-thick aluminum film was formed as the cathode 1102. Thus, the light-emitting element was manufactured. Note that in all the above evaporation steps, evaporation was performed by a resistance-heating method.

The element structure of the manufactured comparative light-emitting element 3 is shown below.

Figure 29:
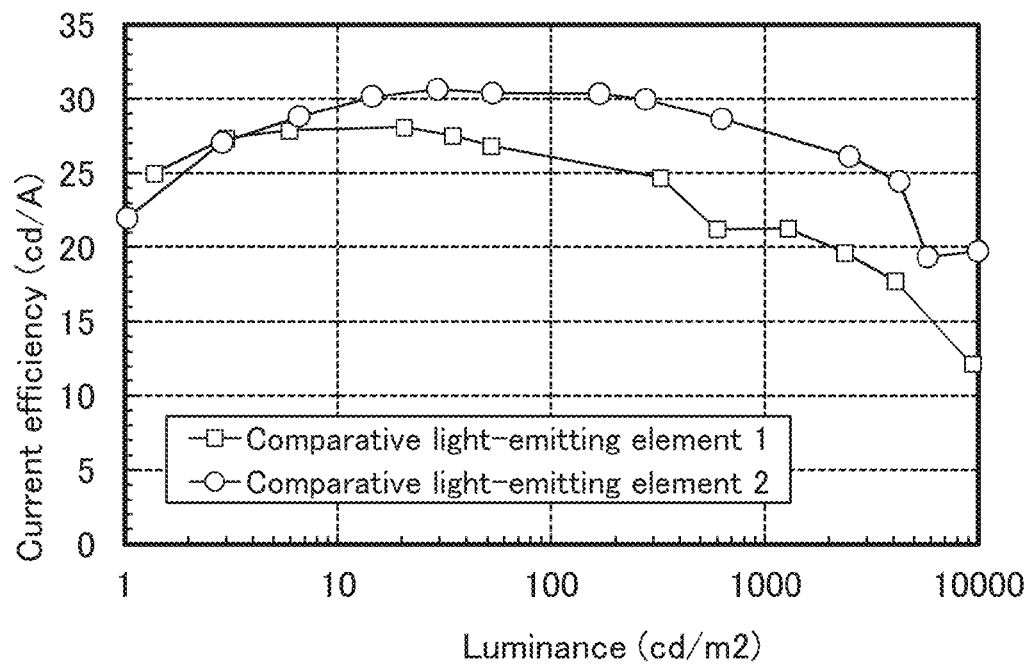
FIG. 29 shows luminance-current efficiency characteristics of a comparative light-emitting element 1 and a comparative light-emitting element 2 manufactured in Example 8.
Figure 30:
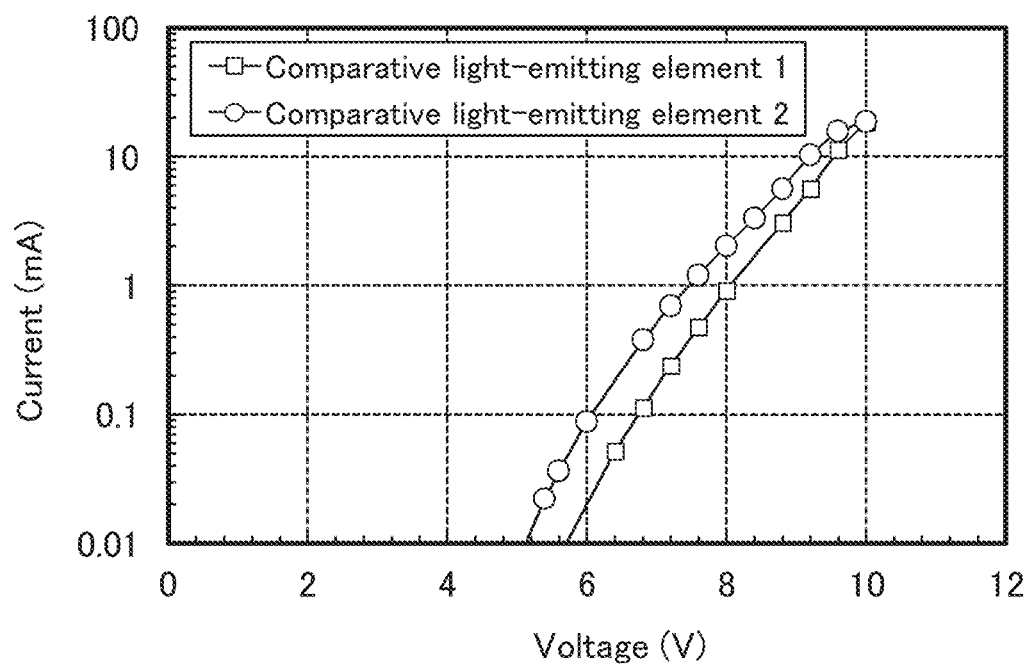
FIG. 30 shows voltage-current characteristics of the comparative light-emitting element 1 and the comparative light-emitting element 2 manufactured in Example 8.
Figure 31:
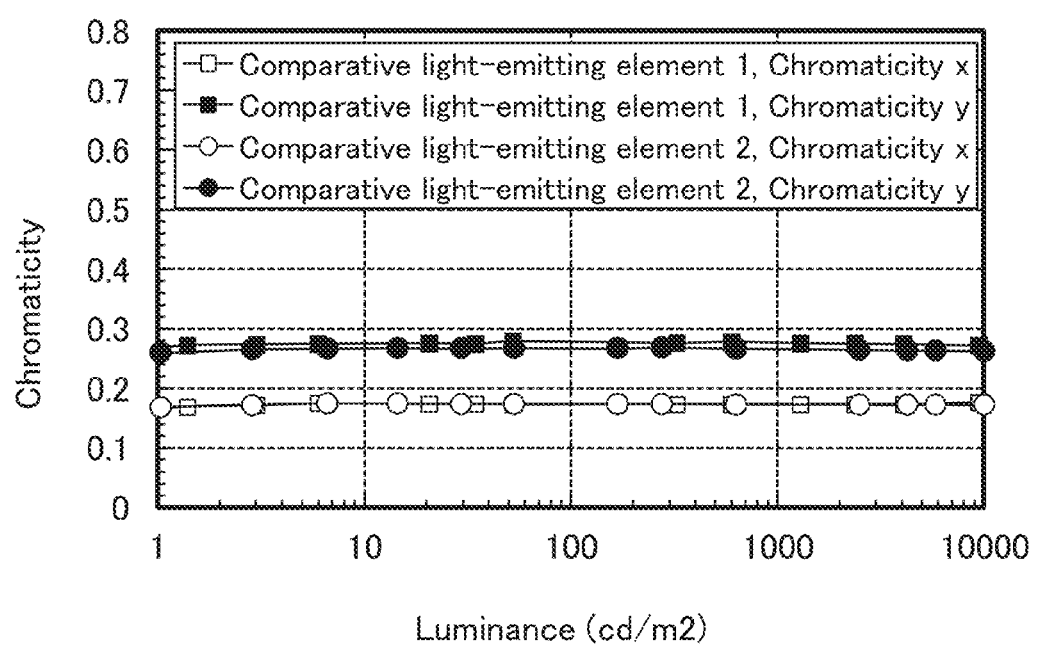
FIG. 31 shows luminance-chromaticity characteristics of the comparative light-emitting elements 1 and 2 manufactured in Example 8.

FIG. 29, the vertical axis represents current efficiency (cd/A) and the horizontal axis represents luminance (cd/m$^2$). FIG. 30 shows voltage-current characteristics of the comparative light-emitting elements 1 and 2. In FIG. 30, the vertical axis represents current (mA) and the horizontal axis represents voltage (V). FIG. 31 shows chromaticity characteristics of the comparative light-emitting elements 1 and 2. In FIG. 31, the vertical axis represents chromaticity and the horizontal axis represents luminance.

Figure 32:
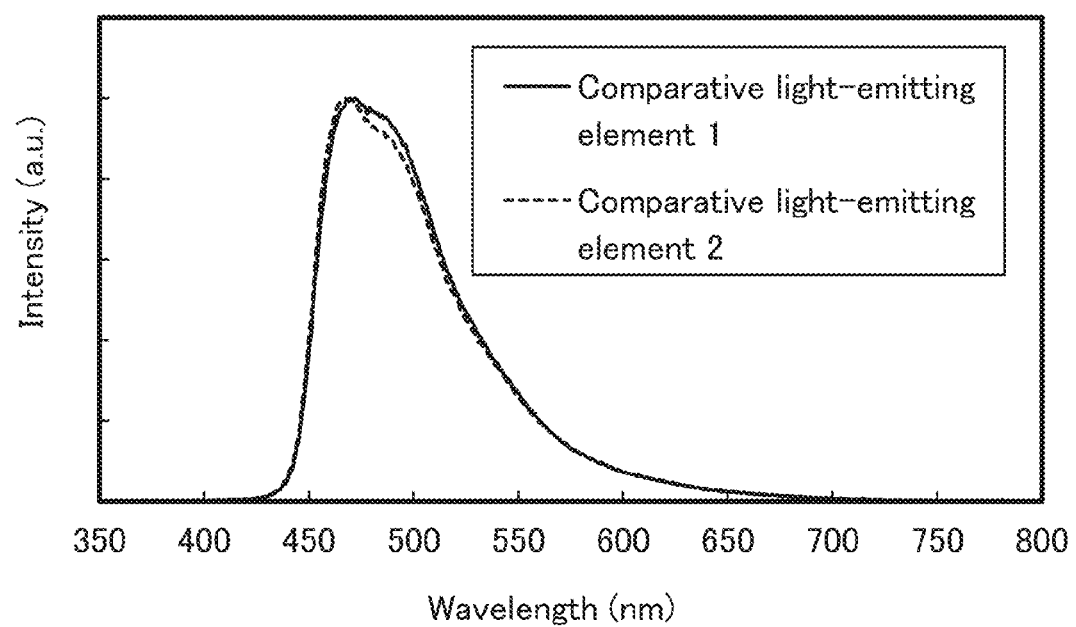
FIG. 32 shows emission spectra of the comparative light-emitting elements 1 and 2 manufactured in Example 8.

FIG. 32 shows emission spectra of the comparative light-emitting elements 1 and 2, which were obtained by applying a current of 0.1 mA to the comparative light-emitting elements 1 and 2. In FIG. 32, the vertical axis represents emission intensity (arbitrary unit) and the horizontal axis represents wavelength (nm). The emission intensity is shown as a value relative to the greatest emission intensity assumed to be 1. As shown in FIG. 32, the emission spectra of the comparative light-emitting elements 1 and 2 each have the maximum emission wavelength at around 466 nm. This means that the comparative light-emitting elements 1 and 2 emit blue light.

Figure 33:
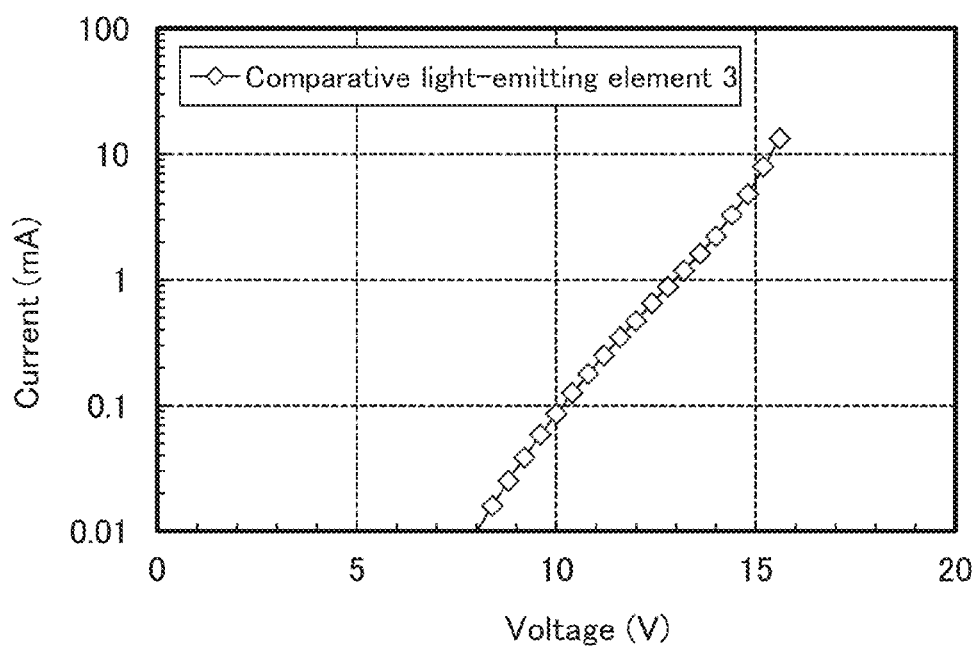
FIG. 33 shows voltage-current characteristics of a comparative light-emitting element 3 manufactured in Example 8.
Figure 34:
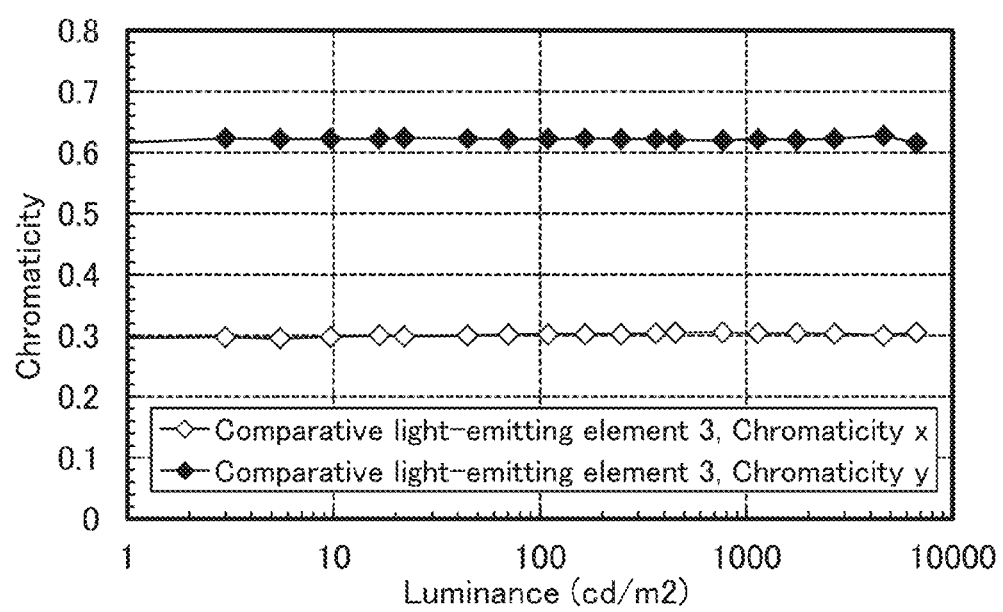
FIG. 34 shows luminance-chromaticity characteristics of the comparative light-emitting element 3 manufactured in Example 8.

FIG. 33 shows voltage-current characteristics of the comparative light-emitting element 3. In FIG. 33, the vertical axis represents current (mA) and the horizontal axis represents voltage (V). In addition, FIG. 34 shows chromaticity characteristics of the comparative light-emitting element 3. In FIG. 34, the vertical axis represents chromaticity and the horizontal axis represents luminance.

Figure 35:
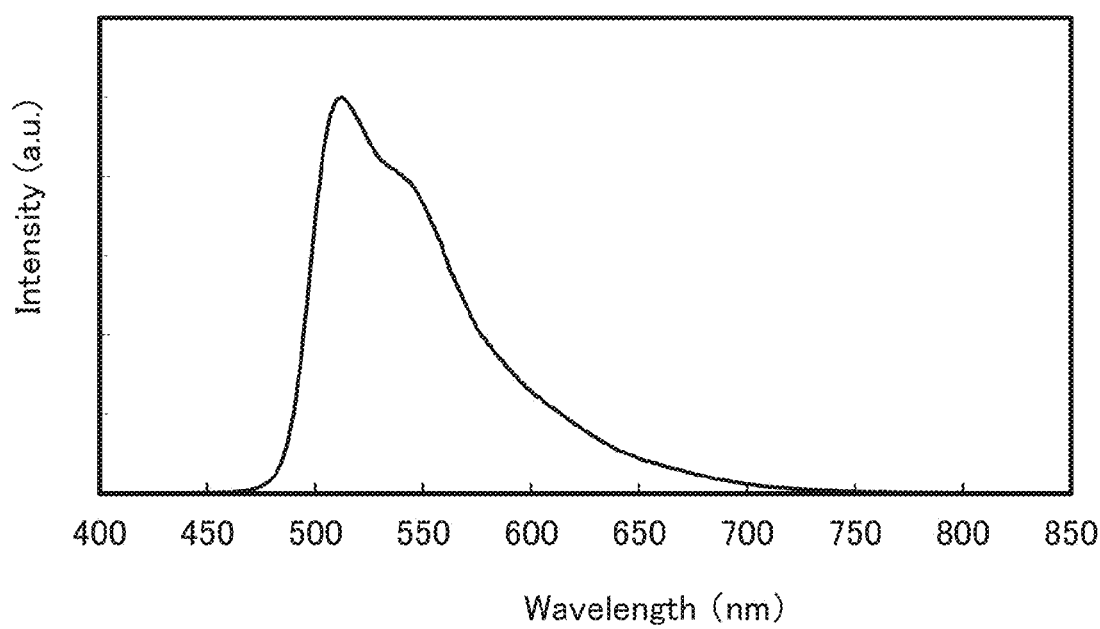
FIG. 35 shows an emission spectrum of the comparative light-emitting element 3 manufactured in Example 8.

FIG. 35 shows an emission spectrum of the comparative light-emitting element 3, which was obtained by applying a

TABLE 11

| | Functional layer | Hole-injection layer | Hole-transport layer | Light-emitting layer | Electron-transport layer | | Electron-injection layer |
|---|---|---|---|---|---|---|---|
| Comparative light-emitting element 3 | Thickness Structure | 60 nm CBP:MoOx = 2:1 | 20 nm 2tBuDfha | 40 nm 2tBuDfha:[Ir(ppy)$_3$] = 1:0.06 | 15 nm mDBTBIm-II | 20 nm BPhen | 1 nm LiF |

Anode: 110 nm ITSO
Cathode: 200 nm Al

<<Operation Characteristics of Light-Emitting Element>>

The comparative light-emitting elements 1, 2, and 3 thus obtained were sealed in a glove box under a nitrogen atmosphere without being exposed to the air. Then, the operation characteristics of the comparative light-emitting elements 1, 2, and 3 were measured. Note that the measurement was carried out at room temperature (in an atmosphere kept at 25° C.).

FIG. 29 shows luminance-current efficiency characteristics of the comparative light-emitting elements 1 and 2. In current of 0.5 mA to the comparative light-emitting element 3. In FIG. 35, the vertical axis represents emission intensity (arbitrary unit) and the horizontal axis represents wavelength (nm). The emission intensity is shown as a value relative to the greatest emission intensity assumed to be 1. As shown in FIG. 35, the emission spectrum of the comparative light-emitting element 3 has the maximum emission wavelength at around 510 nm. This means that the comparative light-emitting element 3 emits green light.

Table 12 shows initial values of main characteristics of the comparative light-emitting elements 1, 2, and 3 at a luminance of approximately 1000 cd/m$^2$.

TABLE 12

| | Voltage (V) | Current (mA) | Current density (mA/cm$^2$) | Chromaticity (x, y) | Luminance (cd/m$^2$) | Current efficiency (cd/A) | Power efficiency (lm/W) |
|---|---|---|---|---|---|---|---|
| Comparative light-emitting element 1 | 7.2 | 0.24 | 6.0 | (0.17, 0.28) | 1280 | 21 | 9.3 |
| Comparative light-emitting element 2 | 6.0 | 0.09 | 2.2 | (0.17, 0.26) | 630 | 29 | 15 |
| Comparative light-emitting element 3 | 14 | 2.23 | 56 | (0.30, 0.62) | 1140 | 2.0 | 0.5 |

FIG. 29 demonstrates that the comparative light-emitting elements 1 and 2 are each a light-emitting element that emits blue phosphorescence and has high efficiency. This is probably because the $T_1$ level of 2tBuDfha (abbreviation) is high as calculated in Example 7. In addition, FIG. 31 demonstrates that the comparative light-emitting elements 1 and 2 each have a small change in chromaticity that depends on luminance and have excellent carrier balance.

The comparative light-emitting element 2 has lower drive voltage and higher efficiency than the comparative light-emitting element 1. This is probably because 2tBuDfha (abbreviation) has the deep HOMO level and the shallow LUMO level as shown in the measurement results in Example 7 and is relatively difficult to oxidize and reduce. Thus, as shown in FIG. 30, the drive voltage is reduced by mixing 2tBuDfha (abbreviation) and 35DCzPPy (abbreviation) that was a carrier-transport material in the light-emitting layer. In addition, the comparative light-emitting element 2 had higher efficiency than the comparative light-emitting element 1 because of the excellent carrier balance. The anthracene compounds of the present invention each also have a relatively deep HOMO level and a relatively shallow LUMO level; thus, by mixing any of the anthracene compounds of the present invention and a carrier-transport material such as PCCP (abbreviation) or 35DCzPPy (abbreviation) the drive voltage is reduced and the efficiency is improved.

Figure 36:
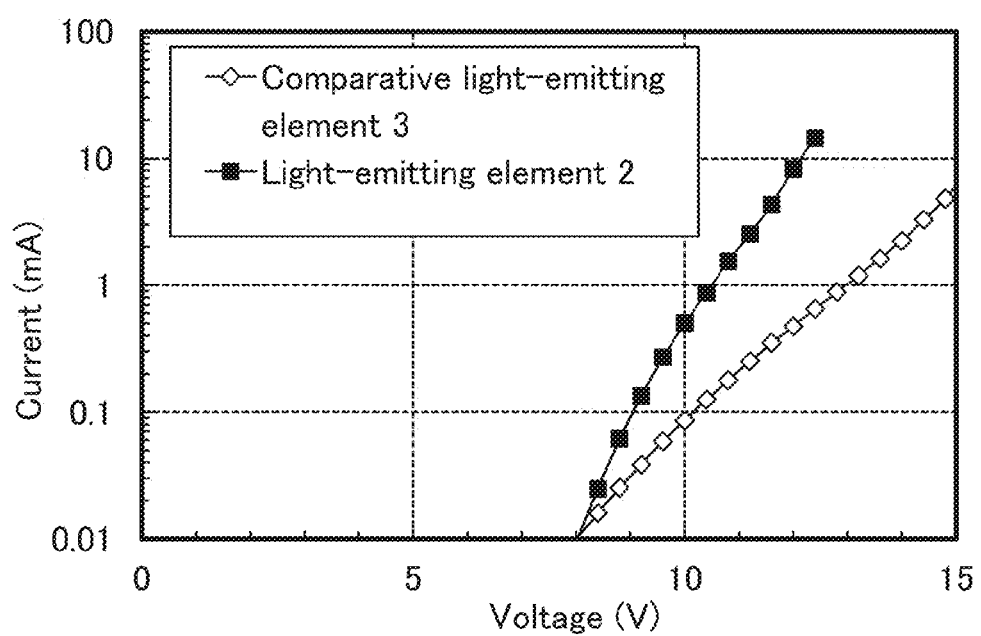
FIG. 36 shows voltage-current characteristics of the light-emitting element 2 manufactured in Example 5 and the comparative light-emitting element 3 manufactured in Example 8.

FIG. 36 shows voltage-current characteristics of the comparative light-emitting element 3 and the light-emitting element 2 described in Example 5. In each of the elements, the same compound is used as a host of the hole-transport layer and a host of the light-emitting layer (2tBuDfha (abbreviation) was used in the comparative light-emitting element 3, and 2mCzPDfha (abbreviation) was used in the light-emitting element 2). Current flows in the light-emitting element 2 more easily than in the comparative light-emitting element 3 when voltage is increased (i.e., the line representing the light-emitting element 2 is steeper than that representing the comparative light-emitting element 3 in FIG. 36). One of the factors is probably that the light-emitting element 2, in which 2mCzPDfha (abbreviation) is used for the hole-transport layer, has a higher hole-transport property than the comparative light-emitting element 3, in which 2tBuDfha (abbreviation) is used for the hole-transport layer. In other words, a carrier-transport property is thought to be improved when an aryl group is bonded to the 2-position of an anthracene skeleton.

The above results show that the anthracene compounds of the present invention each have a high $T_1$ level, a high Tg, and a carrier-transport property, and thus are each suitable as a host material or a carrier-transport material for a light-emitting element, particularly an element emitting phosphorescence in the blue and green regions.

This application is based on Japanese Patent Application serial no. 2013-069849 filed with Japan Patent Office on Mar. 28, 2013, the entire contents of which are hereby incorporated by reference.

What is claimed is:
1. A light-emitting element comprising:
an anode;
a cathode;
a hole-transport layer;
a light-emitting layer; and
an electron-transport layer,
wherein the hole-transport layer, the light-emitting layer, and the electron-transport layer are provided between the anode and the cathode,
wherein the light-emitting layer comprises an anthracene compound represented by General Formula (G1) and a phosphorescent compound, and
wherein one of the hole-transport layer and the electron-transport layer comprises the anthracene compound represented by General Formula (G1),

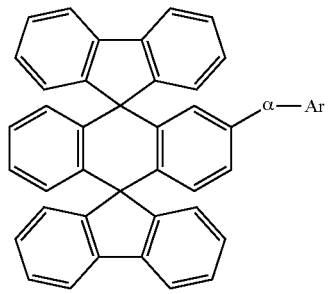

(G1)

wherein α represents a substituted or unsubstituted m-phenylene group or a substituted or unsubstituted 3,3'-biphenyldiyl group,
wherein Ar represents any of a substituted or unsubstituted phenyl group, a substituted or unsubstituted biphenyl group, a substituted or unsubstituted carbazolyl group, a substituted or unsubstituted dibenzothiophenyl group, a substituted or unsubstituted dibenzofuranyl group, a substituted or unsubstituted triphenylenyl group, a substituted or unsubstituted naphthyl group, a substituted or unsubstituted phenanthrenyl group, a substituted or unsubstituted fluorenyl group, a substituted or unsubstituted pyridyl group, a substituted or unsubstituted pyrimidyl group, a substituted or unsubstituted dibenzoquinoxalinyl group, a substituted or unsubstituted benzimidazolyl group, and a substituted or unsubstituted benzoxazolyl group, and wherein in the case where a substituent is bonded to Ar, the substituent is a phenyl group, a biphenyl group, or an alkyl group having 1 to 6 carbon atoms.

2. A light-emitting element comprising:
an anode;
a cathode;
a hole-transport layer;
a light-emitting layer; and
an electron-transport layer,
wherein the hole-transport layer, the light-emitting layer, and the electron-transport layer are provided between the anode and the cathode,
wherein the electron-transport layer comprises an anthracene compound represented by General Formula (G1) and an electron-transport compound,

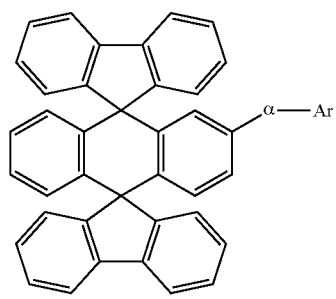

(G1)

wherein α represents a substituted or unsubstituted m-phenylene group or a substituted or unsubstituted 3,3'-biphenyldiyl group, wherein Ar represents any of a substituted or unsubstituted phenyl group, a substituted or unsubstituted biphenyl group, a substituted or unsubstituted carbazolyl group, a substituted or unsubstituted dibenzothiophenyl group, a substituted or unsubstituted dibenzofuranyl group, a substituted or unsubstituted triphenylenyl group, a substituted or unsubstituted naphthyl group, a substituted or unsubstituted phenanthrenyl group, a substituted or unsubstituted fluorenyl group, a substituted or unsubstituted pyridyl group, a substituted or unsubstituted pyrimidyl group, a substituted or unsubstituted dibenzoquinoxalinyl group, a substituted or unsubstituted benzimidazolyl group, and a substituted or unsubstituted benzoxazolyl group, and wherein in the case where a substituent is bonded to Ar, the substituent is a phenyl group, a biphenyl group, or an alkyl group having 1 to 6 carbon atoms.

3. A light-emitting element comprising:
an anode;
a cathode;
a hole-transport layer;
a light-emitting layer; and
an electron-transport layer,
wherein the hole-transport layer, the light-emitting layer, and the electron-transport layer are provided between the anode and the cathode,
wherein the hole-transport layer comprises an anthracene compound represented by General Formula (G1) and a hole-transport compound,

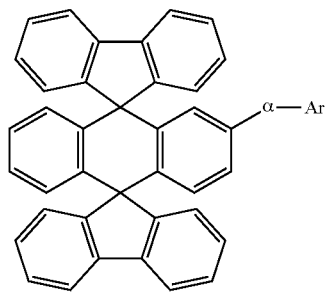

(G1)

wherein α represents a substituted or unsubstituted m-phenylene group or a substituted or unsubstituted 3,3'-biphenyldiyl group, wherein Ar represents any of a substituted or unsubstituted phenyl group, a substituted or unsubstituted biphenyl group, a substituted or unsubstituted carbazolyl group, a substituted or unsubstituted dibenzothiophenyl group, a substituted or unsubstituted dibenzofuranyl group, a substituted or unsubstituted triphenylenyl group, a substituted or unsubstituted naphthyl group, a substituted or unsubstituted phenanthrenyl group, a substituted or unsubstituted fluorenyl group, a substituted or unsubstituted pyridyl group, a substituted or unsubstituted pyrimidyl group, a substituted or unsubstituted dibenzoquinoxalinyl group, a substituted or unsubstituted benzimidazolyl group, and a substituted or unsubstituted benzoxazolyl group, and wherein in the case where a substituent is bonded to Ar, the substituent is a phenyl group, a biphenyl group, or an alkyl group having 1 to 6 carbon atoms.

4. The light-emitting element according to claim 1,
wherein the other of the hole-transport layer and the electron-transport layer comprises the anthracene compound represented by General Formula (G1),
wherein the hole-transport layer further comprises a hole-transport organic compound, and
wherein the electron-transport layer further comprises an electron-transport organic compound.

5. The light-emitting element according to claim 1,
wherein the light-emitting layer further comprises an electron-transport organic compound or a hole-transport organic compound.

6. The light-emitting element according to claim 1,
wherein a phosphorescence wavelength peak is less than or equal to 570 nm.

7. The light-emitting element according to claim 2,
wherein a phosphorescence wavelength peak is less than or equal to 570 nm.

8. The light-emitting element according to claim 3,
wherein a phosphorescence wavelength peak is less than or equal to 570 nm.

9. A compound represented by Structural Formula (100)
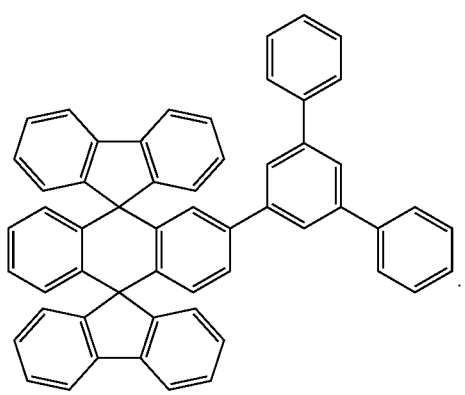
10. A compound represented by Structural Formula (103)
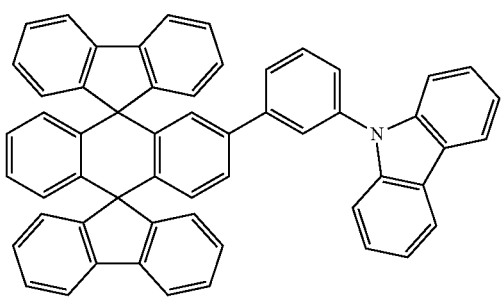
11. A compound represented by Structural Formula (112)
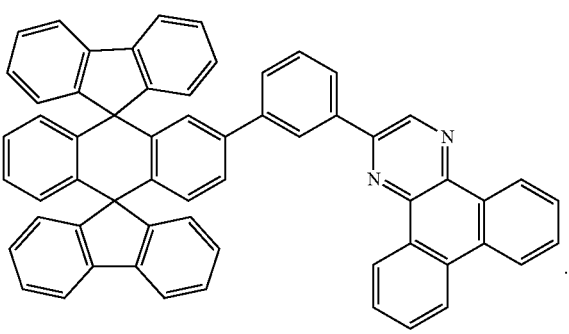
* * * * *

UNITED STATES PATENT AND TRADEMARK OFFICE
CERTIFICATE OF CORRECTION

PATENT NO. : 9,478,749 B2  
APPLICATION NO. : 14/222786  
DATED : October 25, 2016  
INVENTOR(S) : Masato Suzuki et al.

Page 1 of 1

It is certified that error appears in the above-identified patent and that said Letters Patent is hereby corrected as shown below:

In the Specification

Column 8, Line 30, "represented by a" should read --represented by α--

Column 15, Line 39, "N,N-bis" should read --N,N'-bis--

Column 16, Line 28, "Flracac" should read --FIracac--

Column 16, Line 39, "bis[2-(T-benzo" should read --bis[2-(2'-benzo--

Column 17, Line 27, "[gp]" should read --[g,p]--

Column 17, Line 65, "Alg$_a$" should read --Alq$_3$--

Column 28, Line 50, "T-bromo" should read --2'bromo--

Column 31, Line 67, "2rnDBqPDfha" should read --2mDBqPDfha--

Column 33, Line 18, "fluoren]T-yl}" should read --fluoren]2'-yl}--

Column 40, Line 20, "fluorene]T-yl}" should read --fluorene]2'-yl}--

Column 43, Line 55, "fluorene]T-yl}" should read --fluorene]2'-yl}--

Signed and Sealed this  
Twenty-third Day of May, 2017

Michelle K. Lee  
*Director of the United States Patent and Trademark Office*